United States Patent
Weir et al.

(10) Patent No.: US 9,081,020 B2
(45) Date of Patent: Jul. 14, 2015

(54) MUTANT PROTEINS AND METHODS FOR SELECTING THEM

(75) Inventors: Malcolm Peter Weir, Welwyn Garden City (GB); Richard Henderson, Cambridge (GB); Christopher Gordon Tate, Cambridge (GB); Edward Christopher Hulme, London (GB)

(73) Assignee: Heptares Therapeutics Limited, Hertfordshire (GB)

( * ) Notice: Subject to any disclaimer, the term of this patent is extended or adjusted under 35 U.S.C. 154(b) by 2 days.

(21) Appl. No.: 12/866,594

(22) PCT Filed: Feb. 5, 2009

(86) PCT No.: PCT/GB2009/000310
§ 371 (c)(1),
(2), (4) Date: Nov. 15, 2010

(87) PCT Pub. No.: WO2009/101383
PCT Pub. Date: Aug. 20, 2009

(65) Prior Publication Data
US 2011/0046351 A1    Feb. 24, 2011

(30) Foreign Application Priority Data
Feb. 11, 2008  (GB) .................................. 0802474.7

(51) Int. Cl.
*G01N 33/74* (2006.01)
*G01N 33/68* (2006.01)
*G01N 33/53* (2006.01)
*C07K 14/705* (2006.01)

(52) U.S. Cl.
CPC .......... *G01N 33/74* (2013.01); *C07K 14/70571* (2013.01); *G01N 33/6872* (2013.01); *G01N 2333/726* (2013.01)

(58) Field of Classification Search
CPC ............ G01N 33/53; G01N 2333/726; G01N 2333/705; G01N 33/74; G01N 33/68; C12Q 1/485; C07K 14/723
See application file for complete search history.

(56) References Cited

U.S. PATENT DOCUMENTS

| | | | |
|---|---|---|---|
| 4,816,567 A | 3/1989 | Cabilly et al. |
| 4,946,778 A | 8/1990 | Ladner et al. |
| 5,223,409 A | 6/1993 | Ladner et al. |
| 5,290,681 A | 3/1994 | Kuroda et al. |
| 5,585,277 A | 12/1996 | Bowie et al. |
| 5,834,250 A | 11/1998 | Wells et al. |
| 5,925,549 A | 7/1999 | Hsueh et al. |
| 6,153,410 A | 11/2000 | Arnold et al. |
| 6,448,377 B1 | 9/2002 | Kobilka et al. |
| 6,537,749 B2 | 3/2003 | Kuimelis et al. |
| 7,094,593 B1 | 8/2006 | Pausch et al. |
| 7,115,377 B2 | 10/2006 | Yao et al. |
| 7,462,457 B2 | 12/2008 | Beachy et al. |
| 2002/0028443 A1 | 3/2002 | Short |
| 2002/0147170 A1 | 10/2002 | Kopin et al. |
| 2003/0036092 A1 | 2/2003 | Iverson et al. |
| 2003/0096297 A1 | 5/2003 | Gilchrist et al. |
| 2003/0129649 A1 | 7/2003 | Kobilka et al. |
| 2003/0232331 A1 | 12/2003 | Casman et al. |
| 2004/0157268 A1 | 8/2004 | Kobilka et al. |
| 2005/0136392 A1 | 6/2005 | Torres et al. |
| 2005/0143402 A1 | 6/2005 | Cheetham et al. |
| 2005/0287565 A1 | 12/2005 | Merchiers et al. |
| 2007/0154947 A1 | 7/2007 | Broach et al. |
| 2007/0196389 A1 | 8/2007 | Caligiuri et al. |
| 2010/0190188 A1 | 7/2010 | Henderson et al. |
| 2011/0027910 A1 | 2/2011 | Weir et al. |
| 2011/0028700 A1 | 2/2011 | Heal |
| 2011/0112037 A1 | 5/2011 | Warne et al. |
| 2012/0165507 A1 | 6/2012 | Jazayeri-Dezfuly et al. |
| 2012/0270230 A1 | 10/2012 | Henderson et al. |
| 2013/0224238 A1 | 8/2013 | Hutchings et al. |
| 2014/0031525 A1 | 1/2014 | Robertson et al. |

FOREIGN PATENT DOCUMENTS

| | | |
|---|---|---|
| EP | 0 184 187 A2 | 6/1986 |
| EP | 0 239 400 A2 | 9/1987 |
| EP | 0 397 834 B1 | 2/2000 |
| EP | 1 376 132 A1 | 1/2004 |
| EP | 1 505 074 A1 | 2/2005 |
| GB | 2 188 638 A | 10/1987 |
| WO | WO 91/17271 A1 | 11/1991 |
| WO | WO 92/01047 A1 | 1/1992 |
| WO | WO 92/09690 A2 | 6/1992 |
| WO | WO 92/15679 A1 | 9/1992 |

(Continued)

OTHER PUBLICATIONS

Robertson, N. et al., "The properties of thermostabilized G protein-coupled receptors (StaRs) and their use in drug discovery," Neuropharmacology 60: 36-44, 2011.

(Continued)

*Primary Examiner* — Ruixiang Li
(74) *Attorney, Agent, or Firm* — Wolf, Greenfield & Sacks, P.C.

(57) ABSTRACT

A method for selecting a membrane protein with increased stability, the method comprising: a) providing one or more mutants of a parent membrane protein in a membrane-containing composition, wherein the one or more mutants are exposed to an amount of a membrane destabilizing agent which is effective to destabilize the parent membrane protein in-situ, b) determining whether the or each mutant membrane protein has increased stability with respect to its structure and/or a biological activity compared to the stability of the parent membrane protein with respect to its structure and/or the same biological activity, and c) selecting the one or more mutants which have increased stability compared to the stability of the parent membrane protein.

21 Claims, 16 Drawing Sheets

(56) References Cited

FOREIGN PATENT DOCUMENTS

Figure 1:
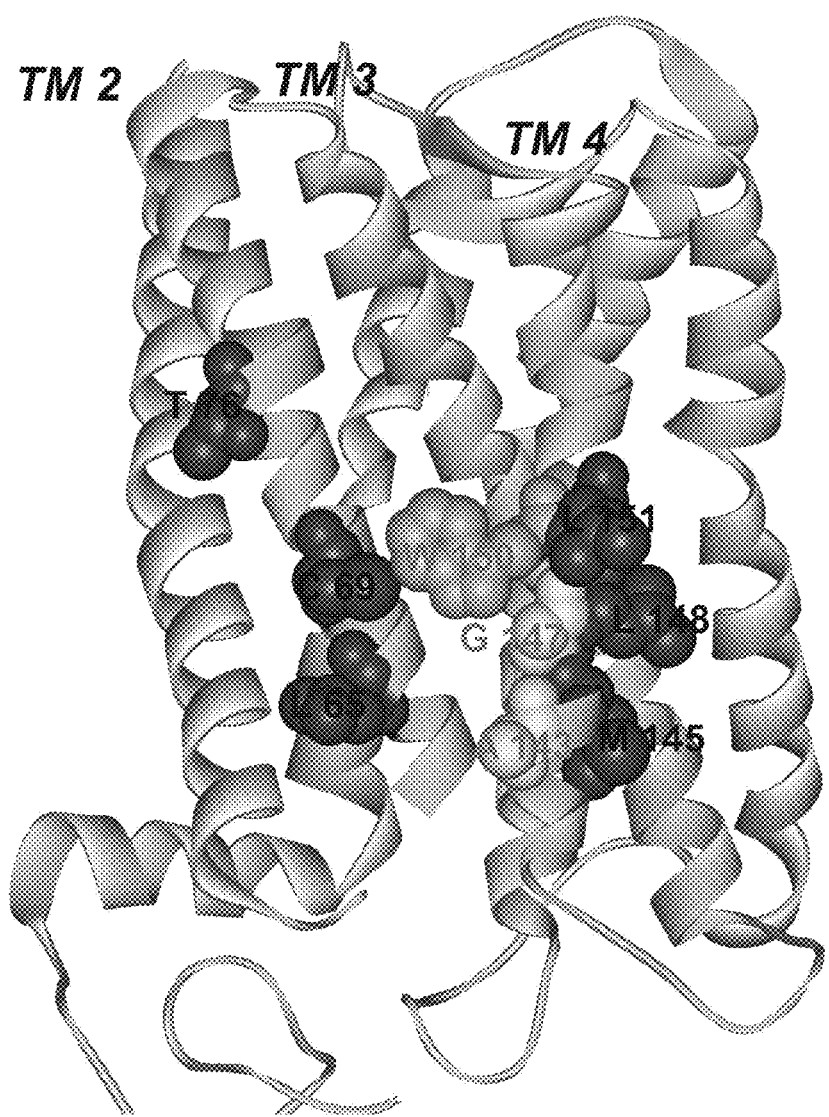

| | | |
|---|---|---|
| WO | WO 92/18619 A1 | 10/1992 |
| WO | WO 92/20791 A1 | 11/1992 |
| WO | WO 93/01288 A1 | 1/1993 |
| WO | WO 95/32425 A1 | 11/1995 |
| WO | WO 97/35881 A2 | 10/1997 |
| WO | WO 00/22129 A1 | 4/2000 |
| WO | WO 01/36471 A2 | 5/2001 |
| WO | WO 02/059346 A2 | 8/2002 |
| WO | WO 02/068600 A2 | 9/2002 |
| WO | WO 03/035693 A2 | 5/2003 |
| WO | WO 2005/121755 A1 | 12/2005 |
| WO | WO 2006/023248 A2 | 3/2006 |
| WO | WO 2008/068534 A2 | 6/2008 |
| WO | WO 2008/114020 A2 | 9/2008 |
| WO | WO 2009/071914 A2 | 6/2009 |
| WO | WO 2009/081136 A2 | 7/2009 |

OTHER PUBLICATIONS

Shoichet, B. et al., "Structure-based drug screening for G-protein-coupled receptors," Trends in Pharma Science 33(5): 268-272, 2012.
Alberts et al., Solubilizing membrane proteins with a mild detergent. Molecular Biology of the Cell. 2002;4$^{th}$ Edition. New York: Garland Science. Figure 10-24.
Hulme et al., Phenotypic classification of mutants: a tool for understanding ligand binding and activation of muscarinic acetylcholine receptors. Biochem Soc Trans. Aug. 2007;35(Pt 4):742-5.
Lehmann et al., The consensus concept for thermostability engineering of proteins. Biochim Biophys Acta. Dec. 29, 2000;1543(2):408-415.
Lu et al., Transmembrane domains 4 and 7 of the M(1) muscarinic acetylcholine receptor are critical for ligand binding and the receptor activation switch. J Biol Chem. Sep. 7, 2001;276(36):34098-104. Epub Jul. 5, 2001.
Pogozheva et al., Interactions of human melanocortin 4 receptor with nonpeptide and peptide agonists. Biochemistry. Aug. 30, 2005;44(34):11329-41.
Schimerlik, Overview of membrane protein solubilization. Current Protocols in Neuroscience. 2001;5.9.1-5.9.5. Abstract.
Scopes, 4.7 Precipitation by Selective Denaturation. General Principles. Purification: Principles and Practice. 3$^{rd}$ Edition. 1994:95.
Voet et al., Protein Stability. Chapter 7: Three-Dimensional Structures of Proteins; Section 7-4. Biochemistry 2$^{nd}$ Edition. 1995. 179-180.
Zhang et al., Adopting selected hydrogen bonding and ionic interactions from *Aspergillus fumigatus* phytase structure improves the thermostability of *Aspergillus niger* PhyA phytase. Appl Environ Microbiol. May 2007;73(9):3069-76. Epub Mar. 9, 2007.
Flanagan, A GPCR that is not "Dry". Mol Pharmacol. Jul. 2005;68(1):1-3. Epub Apr. 26, 2005.
Ghanouni et al., The effect of pH on beta(2) adrenoceptor function. Evidence for protonation-dependent activation. J Biol Chem. Feb. 4, 2000;275(5):3121-7.
Privé, Detergents for the stabilization and crystallization of membrane proteins. Methods. Apr. 2007;41(4):388-97.
Xie et al., An opsin mutant with increased thermal stability. Biochemistry. Feb. 25, 2003;42(7):1995-2001.
Bockaert and Pin. Molecular tinkering of G protein-coupled receptors: an evolutionary success. EMBO J. 1999. 18:1723-1729.
Bockaert et al., GPCR-GIP networks: a first step in the discovery of new therapeutic drugs? Curr Opin Drug Discov and Dev. 2004. 7:649-657.
Bohm. The computer program LUDI: a new method for the de novo design of enzyme inhibitors. J. Comput. Aided Mol. Des. 1992. 6:61-78.
Bommarius et al., High-throughput screening for enhanced protein stability. Curr Opin Biotechnol. 2006. 17(6):606-610. Epub Oct. 17, 2006.
Bonner et al., Identification of a family of muscarinic acetylcholine receptor genes. Science. 1987. 237:527-532.
Boucard et al., Constitutive Activation of the Angiotensin II Type 1 Receptor Alters the Spatial Proximity of Transmembrane 7 to the Ligand-binding Pocket. J. Biol. Chem. 2003. 278(38):36628-36636. Epub Jul. 3, 2003.
Bowie. Stabilizing membrane proteins. Curr. Opin. Struct. Biol. 2001. 11(4):397-402.
Brenner & Lerner. Encoded combinatorial chemistry. PNAS. 1992. 89:5381-5383.
Brodeur et al., Mouse-Human Myeloma Partners for the Production of Heterohybridomas. Mono. Antib. Prod. Tech. Apps. 1987. 51-63.
Brunger et al., Recent developments for the efficient crystallographic refinement of macromolecular structures. Curr. Opin. Struct. Biol. 1998. 8(5):606-611.
Bruns et al., Human glutathione transferase A4-4 crystal structures and mutagenesis reveal the basis of high catalytic efficiency with toxic lipid peroxidation products. J Mol Biol. 1999. 288:427-439.
Burstein et al., The second intracellular loop of the m5 muscarinic receptor is the switch which enables G-protein coupling. J Biol Chem. 1998. 273:24322-24327.
Caron et al., Affinity chromatography of the beta-adrenergic receptor. J. Biol. Chem.1979. 254:2923-2927.
Carrillo H. & Lipman D.J. The multiple sequence alignment problem in biology. SIAM J. Appl. Math. 1988; 48:1073-1082.
Carson. Ribbons 2.0. Appl. Crystallogr. 1991. 24:958-961.
Chan et al., Allosteric modulation of the muscarinic M4 receptor as an approach to treating schizophrenia. PNAS. 2008. 105:10978-10983.
Chapple et al., Multiplexed expression and screening for recombinant protein production in mammalian cells. BMC Biotechnol. 2006. 22:6-49.
Cherezov et al., A robotic system for crystallizing membrane and soluble proteins in lipidic mesophases. Acta. Crystallogr. D. Biol. Crystallogr. 2004. 60(Pt 10):1795-1807. Epub Sep. 23, 2004.
Cherezov et al., Crystallization Screens: Compatibility with the Lipidic Cubic Phase for in Meso Crystallization of Membrane Proteins. Biophys. J. 2001. 81:225-242.
Cherezov et al., High Resolution Crystal Structure of an Engineered Human β2-Adrenergic G protein-Coupled Receptor. Science. 2007. 318(5854):1258-1265. Epub Oct. 25, 2007.
Cherezov et al., Room to Move: Crystallizing Membrane Proteins in Swollen Lipidic Mesophases. J. Mol. Biol. 2006. 357:1605-1618.
Christopoulos. Allosteric binding sites on cell-surface receptors: Novel targets for drug discovery. Nat. Rev. Drug Discov. 2002. 1:198-210.
Clackson et al., Making antibody fragments using phage display libraries. Nature. 1991. 352:624-628.
Claeysen et al., A single mutation in the 5-HT4 receptor (5-HT4-R D100(3.32)A) generates a Gs-coupled receptor activated exclusively by synthetic ligands (RASSL).J Biol Chem. Jan. 10, 2003;278(2):699-702. Epub Nov. 18, 2002.
Cohen et al., Molecular modeling software and methods for medicinal chemistry. J. Med. Chem. 1990. 33:883-894.
Conklin et al., Engineering Gpcr signaling pathways with RASSLs. Nat Methods. Aug. 2008;5(8):673-8.
Cooper. Advances in membrane receptor screening and analysis. J. Mol. Recognit. 2004. 17(4):286-315.
Cooper. Non-optical screening platforms: the next wave in label-free screening? Drug Discov. Today. 2006. 11(23-24):1068-1074. Epub Oct. 20, 2006.
Cornell et al., A Second Generation Force Field for the Simulation of Proteins, Nucleic Acids, and Organic Molecules. JACS. 1995. 1 17(19):5179-5197.
D'Antona et al., A cannabinoid receptor 1 mutation proximal to the DRY motif results in constitutive activty and reveals intramolecular interactions involved in receptor activation. Brain Research. 2006 1108(1):1-11.
D'Antona et al., Mutations of CB1 T210 Produce Active and Inactive Receptor Forms: Correlations with Ligand Affinity, Receptor Stability, and Cellular Localization. Biochemistry. 2006. 45:5606-5617.
Day et al., A monoclonal antibody for G protein-coupled receptor crystallography. Nat Methods. 2007. 4(11):927-929.
Degrip. Thermal Stability of Rhodopsin and Opsin in Some Novel Detergents. Methods in Enzymology. 1982. 81:256-265.

(56) References Cited

OTHER PUBLICATIONS

Devereux et al., A comprehensive set of sequence analysis programs for the VAX; Nucl. Acids Rec. 12:387-395, 1984.
Dignam. Preparation of extracts from higher eukaryotes. Methods in Enzymology. 1990. 182:194-203.
Domazet et al., The second transmembrane domain of the human type 1 angiotensin II receptor participates in the formation of the ligand binding pocket and undergoes integral pivoting movement during the process of receptor activation. J Biol Chem. May 1, 2009;284(18):11922-9. Epub Mar. 9, 2009.
Dupriez et al. Aequorin-based functional assays for G-protein-coupled receptors, ion channels and tyrosine kinase receptors. Receptors Channels. 2002. 8(5-6):319-330.
Duthey et al., A Single Subunit (GB2) is Required for G-protein Activation by the Heterodimeric GABAB Receptor: J. Biol.Chem 277(5):3236-3241, 2002.
Dyson et al., Identification of soluble protein fragments by gene fragmentation and genetic selection. Nucl. Acid Research. 2008. 36:e51.
Dyson et al., Production of soluble mammalian proteins in *Escherichia coli*: identification of protein features that correlate with successful expression. BMC Biotechnology. 2004. 4:32.
Eddy et al., Maximum Discrimination Hidden Markov Models of Sequence Consensus. J. Comput Biol. 1995. 2(1):9-23.
Eglen. Functional G protein-coupled receptor assays for primary and secondary screening. Comb. Chem. High Throughput Screen. 2005. 8(4):311-318.
Eisen et al., HOOK: a program for finding novel molecular architectures that satisfy the chemical and steric requirements of a macromolecule binding site. Proteins:Structure, Function and Genetics. 1994. 19(3):199-221.
Eldridge et al., Empirical scoring functions: I. the development of a fast empirical scoring function to estimate the binding affinity of ligands in receptor complexes. J. Comp. Aided Mol. Des. 1997. 11(5):425-445.
Ernst et al., Intrinsic biophysical monitors of transducin activation: fluorescence, UV-visible spectroscopy, light scattering, and evanescent field techniques. Meth. Enzymol. 2000. 315:471-489.
Evans & McCoy. An introduction to molecular replacement. Acta Crystallogr. 2008. D64:1-10.
Faham et al., Side-chain contributions to membrane protein structure and stability. J. Mol. Biol. 2004. 335:297-305.
Fanelli. Theoretical study on mutation-induced activation of the luteinizing hormone receptor. J. Mol. Biol. 2000. 296(5):1333-1351.
Fang et al., G protein-coupled receptor microarrays for drug discovery. Drug Discovery Today. 2003. 8:755-761.
Felix et al., Immunoadsorption as a new therapeutic principle for treatment of dilated cardiomyopathy. Eur. Heart J. Supplements. 2002. 4:163-168.
Ferracci et al., Real time analysis of intact organelles using surface plasmon resonance. Anal. Biochem. 2004. 334:367-375.
Ferro & Hermans. A different best rigid body molecular fit routine. Acta Cryst. 1977. A33:345-347.
Fetrow & Bryant. New programs for protein tertiary structure prediction. Biotechnology. 1993. 11(4):479-484.
Folkertsma et al., A family-based approach reveals the function of residues in the nuclear receptor ligand-binding domain. J. Mol. Biol. 2004. 341(2):321-335.
Foord et al., International Union of Pharmacology. XLVI. G Protein-Coupled Receptor List. Pharmacol. Rev. 2005. 57:279-288.
Foord S.M. & Marshall F.H. RAMPs: accessory proteins for seven transmembrane domain receptors, Trends Pharmacol Sci. 20(5):184-187 1999.
Frändberg et al., Cysteine Residues Are Involved in Structure and Function of Melanocortin 1 Receptor: Substitution of a Cysteine Residue in Transmembrane Segment Two Converts an Agonist to Antagonist. Biochem. Biophys. Res. Commun. 2001. 281(4):851-857.
Frielle et al., Cloning of the cDNA for the human-β-adrenergic receptor. PNAS. 1987. 84:7920-7924.

Fuchs et al., Targeting recombinant antibodies to the surface of *Escherichia coli*: fusion to a peptidglycan associated lipoprotein. Biotechnology. 1991. 9:1369-1372.
Gales et al., Real-time monitoring of receptor and G-protein interactions in living cells, Nat. Methods. 2(3):177-184 (2005).
Garcia-Lopez et al., Strategies for design of non peptide CCK1R agonist/antagonist ligands. Curr. Top. Med. Chem. 2007. 7(12):1180-1194.
Gardella et al., Transmembrane residues of the parathyroid hormone (PTH)/PTH-related peptide receptor that specifically affect binding and signaling by agonist ligands. J Biol Chem. May 31, 1996;271(22):12820-5.
Garrard et al., $F_{ab}$ assembly and enrichment in a monovalent phage display system. Biotechnology. 1991. 9:1373-1377.
Gerber et al., An Activation Switch in the Ligand Binding Pocket of the C5a Receptor. J. Biol. Chem. 2001. 276(5):3394-3400.
Gether et al., Structural Instability of a Constitutively Active G Protein-coupled Receptor Agonist-Independent Activation Due to Conformational Flexibility. J. Biol. Chem. 1997. 272:2587-2590.
Gether. Uncovering Molecular Mechanisms Involved in Activation of G Protein-Coupled Receptors. Endocr. Rev. 2000. 21:90-113.
Gillet et al., SPROUT—a program for structure generation. J. Comput. Aided Mol. Des.1993. 7:127-153.
Ginalski, Comparative modeling for protein structure prediction. Curr. Op. Struct. Biol. 2006. 16(2):172-177.
Gish & States. Identification of protein coding regions by database similarity search. Nature Genetics. 1993. 3:266-272.
Goding. Production of Monoclonal Antibodies: Principles and Practice. Academic Press. 1986. 59-103.
Gonzalez & Maher. Cellular Fluorescent Indicators and Voltage/Ion Probe Reader (VIPR) Tools for Ion Channel and Receptor Drug Discovery. Receptors Channels.8(5-6):283-295, 2002.
Goodford. A Computational Procedure for Determining Energetically Favorable Binding Sites on Biologically Important Macromolecules. J. Med. Chem. 1985. 28:849-857.
Goodsell et al., Automated docking of substrates to proteins by simulated annealing. Proteins: Structure, Function and Genetics. 1990. 8:195-202.
Gram et al., In vitro selection and affinity maturation of antibodies from a naïve combinatorial immunoglobulin library. PNAS. 1992. 89:3576-3580.
Graneli et al., Characterization of a proton pumping transmembrane protein incorporated into a supported three-dimensional matrix of proteoliposomes. Anal. Biochem. 2007. 367:87-94.
Graneli et al., Utilizing adsorbed proteoliposomes trapped in a non-ruptured state on SiO2 for amplified detection of membrane proteins. Biosens. Bioelectron. 2004. 20:498-504.
Gray et al., Identification of Two Serine Residues Essential for Agonist-Induced 5-HT2a Receptor Desensitization. Biochemistry. 2003. 42(36):10853-10862.
Gray. High-resolution protein-protein docking. Curr. Opin. Struct. Biol. 2006. 16:183-193.
Greer et al., Application of the Three-Dimensional Structures of Protein Target Molecules in Structure-Based Drug Design. J. Med. Chem. 1994. 37:1035-1054.
Greer. Comparative modeling of homologous proteins. Methods in Enzymology. 1991. 202:239-252.
Greer. Model structure for the inflammatory protein C5a. Science. 1985. 228:1055-1060.
Griffiths et al. Human anti-self antibodies with high specificity from phage display libraries. EMBO J. 1993. 12:725-734.
Grindley et al., Identification of Tertiary Structure Resemblance in Proteins Using a Maximal Common Subgraph Isomorphism Algorithm. J. Mol. Biol. 1993. 229:707-721.
Grisshamer et al. Expression of a rat neurotensin receptor in *Escherichia coli*. Biochem J. 1993. 295(2):571-576.
Grisshammer & Tate. Overexpression of integral membrane proteins for structural studies. Q. Rev. Biophys. 1995. 28:315-422.
Groves & Dustin. Supported planar bilayers in studies on immune cell adhesion and communication. Immunol. Meth. 2003. 278:19-32.
Groves. Membrane array technology for drug discovery. Curr. Op. Drug Discov. Develop. 2002. 5:606-612.

(56) References Cited

OTHER PUBLICATIONS

Gschwend & Kuntz. Orientational sampling and rigid-body minimization in molecular docking revisited: on-the-fly optimization and degeneracy removal. J. Comput. Aided Mol. Des. 1996. 10:123-132.
Guida. Software for structure-based drug design. Curr. Opin. Struct. Biol. 1994. 4:777-781.
Gupta & Devi. The use of receptor-specific antibodies to study G-protein-coupled receptors. Mt. Sinai J. Med. 2006. 73(4):673-681.
Gupta et al., Conformation State-sensitive Antibodies to G-protein-coupled Receptors. J. Biol. Chem. 2007. 282(8): 5116-5124.
Halperin et al., Principles of docking: An overview of search algorithms and a guide to scoring functions. Proteins. 2002. 47:409-443.
Hamuro et al., Hydrogen/deuterium-exchange (H/D-Ex) of PPAR$\gamma$ LBD in the presence of various modulators. Protein Science. 2006. 15(8):1883-1892.
Han et al., Constitutive activation of opsin by mutation of methionine 257 on transmembrane helix 6. Biochemistry. Jun. 2, 1998;37(22):8253-61.
Harding et al., Direct analysis of a GPCR-agonist interaction by surface plasmon resonance. Eur. Biophys. J. Biophys. Let. 2006. 35:709-712.
Harding. Metal-ligand geometry relevant to proteins and in proteins: sodium and potassium. Acta Crystallogr. 2002. D58:872-874.
Hawkins et al., Selection of phage antibodies by binding affinity: mimicking affinity maturation. J. Mol. Biol. 1992. 226:889-896.
Hay et al., Bacteriophage Cloning and *Escherichia coli* Expression of a Human IgM Fab. Hum. Antibod. Hybridomas. 1992. 3:81-85.
Hendrickson. Transformations to optimize the superposition of similar structures. Acta Crystallogr. 1979. A35:158-163.
Henikoff & Henikoff. Amino acid substitution matrices from protein blocks. Proc Natl Acad Sci U.S.A. Nov. 15, 1992; 89(22):10915-10919.
Hoffmann et al., A FlAsH-based Fret approach to determine G protein-coupled receptor activation in living cells. Nat Methods. Mar. 2005;2(3):171-6. Epub Feb. 17, 2005.
Holm & Sander. Dali/FSSP classification of three-dimensional protein folds. Nucl. Acids Res. 1997. 25:231-234.
Holm & Sander. Mapping the Protein Universe. Science. 1996. 273:595-602.
Hoogenboom et al., Multi-subunit proteins on the surface of filamentous phage: methodologies for displaying antibody (Fab) heavy and light chains. Nuc. Acid Res. 1991. 19:4133-4137.
Hopkins & Groom. The druggable genome. Nature Rev. Drug Discovery. 2002. 1:727-730.
Hoppe & Schomburg. Prediction of protein thermostability with a direction- and distance-dependent knowledge-based potential. Protein Science. 2005. 14:2682-2692.
Huang et al., A probabilistic method to correlate ion pairs with protein thermostability. Applied Bioinformics. 2004. 3(1):21-29.
Hubbell et al., Rhodopsin structure, dynamics, and activation: a perspective from crystallography, site-directed spin labeling, sulfhydryl reactivity, and disulfide cross-linking. Adv. Protein Chem. 2003. 63:243-290.
Hudson et al., High content screening of known G protein-coupled receptors by arrestin translocation. Methods Enzymol. 414:63-78, 2006.
Hulme & Curtis. Purification of recombinant M1 muscarinic acetylcholine receptor. Biochemical Society Transactions. 1998. 26:S361.
Hunte et al., Structure at 2.3 Å resolution of the cytochrome bc1 complex from the yeast *Saccharomyces cerevisiae* co-crystallized with an antibody Fv fragment. Structure. 2000. 8:669-684.
Hus et al. Assignment strategy of proteins with known structure. J. Magn. Reson. 2002. 157(1):119-123.
Huse et al., Generation of a large combinatorial library of the immunoglobulin repertoire in phage lambda. Science. 1989. 246:1275-1281.
Ikuta et al., Crystallographic Approach to Identification of Cyclin-dependent Kinase 4 (CDK4)-specific Inhibitors by Using CDK4 Mimic CDK2 Protein. J. Biol. Chem. 2001. 276:27548-27554.
Isogaya et al., Binding pockets of the $\beta1$ and $\beta2$ adrenergic receptors for subtype-selective agonists. Mol. Pharmacol. 1999. 56(5):875-885.
Isogaya et al., Identification of a Key Amino Acid of the $\beta2$-Adrenergic Receptor for High Affinity Binding of Salmeterol. Mol. Pharmacol. 1998. 54:616-622.
Jaakola et al., The 2.6 Å Crystal Structure of a Human A2A Adenosine Receptor Bound to an Antagonist. Science. 2008. 322:1211-1217.
Jaenicke & Bohm. The stability of proteins in extreme environments. Current Opinion in Structural Biology. 1998. 8:738-748.
Jahns et al., Direct evidence for a $\beta1$-adrenergic receptor-directed autoimmune attack as a cause of idiopathic dilated cardiomyopathy. J. Clinical Investigation. 2004. 113(10):1419-1429.
Jahns et al., Modulation of Beta1-Adrenoceptor Activity by Domain-Specific Antibodies and Heart Failure-Associated Autoantibodies. J. Am. Coll. Cardiol. 2000. 36(4):1280-1287.
Jameson et al., Real-time Detection of Basal and Stimulated G Protein GTPase Activity Using Fluorescent GTP Analogues. J. Biol. Chem. 2005. 280(9):7712-7719.
Jane-wit D. et al., $\beta1$-Adrenergic Receptor Autoantibodies Mediate Dilated Cardiomyopathy by Agonistically Inducing Cardiomyocyte Apoptosis. Circulation. 2007. 116(4):399-410. Epub Jul. 9, 2007.
Jap et al., 2D crystallization: from art to science; Ultramicroscopy. 1992. 46(1-4):45-84.
Jerne & Nordin. Plaque formation in agar in single antibody-producing cells. Science. 1963. 140:405.
Johnson & Chriswell. Human antibody engineering. Curr. Op. Structural Biol. 1993. 3:564-571.
Johnson et al., A 1,536-well 35S GTPgammaS scintillation proximity binging assay for ultra-high-throughput screening of an orphan galphai-coupled GPCR. Assay Drug Dev Technol 6, 327-337 (2008).
Johnson et al., Knowledge-based protein modeling. Crit Rev Biochem Mol Biol. 1994. 29:1-68.
Jones et al., Development and validation of a genetic algorithm for flexible docking. J Mol. Biol. 1997. 267:727-748.
Jones et al., Docking small-molecule ligands into active sites. Curr. Opin. Biotech. 1995. 6:652-656.
Jones et al., Improved methods for building protein models in electron density maps and the location of errors in these models. Acta Crystallogr. 1991. A47:110-119.
Jones et al., Molecular Recognition of Receptor Sites Using a Genetic Algorithm with a Description of Desolvation. J Mol Biol. 1995. 245:43-53.
Kabsch, A discussion of the solution for the best rotation to relate two sets of vectors. Acta Crystallogr. 1978. A34:827-828.
Kabsch., A solution of the best rotation to relate two sets of vectors. Acta Crystallogr. 1976. A32:922-23.
Karlin & Altschul. Applications and statistics for multiple high-scoring segments in molecular sequences. PNAS. 1993. 90:5873-5877.
Karlsson & Lofas. Flow-Mediated On-Surface Reconstitution of G-Protein Coupled Receptors for Applications in Surface Plasmon Resonance Biosensors. Anal. Biochem. 2002. 300(2):132-138.
Kearsley. On the orthogonal transformation used for structural comparisons. Acta Crystallogr. 1989. A45:208-210.
Kenakin et al., Protean agonists. Keys to active receptor states? Ann. N.Y. Acad. Sci. 1997. 812:116-125.
Kenakin. Inverse, protean, and ligand-selective agonism: matters of receptor conformation. FASEB J. 2001. 15(3):598-611.
Kent et al., Development of a Generic Dual-Reporter Gene Assay for Screening G-Protein-Coupled Receptors. J. Biomol. Screen. 2005. 10(5):437-446.
Kent et al., G-protein-coupled receptor heterodimerization: assay technologies to clinical significance. Curr. Opin. Drug Discov. Devel. 2007. 10(5):580-589.
Kerr et al., Encoded combinational peptide libraries containing non-natural amino acids. JACS. 1993. 115:2529-2531.
Kikkawa et al., The Role of the Seventh Transmembrane Region in High Affinity Binding of a b2-Selective Agonist TA-2005. Mol. Pharmacol. 1998. 53:128-134.
Klco et al., Essential role for the second extracellular loop in C5a receptor activation. Nat Struct Mol Biol. 2005. 12:320-326.

(56) References Cited

OTHER PUBLICATIONS

Kleywegt & Jones. A super position. CCP4/ESF-EACBM Newsletter on Protein Crystallography. 1994. 31:9-14.
Kobilka & Deupi. Conformation complexity of G-protein coupled receptors. Trends in Pharmacological Sciences. 2007. 28(8):397-406.
Kobilka & Schertler. New G-protein-coupled receptor crystal structures: insights and limitations. Trends Pharm. Sci. 2008. 29(2):79-83.
Köhler & Milstein. Continuous cultures of fused cells secreting antibody of predefined specificity. Nature. 1975. 256:495-497.
Komolov et al., Surface Plasmon Resonance Study of G Protein/Receptor Coupling in a Lipid Bilayer-Free System. Anal. Chem. 2006. 78:1228-1234.
Kozbor et al., A human hybrid myeloma for production of human monoclonal antibodies. J. Immunol. 1984. 133:3001-3005.
Kristiansen. Molecular mechanisms of ligand binding, signalling, and regulation within the superfamily of G-protein-coupled receptors: molecular modelling and mutagenesis approaches to receptor structure and function. Pharmacology and therapeutics. 2004. 103:21-80.
Kuhlbrandt. Three-dimensional crystallization of membrane proteins. Q. Rev. Biophys. 1988. 21:429-477.
Kuhlbrandt. Two-dimensional crystallization of membrane proteins. Q. Rev. Biophys. 1992. 25(1):1-49.
Kukkonen et al., Muscarinic Toxin 7 Selectivity Is Dictated by Extracellular Receptor Loops. J. Biol. Chem. 2004. 279:50923-50929.
Kuntz et al., A Geometric Approach to Macromolecule-Ligand Interactions. J. Mol. Biol. 1982. 161:269-288.
Kuroda et al., Systems for the detection and analysis of protein-protein interactions. Appl. Microbiol. Biotechnol. 2006. 71(2):127-136.
Kyte & Doolittle. A Simple Method for Displaying the Hydropathic Character of a Protein. J. Mol. Biol. 1982. 157:105-132.
Labbé-Jullié C. et al., 1998, Mutagenesis and Modeling of the Neurotensin Receptor NTRI, Journal of Biological Chemistry, 273(26):16351-16357.
Lamb et al., Modulation of the ligand binding properties of the transcription repressor NmrA by GATA-containing DNA and site-directed mutagenesis. Prot. Sci. 2004. 13(12):3127-3138.
Landau & Rosenbusch. Lipidic cubic phases: A novel concept for the crystallization of membrane proteins. PNAS USA. 1996. 93:14532-14535.
Lane et al., Protean agonism at the dopamine D2 receptor: (S)-3-(3-hydroxyphenyl)-N-propylpiperidine is an agonist for activation of Goi but an antigonist/inverse agonist for Gi1, Gi2, and Gi3. Mil Pharmacol. 2007 71(5):1349-1359. Epub Feb. 7, 2007.
Lang et al., Structure-activity relationship studies: Methods and ligand design for g-protein coupled peptide receptors. Curr. Prot. Peptide Sci. 2006. 7:335-353.
Latronico et al., Gonadotropin-Independent Precocious Puberty Due to Luteinizing Hormone Receptor Mutations in Brazilian Boys: A Novel Constitutively Activating Mutation in the First Transmembrane Helix. J. Clin. Endocrinol. Metabl. 2000. 85(12):4799-4805.
Lattion et al., Constitutively active mutants of the β1-adrenergic receptor. FEBS Letters 1999 457(3):302-306.
Lattman. Use of Rotation and Translation Functions. Meth. Enzymol. 1985. 115:55-77.
Lau et al., Changing single side chains can greatly enhance the resistance of a membrane protein to irreversible inactivation. J. Mol. Biol. 1999. 290:559-564.
Lauri & Bartlett. CAVEAT: A Program to Facilitate the Design of Organic Molecules. J. Comp. Aided Mol. Design. 1994. 8:51-66.
Lee et al., Alanine scanning mutagenesis of conserved arginine/lysine-arginine/lysine-x-x-arginie/lysine G protein/activating motifs on M1 muscarinic acetylcholine receptors. Molecular Pharmacology. 1996 50(1):140-148.
Lee et al., D2 Dopamine receptor homodimerization is mediated by multiple sites of interaction, including an intermolecular interaction involving transmembrane domain 4. Biochemistry. 2003. 42(37):11023-31.
Lee et al., State of the art in studying protein folding and protein structure predictio using molecular dynamics methods. J. Mol. Graph & Modelling. 2001. 19(1):146-149.
Lefèvre et al., Alanine-stretch scanning mutagenesis: a simple and efficient method to probe protein structure and function. Nucl. Acids Res. 1997. 25(2):447-448.
Lehmann et al., The consensus concept for thermostability engineering of proteins: further proof of concept. Protein Engineering. 2002. 15(5):403-411.
Leifert et al., G-Protein-Coupled Receptors in Drug Discovery: Nanosizing Using Cell-Free Technologies and Molecular Biology Approaches. J. Biomol. Screening. 2005. 10:765-779.
Leroy et al., G Protein-coupled receptor-mediated ERK1/2 phosphorylation: towards a generic sensor of GPCR activation. J. Recept. Signal. Transduct. Res. 2007. 27(1):83-97.
Lewis & Lofthouse. Adverse reactions with beta-adrenoceptor blocking drugs: an update. Drug Safety. 1993. 9:272-279.
Li et al., Distinct Structural Changes in a G Protein-coupled Receptor Caused by Different Classes of Agonist Ligands. J. Biol. Chem. 2007. 282(36):26284-26293.
Li et al., Random Mutagenesis of the M3 Muscarinic Acetylcholine Receptor Expressed in Yeast. J. Biol. Chem. 2005. 280:5664-5675.
Li et al., Structure of Bovine Rhodopsin in a Trigonal Crystal Form. J. Mol. Biol. 2004. 343:1409-1438.
Liu & Wu. Analysis of the coupling of G12/13 to G protein-coupled receptors using a luciferase reporter assay. Methods Mol. Biol. 2004. 237:145-149.
Lohse et al. Kinetic analysis of G protein-coupled receptor signaling using fluorescence resonance energy transfer in living cells. Adv Protein Chem 2007 74:167-188.
Luecke et al., Structure of bacteriorhodopsin at 1.55 A resolution. J. Mol. Biol. 1999. 291(4):899-911.
Maclean et al., Encoded combinatorial chemistry: Synthesis and screening of a library of highly functionalized pyrrolidines. PNAS. 1997. 94:2805-2810.
Madabushi et al., Evolutionary Trace of G Protein-coupled Receptors Reveals Clusters of Residues That Determine Global and Class-specific Functions; J Biol Chem 2004 279(9):8126-8132.
Magnani et al., Co-evolving stability and conformational homogeneity of the human adenosine A2a receptor. PNAS. 2008. 105(31):10744-10749.
Makino et al., Automated flexible ligand docking method and its application for database search. J Comput. Chem. 1997. 18:1812-1825.
Marshall. Heterodimerization of G-protein-coupled receptors in the CNS. Curr. Opin. Pharmacol. 2001. 1(1):40-44.
Martin et al., A simple vector system to improve performance and utilisation of recombinant antibodies. BMC Biotechnology. 2006. 6:46.
Martin et al., Apolipoprotein A-I Assumes a "Looped Belt" Conformation on Reconstituted High Density Lipoprotein. J. Biol. Chem. 2006. 281(29):20418-20426.
Martin. 3D Database searching in drug design. J. Med. Chem. 1992. 35:2145-2154.
Martin-Garcia et al., Interaction with CD4 and Antibodies to CD4-Induced Epitopes of the Envelope gp120 from a Microglial Cell-Adapted Human Immunodeficiency Virus Type 1 Isolate. J. Virology. 2005. 79:6703-6713.
Mathews & Rossmann. Comparison of Protein Structures. Methods of Enzymology. 1985. 115:397-420.
Matsui et al., Specific removal of β1-adrenoceptor autoantibodies by immunoabsorption in rabbits with autoimmune cardiomyopathy improved cardiac structure and function. J. Mol. Cell Cardiol. 2006. 41(1):78-85. epub Jun. 14, 2006.
McCafferty et al., Phage antibodies: filamentous phage displaying antibody variable domains. Nature. 1990. 348:552-554.
McCoy. Phaser crystallographic software. Acta Crystallogr. 2007. 40:658-674.

(56) References Cited

OTHER PUBLICATIONS

McCoy. Solving Structures of protein complexes by molecular replacement with Phaser. Acta Crystallogr. 2007. D63:32-41.
McLachlan. Gene duplications in the structural evolution of chymotrypsin. J. Mol. Biol. 1979. 128, 49-79.
Mehler et al., Ab initio computational modelling of loops in G-protein-coupled receptors: Lessons from the crystal structure of rhodopsin. Proteins Structures Function and Bioinformatics. 2006. 64(3):673-690.
Meng et al., Automated docking with grid-based energy evaluation. J. Comp. Chem. 1992. 13:505-524.
Mezzasalma et al., Enhancing recombinant protein quality and yield by protein stability profiling. J. Biolmol. Screening. 2007. 12(3):418-428.
Michaelson et al., Antibodies to muscarinic acetylcholine receptors in myasthenia gravis. Biochem. Biophys. Res. Commun. 1982. 104(1):52-57.
Milligan & White. Protein-protein interactions at G-protein-coupled receptors. Trends Pharmacol. Sci. 2001. 22:513-518.
Milligan. G protein-coupled receptor dimerisation: Molecular basis and relevance to function. Biochim. Biophys Acta. 2007. 1768(4):825-835.
Milstein & Cuello. Hybrid hybridomas and their use in immunohistochemistry. Nature. 1983. 305:537-540.
Minic et al., Immobilization of native membrane-bound rhodopsin on biosensor surfaces. Biochim. Biophys. Acta-General Subjects. 2005. 1924:324-332.
Minneman et al., A Comparison of the Beta-Adrenergic Receptor of the Turkey Erythrocyte with Mammalian Beta1 and Beta2 Receptors. Mol. Pharmacol. 1980. 17:1-7.
Miranker et al., Functionality Maps of Binding Sites: A Multiple Copy Simultaneous Search Method Proteins: Structure, Function and Genetics. 1991. 11:29-34.
Misquitta et al. Membrane Protein Crystallization in Lipidic Mesophases with Tailored Bilayers. Structure. 2004. 12:2113-2124.
Moran et al., Radio frequency tag encoded combinatorial library method for the discovery of tripeptide-substituted cinnamic acid inhibitors of the protein tyrosine phosphatase PTB1B. JACS. 1995. 117:10787-10788.
Morris et al., Automated docking using a Lamarckian genetic algorithm and an empirical binding free energy function. J. Comput. Chem. 1998. 19:1639-1662.
Morrison. Success in specification. Nature. 1994. 368:812-813.
Mozsolits et al., Surface plasmon resonance spectroscopy in the study of membrane-mediated cell signalling. J. Peptide Sci. 2003. 9:77-89.
Munson & Rodbard. Ligand: a versatile computerized approach for characterization of ligand-binding systems. Anal. Biochem. 1980. 107:220-239.
Murakami et al., Crystal structure of squid rhodopsin. Nature. May 15, 2008;453(7193):363-7.
Myburgh et al., A single amino acid substitution in transmembrane helix VI results in overexpression of the human GnRH receptor. Eur. J. Endocrinol. 1998. 139(4):438-447.
Navarro et al., Receptor-Dependent G-Protein activation in Lipidic Cubic phase. Biopolymers. 2002. 67:167-177.
Navaza. AMoRe: an Automated Package for Molecular Replacement. Acta Cryst. 1994. D50:157-163.
Navia & Murko. Use of structural information in drug design. Curr Opin Struc Biol. 1992. 2:202-210.
Navratilova et al., Analyzing ligand and small molecule binding activity of solubilized GPCRs using biosensor technology. Anal. Biochem. 2006. 355:132-139.
Nawaratne et al., New insights into the function of M4 muscarinic acetylcholine receptors gained using a novel allosteric modulator and a DREADD (designer receptor exclusively activated by a designer drug). Mol Pharmacol. Oct. 2008;74(4):1119-31. Epub Jul. 15, 2008.
Needleman SB & Wunsch C.D. A general method applicable to the search for similarities in the amino acid sequence of two proteins. J Mol Biol Mar. 1970; 48(3):443-453.

Neubig et al., International Union of Pharmacology Committee on Receptor Nomenclature and Drug Classification. XXXVIII. Update on Terms and Symbols in Quantitative Pharmacology. Pharmacol. Rev. 2003. 55:597-606.
Newman-Tancredi et al., Agonist and inverse agonist efficacy at human recombinant serotonin 5-HT1A receptors as a function of receptor:G-protein stoichiometry. Neurophamacology. 1997. 36:451-459.
Nicolaou et al., Radiofrequency encoded combinatorial chemistry. Angew. Chem. Int. Ed. Engl. 1995. 34:2289-2291.
Nishibata et al., Automatic creation of drug candidate structures based on receptor structure. Starting point for artificial lead generation. Tetrahedron. 1991. 47:8985-8990.
Nunomura et al., Regulation of Protein 4.1R, p55, and Glycophorin C Ternary Complex in Human Erythrocyte Membrane. J. Biol. Chem. 2000. 275:24540-24546.
Ohlmeyer et al., Complex synthetic chemical libraries indexed with molecular tags. PNAS. 1993. 90:10922-10926.
Oldham et al., Mapping allosteric connections from the receptor to the nucleotide-binding pocket of heterotrimeric G proteins. PNAS. 2007. 104(19):7927-7932.
Omerovic et al., Induction of Cardiomyopathy in Immunodeficiency Mice by Transfer Patients with Idiopathic Dilated Cardiomyopathy. Autoimmunity. 2000. 32(4):271-280.
Osbourn et al., Directed selection of MIP-1 alpha neutralizing CCR5 antibodies from a phage display human antibody library. Nature Biotechnology. 1998. 16:778-781.
Ostermeier & Michel. Crystalization of Membrane Proteins. Curr. Opin. Struct. Biol. 1997. 7:697-701.
Ott et al., Engineering and functional immobilization of opioid receptors. Prot. Eng. Design & Selection. 2005. 18:153-160.
Overington et al., How many drug targets are there? Natur Rev. Drug Discovery. 2006. 5:993-996.
Palczewski et al., Crystal Structure of Rhodopsin: A G Protein-Coupled Receptor. Science. 2000. 289:739-745.
Palmer et al., Treatment of systemic lupus erythematosus by extracorporeal immunoadsorption. Lancet. 1988. 2(8605):272.
Pardo et al., The role of internal water molecules in the structure and function of the rhodopsin family of G protein-coupled receptors. Chembiochem. Jan. 2, 2007;8(1):19-24.
Park et al., Characterization of radioligand binding to a transmembrane receptor reconstituted into Lipobeads. FEBS Lett. 2004. 567:344-348.
Parker & Ross. Truncation of the Extended Carboxyl-terminal Domain Increases the Expression and Regulatory Activity of the Avian,& Adrenergic Receptor. J. Biol. Chem. 1991. 266:9987-9996.
Parker et al., Carboxyl terminal domains in the avian β1-adrenergic receptor that regulate agonist-promoted endocytosis. J. Biol. Chem. 1995. 270:6482-6487. Erratum in: J Biol Chem 1995. 270(17):10358.
Parker et al., Reconstitutively Active G Protein-coupled Receptors Purified from Baculovirus-infected Insect Cells. J. Biol. Chem. 1991. 266:519-527.
Parsons et al., Directing phage selections towards specific epitopes. Protein Engineering. 1996. 9:1043-1049.
Perez. From Plants to Man: The GPCR "Tree of Life". Mol. Pharmacol. 2005. 67:1383-1384.
Pin et al., Evolution, structure, and activation mechanism of family 3/C G-protein-coupled receptor, Pharm. & Ther. 2003 98 325-354.
Plant et al., Phospholipid/alkanethiol bilayers for cell-surface receptor studies by surface plasmon resonance. Analyt. Biochem. 1995. 226(2):342-348.
Ponsioen et al. Detecting cAMP-induced Epac activation by fluorescence resonance energy transfer: epac as a novel cAMP indicator, 2004 EMBO Rep.;5(12):1176-1180.
Qian et al., High-resolution structure prediction and the crystallographic phase problem. Nature. 2007. 450:259-264.
Quick & Javitch. Monitoring the function of membrane transport proteins in detergent-solubilized form. PNAS. 2007. 104(9):3603-3608.
Rarey et al., A fast flexible docking method using an incremental construction algorithm. J. Mol. Biol. 1996. 261:470-489.

(56) References Cited

OTHER PUBLICATIONS

Rasmussen et al., Crystal structure of the human β2 adrenergic g-protein-coupled receptor. Nature. 2007. 450:383-387.

Rasmussen et al., Mutation of a Highly Conserved Aspartic Acid in the β2 Adrenergic Receptor: Constitutive Activation, Structural Instability, and Conformational Rearrangement of Transmembrane Segment 6. Molecular Pharmacol. 1999. 56:175-84.

Riekel et al., Protein crystallography microdiffraction. Curr. Opin. Struct. Biol. 2005. 15(5):556-562.

Rigaut et al., A generic protein purification method for protein complex characterization and proteome exploration. Nature Biotechnol. 1999. 17(10):1030-1032.

Roberts & Strange. Mechanisms of inverse agonist action at D2 dopamine receptors. Br. J. Pharmacol. 2005. 145:34-42.

Robinson-Rechavi et al., Contribution of Electrostatic Interactions, Compactness and Quaternary Structure to Protein Thermostability: Lessons from Structural Genomics of *Thermotoga maritima*. J. Mol. Biol. 2006. 356:547-557.

Rodgers et al., Development of displacement binding and GTPγS scintillation proximity assays for the identification of antagonists of the μ-opiod receptor. Assay Drug Dev. Technol. 2003. 1(5):627-636.

Rosenbaum et al., GPCR Engineering Yields High-Resolution Structural Insights into b2-Adrenergic Receptor Function. Science. 2007. 318:1266-1273.

Rossmann & Argos. A Comparison of the Heme Binding Pocket in Globins and Cytochrome b. J. Biol. Chem. 1975. 250:7525-7532.

Roth et al., Stabilization of the β2-adrenergic Receptor 4-3-5 Helix Interface by Mutagenesis of Glu-1223.41, A Critical Residue in GPCR Structure. J. Mol. Biol. 2008. 376:1305-1319.

Rovati et al., The Highly Conserved DRY Motif of Class A G Protein-Coupled Receptors: Beyond the Ground State. Mol. Pharmacol. 2007. 71(4):959-964.

Rummel et al., Lipidic Cubic Phases: New Matrices for the Three-Dimensional Crystallization of Membrane Proteins. J. Struct. Biol. 1998. 121:82-91.

Sali & Blundell. Comparative protein modelling of satisfaction by spatial restraints. J. Mol. Biol. 1993. 234(3):779-815.

Samama et al., A mutation-induced activated state of the β2-adrenergic receptor. J Biol Chem. 1993 268(7):4625-4636.

Sarkar et al., Directed evolution of a G protein-coupled receptor for expression, stability, and binding selectivity. PNAS. 2008. 105(39):14808-14813.

Savinainen et al., Identification of WIN55212-3 as a competitive neutral antagonist of the human cannabinoid CB2 receptor. Br. J. Pharmacol. 2005. 145:636-645.

Sayle et al., RASMOL: biomolecular graphics for all. Trends in Biochemical Sciences. 1995. 20:374-376.

Scarselli et al., Multiple Residues in the Second Extracellular Loop Are Critical for M3 Muscarinic Acetylcholine Receptor Activation. J. Biol. Chem. 2007. 282:7385-7396.

Schaffner & Weissmann. A Rapid, Sensitive, and Specific Method for the Determination of Protein in Dilute Solution. Anal. Biochem. 1973. 56:502-514.

Schena et al., Quantitative monitoring of gene expression patterns with a complementary DNA microarray. Science. 1995. 270:467-470.

Schnare et al. Comprehensive comparison of structural characteristics in eukaryotic cytoplasmic large subunit (23S-like) ribosomal RNA. J. Mol. Biol. 1996. 256:701-719.

Schofield et al., Application of phage display to high throughput antibody generation and characterization. Genome Biology. 2007. 8(11):R254.

Schultz et al., Requirement of Specific Intrahelical Interactions for Stabilizing the Inactive Conformation of Glycoprotein Hormone Receptors. J. Biol. Chem. 2000. 275(48):37860-37869.

Screpanti et al., Crucial Steps in the Structure Determination of the Na+/H+ Antiporter NhaA in its Native Conformation. J. Mol. Biol. 2006. 362:192-202.

Sebestyen et al., Efficiency and limitations of the 'portioning-mixing' peptide synthesis. Pept. Proc. Eur. Pept. Symp. 22nd 1992. 1993. 63-64.

Sen et al., Functional studies with membrane-bound and detergent-solubilized alpha2-adrenergic receptors expressed in Sf9 cells. Biochim Biophys Acta. 2005 1712(1):62-70. Epub Apr. 26, 2005.

Serrano-Vega et al., Conformational thermostabilisation of the β1-adrenergic receptor in a detergent-resistant form. PNAS. 2008 105(3):877-882.

Shi & Javitch. The second extracellular loop of the dopamine D2 receptor lines the binding-site crevice. PNAS 2004. 101:440-445.

Shi et al., Beta2 adrenergic receptor activation. Modulation of the proline kink in transmembrane 6 by a rotamer toggle switch. J Biol Chem. Oct. 25, 2002;277(43):40989-96. Epub Aug. 6, 2002.

Shibata et al. Thermostabilization of the Neurotensin Receptor NTS1, J. Mol. Biol. 2009 390(2):262-277.

Skerra. 'Anticalins': a new class of engineered ligand-binding proteins with antibody-like properties. J. Biotechnol. 2001. 74(4):257-275.

Sobek et al., Microarray technology as a universal tool for high-throughput analysis of biological systems. Combinat. Chem. & High Throughput Screening. 2006. 9:365-380.

Spalding et al., Structural Requirements of Transmembrane Domain 3 for Activation by the M1 Muscarinic Receptor Agonists AC-42, AC-260584, Clozapine, and N-Desmethylclozapine: Evidence for Three Distinct Modes of Receptor Activation. Mol. Pharmacol. 2006. 70:1974-1983.

Standfuss et al., Crystal Structure of a thermally stable rhodopsin mutant. J Mol Biol. 2007 372(5):1179-1188.

Steipe et al., Sequence statistics reliably predict stabilizing mutations in a protein domain. J. Mol. Biol. 1994. 240:188-192.

Stenlund et al., Capture and reconstitution of G protein-coupled receptors on a biosensor surface. Analytical Biochemistry. 2003. 316:243-250.

Stock et al., Robotic nanolitre protein crystallisation at the MRC Laboratory of Molecular Biology. Prog. Biophys. Mil. Biol. 2005. 88:311-327.

Sugimoto et al., Beta(1)-selective agonist (-)-1-(3,4-dimethoxyphenetylamino)-3-(3,4-dihydroxy)-2-propanol [(-)-RO363] differentially interacts with key amino acids responsible for beta(1)-selective binding in resting and active states. J Pharmacol Exp Ther. Apr. 2002;301(1):51-8.

Sung et al., Rhodopsin Mutations Responsible for Autosomal Dominant Retinitis Pigmentosa. J. Biol. Chem. 1993. 268(35):26645-26649.

Sutcliffe et al., Knowledge based modelling of homologous proteins, part I: three-dimensional frameworks derived from the simultaneous superposition of multiple structures. Protein Eng. 1987. 1:377-384.

Swaminath et al., Sequential Binding of Agonists to the 2 Adrenoceptor. J. Biol. Chem. 2004. 279(1):686-691.

Szklarz & Halpert. Use of homology modeling in conjunction with site-directed mutagenesis for analysis of structure-function relationships of mammalian cyfochromes P450. Life Sci. 1997. 61:2507-2520.

Tan et al., FGF and stress regulate CREB and ATF-1 via a pathway involving p38 MAP kinase and MAPKAP kinase-2. EMBO J. 1996. 15(17):4629-4642.

Tao et al., Chimeras of the Rat and Human FSH Receptors (FSHRs) Identify Residues that Permit or Suppress Transmembrane 6 Mutation-Induced Constitutive Activation of the FSHR via Rearrangements of Hydrophobic Interactions Between Helices 6 and 7. Mol. Endocrinol. 2002. 16(8):1881-1892.

Tate. Overexpression of mammalian integral membrane proteins for structural studies. FEBS Lett. 2001. 504:94-98.

Tate. Baculovirus-Mediated Expression of Neurotransmitter Transporters. Methods Enzymol. 1998. 296:443-455.

Teng et al., Control of feeding behavior in *C. elegans* by human G protein-coupled receptors permits screening for agonist-expressing bacteria. PNAS. 2008. 105(39):14826-14831.

Teng et al., Expression of mammalian GPCRs in *C. elegans* generates novel behavioural responses to human ligands. BMC Biology. 2006. 4:22.

(56) References Cited

OTHER PUBLICATIONS

Themmen & Huhtaniemi. Mutations of Gonadotropins and Gonadotropin Receptors: Elucidating the Physiology and Pathophysiology of Pituitary-Gonadal Function. Endocr. Rev. 2000. 21(5):551-583.
Thompson et al., CLUSTAL W: improving the sensitivity of progressive multiple sequence alignment through sequence weighting, position-specific gap penalties and weight matrix choice Nucl. Acids Res. 1994. 22:4673-4680.
Topiol & Sabio. Use of the X-ray structure of the β2-adrenergic receptor for drug discovery. Bioorganic & Medicinal Chemistry. 2008. 18(5):1598-1602.
Traunecker et al., Bispecific single chain molecules (Janusins) target cytotoxic lymphocytes on HIV infected cells. EMBO J. 1991. 10:3655-3659.
Tucker & Grisshammer. Purification of a rat neurotensin receptor expressed in *Escherichia coli*. Biochem. J. 1996. 317(Pt. 3):891-899.
Urizar et al. An activation switch in the rhodopsin family of G protein-coupled receptors: The Thyrotropin receptor J. Biol Chem 2005 280(17):17135-17141.
Vagin & Teplyakov. MOLREP: an automated program for molecular replacement. J. Appl. Cryst. 1997. 30:1022-1025.
Vakser. Evaluation of GRAMM low-resolution docking methodology on hemagglutinin-antibody complex. Proteins, Suppl. 1997. 1:226-230.
Venturi & Hunte. Monoclonal antibodies for the structural analysis of the Na+/H+ antiporter NhaA from *Escherichia coli*. Biochimica et aBiophysica Acta. 2003. 1610:46-50.
Walters et al., Virtual screening—an overview. Drug Discovery Today. 1998. 3(4):160-178.
Wang. Basic Amino Acids at the C-Terminus of the Third Intracellular Loop Are Required for the Activation of Phospholipase C by Cholecystokinin-B Receptors. J. Neurochem. 1997. 68(4):1728-1735.
Warne et al., Structure of a β1-adrenergic G protein-coupled receptor. Nature. 2008. 454:486-491.
Warne et al., Expression and purification of truncated, non-glycosylated turkey beta-adrenergic receptors for crystallization. Biochim. Biophys. Acta. 2003. 1610:133-140.
Warne et al., The purification of G-protein coupled receptors for crystallization, Structural Biology of Membrane Proteins, Royal Society of Chemistry. 2006. 51-71.
Weber et al., A 1,536-Well cAMP Assay for Gs- and Gi-Coupled Receptors Using Enzyme Fragmentation Complementation. Assay Drug Dev. Technol. 2004. 2(1):39-49.
Weiβ & Grisshammer. Purification and characterization of the human adenosine A2a receptor functionally expressed in *Escherichia coli*. Eur. J. Biochem. 2002. 269:82-92.
Wess. Molecular Basis of Receptor/G-Protein-Coupling Selectivity. Pharmacol. Ther. 1998. 80:231-264.
White. The progress of membrane protein structure determination. Protein Science. 2004. 13:1948-1949.
Williams & Addona. The integration of SPR biosensors with mass spectrometry: possible applications for proteome analysis. Trends Biotechnol. 2000. 18(2):45-48.
Williams. Biotechnology match making: screening orphan ligands and receptors. Curr. Opin. Biotechnol. 2000. 11(1):42-46.
Winter & Milstein. Man-made antibodies. Nature. 1991. 349:293-299.
Winter et al., Surface binding affinity measurements from order transitions of lipid-membranecoated colloidal particles. Anal. Chem. 2006. 78:174-180.
Wurch et al., Chimeric Receptor Analysis of the Ketanserin Binding Site in the Human 5-Hydroxytryptamine1D Receptor: Importance of the Second Extracellular Loop and Fifth Transmembrane Domain in Antagonist Binding. Mol. Pharmacol. 1998. 54(6):1088-1096.
Wyckoff. Diffractometry. Methods in Enzymology. 1985. 114:330-386.
Yano et al., Phe576 Plays an Important Role in the Secondary Structure and Intracellular Signaling of the Human Luteinizing Hormone/Chorionic Gonadotropin Receptor. J. Clin. Endocrinol. Metabl. 1997. 82(8):2586-2591.
Yao et al., Coupling ligand structure to specific conformational switches in the β2-adrenoceptor. Nat. Chem. Biol. 2006. 2(8):417-422.
Yarden et al., The avian beta-adrenergic receptor: Primary structure and membrane topology. Proc. Natl. Acad. Sci. USA. 1986. 83:6795-6799.
Yohannan et al., The evolution of transmembrane helix kinks and the structural diversity of G protein-coupled receptors. PNAS. 2004. 101(4):959-963.
Yokogawa et al., Bead-linked Proteoliposomes: A Reconstitution Method for NMR Analyses of Membrane Protein-Ligand Interactions. J. Am. Chem. So. 2005. 127:12021-12027.
Zeitoun, O. et al., 2006, Mutagenesis within Helix 6 of the Human β1-Adrenergic Receptor Identifies Lysine324 as a Residue Involved in Imparting the High-Affinity Binding State of Agonists, Molecular Pharmacology, 70(3):838-850.
Zhang et al., Structure modelling of all identified G-protein coupled receptors in the human genome. PloS Computational Biology. 2006. 2(2):88-99.
Zhao et al. A homogeneous enzyme fragement complementation-based {beta}-Arrestin translocation assay for high-throughput screening of G-Protein-Coupled receptors: J. Biomol Screen 2008;13(8):737-747; Epub 2008.
Zheng et al., An efficient one-step site-directed and site-saturation mutagenesis protocol. Nucl. Acids Res. 2004. 32:e115.
Zhou & Bowie. Building a Thermostable Membrane Protein. J. Biol. Chem. 2000. 275:6975-6979.
Zurawski et al., A novel biosensor assay for screening peptide antagonism of the interaction between HIV-1 envelope, CD4 and membrane-embedded CCR5. Biopolymers. 2003. 71:388-389. Abstract P395.
U.S. Appl. No. 60/080,686, filed Apr. 3, 1998, Kuimelis et al.
International Search Report and Written Opinion for PCT/GB2008/000986 mailed Jan. 19, 2009.
International Preliminary Report on Patentability for PCT/GB2008/000986 mailed Jul. 6, 2009.
International Search Report and Written Opinion for PCT/GB2008/004032 mailed Aug. 19, 2009.
International Preliminary Report on Patentability for PCT/GB2008/004032 issued Jun. 8, 2010.
International Search Report and Written Opinion for PCT/GB2008/004223 mailed Aug. 19, 2009.
International Preliminary Report on Patentability for PCT/GB2008/004223 issued Jun. 22, 2010.
International Search Report and Written Opinion for PCT/GB2009/000310 mailed Jun. 23, 2009.
International Preliminary Report on Patentability for PCT/GB2009/000310 mailed Aug. 26, 2010.
International Search Report and Written Opinion for PCT/GB2008/000740 mailed Jul. 28, 2008.
International Preliminary Report on Patentability for PCT/GB2008/000740 issued Sep. 7, 2010.
International Search Report and Written Opinion for PCT/GB2010/001227 mailed Jun. 20, 2011.
International Preliminary Report on Patentability for PCT/GB2010/001227 mailed Jan. 12, 2012.
Office Action mailed Feb. 14, 2012 for U.S. Appl. No. 12/450,358.
[No author listed] Uniprot Database Accession No. P08482. 1988. Muscarinic acetylcholine receptor M1.
[No author listed] Stephen White Laboratory at UC Irvine. Available at http://blanco.biomol.uci.edu. Downloaded May 29, 2012.
[No author listed] IUPHAR database. G protein-coupled receptors. Available at http://www.iuphar-db.org/GPCR/ReceptorFamiliesForward. Downloaded Apr. 28, 2010.
[No author listed] The CCP4 suite: programs for protein crystallography. Collaborative Computational Project, No. 4. Acta Crystallogr. 1994. D50:760-763.
Abagyan & Totrov. High-throughput docking for lead generation. Curr. Opin. Chem. Biol. 2001. 5:375-382.

(56) References Cited

OTHER PUBLICATIONS

Abagyan et al., ICM—a new method for protein modelling and design. Applications to docking and structure prediction from the distorted native conformation. J. Comput. Chem. 1994. 15:488-506.

Adams et al., PHENIX: building new software for automated crystallographic structure determination. Acta Crystallogr. 2002. D58:1948-1954.

Afonine et al., The Phenix refinement framework. CCP Newsletter. 2005. Contribution 8.

Alexandrov et al., Microscale Fluorescent Thermal Stability Assay for Membrane Proteins; Structure; 2008;16:351-359.

Ali & Caffrey. Membrane Protein Crystallization in Lipidic Mesophases: Detergent Effects. Biophys. J. 2000.79:394-405.

Alkhatib et al., HIV coreceptors: from discovery and designation to new paradigms and promise. Eur. J. Med. Res. 2007 12(9):375-384.

Altschul & Gish. Local alignment statistics. Methods in Enzymology. 1996. 266:460-480.

Altschul et al., Basic local alignment search tool. J. Mol. Biol. 1990. 215:403-410.

Altschul et al., Gapped BLAST and PSI-BLAST: a new generation of protein database search programs. Nucl Acids Res. 1997 25:3389-3402.

Alves et al., Plasmon Resonance Methods in GPCR Signaling and Other Membrane Events. Curr. Prot. & Peptide Sci. 2005 6:293-312.

Artymiuk et al., Graph theoretic methods for the analysis of structural relationships in biological macromolecules. J Amer. Soc. Info. Sci Tech. 2005 56(5):518-528.

Avlani et al., Critical role for the second extracellular loop in the binding of both orthosteric and allosteric G protein-coupled receptor ligands. J Biol Chem. 2007. 282:25677-25686.

Babcook et al., A novel strategy for generating monoclonal antibodies from single, isolated lymphocytes producing antibodies of defined specificities. PNAS. 1996 93:7843-7848.

Baker. The selectivity of β-adrenoceptor antagonists at the human β1, β2 and β3 adrenoceptors. British J. Pharmacol. 2005. 144:317-322.

Bakker et al., Constitutively Active Mutants of the Histamine H1 Receptor Suggest a Conserved Hydrophobic Asparagine-Cage That Constrains the Activation of Class A G Protein-Coupled Receptors. Mol. Pharmacol. 2008. 73:94-103.

Balbes et al., A Perspective of Modern Methods in Computer-Aided Drug Design. Reviews in Computational Chemistry. 1994. 5:337-380.

Baldwin et al., An alpha-carbon template for the transmembrane helices in the rhodopsin family of G-proteincoupled receptors. J. Mol. Biol. 1997. 272:144-164.

Ballesteros & Weinstein. Integrated methods for the construction of three-dimensional models and computational probing of structure-function relations in G-protein coupled receptors. Methods in Neurosciences. 1995 Sealfon, S.C.and Conn, P.M. (eds.). Academic Press San Diego, CA 366-428.

Ballesteros et al., Activation of the beta 2-adrenergic receptor involves disruption of an ionic lock between the cytoplasmic ends of transmembrane segments 3 and 6. J. Biol. Chem. 2001. 276:29171-29177.

Ballesteros et al., Structural mimicry in GPCR: Implications of the high-resolution structure of rhodopsin for structure-function analysis of rhodopsin-like receptors. Mol. Pharmacology 60, 1-19, 2001.

Bamber et al., Yeast mitochondrial ADP ATP carriers are monomeric in detergents. PNAS. 2006 103:16224-16229.

Baneres et al., Molecular Characterization of a Purified 5-HT4 Receptor. J. Biol. Chem. 2005. 208:20253-20260.

Baranski et al., C5a Receptor Activation. J. Biol. Chem. 1999. 274(22):15757-15765.

Barbas et al., Assembly of combinatorial antibody libraries on phage surfaces: The gene III site. PNAS. 1991 88:7978-7982.

Baroni et al., A Common Reference Framework for Analyzing/Comparing Proteins and Ligands. Fingerprints for Ligands and Proteins (FLAP): Theory and Application. J. Chem Inf. Mod. 2007. 47:279-294.

Barroso S. et al., 2000, Identification of Residues Involved in Neurotensin Binding and Modeling of the Agonist Binding Site in Neurotensin Receptor 1, Journal of Biological Chemistry, 275(1):328-336.

Barroso S. et al., 2002, Constitutive activation of the neurotensin receptor 1 by mutation of Phe358 in Helix seven, British Journal of Pharmacology, 135:997-1002.

Barry et al., Quantitative protein profiling using antibody arrays. Proteomics. 2004 4:3717-3726.

Bartlett et al., CAVEAT: A Program to Facilitate the Structure-Derived Design of Biologically Active Molecules. Molecular Recognition: Chemical and Biological Problems, 1989. S. M. Roberts, Editor, Royal Society of Chemistry. 78:182-196.

Bee et al., 2007, Functional analysis of transmembrane domain 2 of the M1 muscarinic acetylocholine receptor, J. Biol. Chem. 282(44):32471-32479.

Behr et al., Novel mutants of the human β1-adrenergic receptor reveal amino acids relevant for receptor activation. J. Biol. Chem. 2006. 281(26):18120-18125.

Berchiche et al., Direct Assessment of CXCR4 Mutant Conformations Reveals Complex Link between Receptor Structure and G(alpha)(i) Activation. J. Biol. Chem. 2007. 282(8):5111-5115.

Besenicar et al., Surface plasmon resonance in protein-membrane interactions. Chem. Phys. Lipids. 2006 141:169-178.

Black. Drugs from Emasculated Hormones: The Principle of Syntopic Antagonism (Nobel Lecture). Angew Chem. Int. Edit. 1989. 28:886-894.

Blundell et al., Knowledge-based prediction of protein structures and the design of novel molecules. Nature. 1987. 326:347-352.

Blundell et al., Knowledge-based protein modelling and design; 18th Sir Hans Krebs Lecture Eur. J. Biochem. 1988. 173:513-520.

Stability of mutant M1 mAChRs
in 1 % Octyl Glucoside
29.10.2004

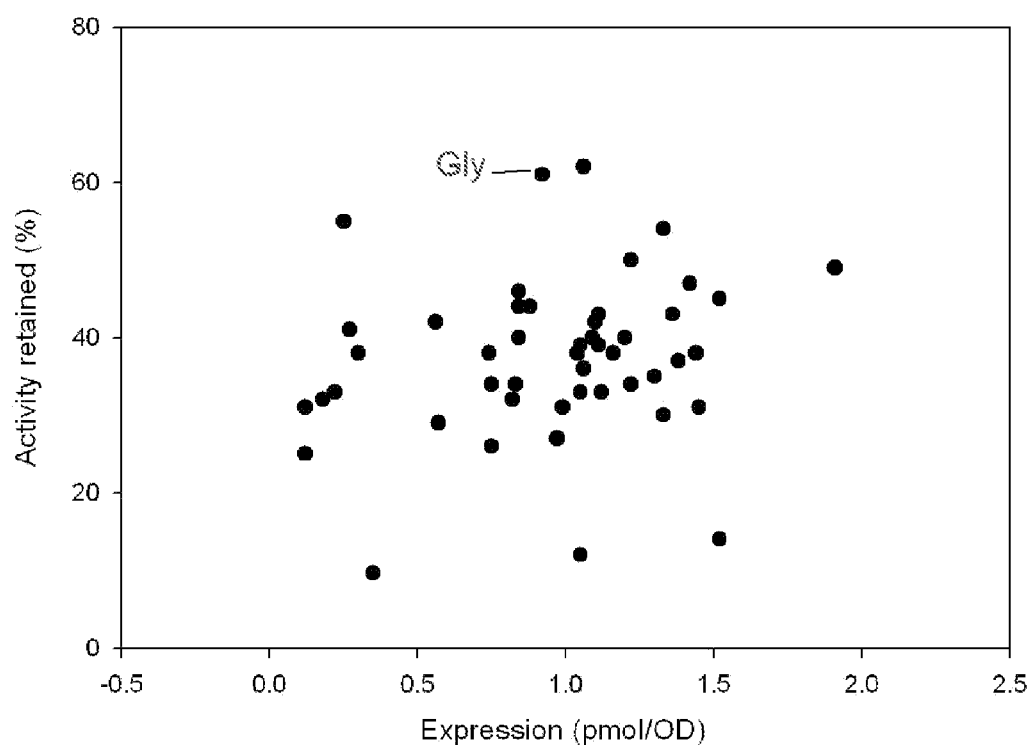

Stability solubilised in 1 % βOG

TM6 and TM7 mutants:
Stability solubilised in 1% βOG

A.

B.

C.

MUTANT PROTEINS AND METHODS FOR SELECTING THEM

RELATED APPLICATIONS

This application is a national stage filing under 35 U.S.C. §371 of international application PCT/GB2009/000310, filed Feb. 5, 2008, which was published under PCT Article 21(2) in English, the disclosure of which is incorporated in its entirety herein by reference. This application claims the benefit under 35 U.S.C. §119(a)-(d) of United Kingdom Application No. 0802474.7, filed Feb. 11, 2008, the entire disclosure of which is incorporated herein by reference.

The present invention relates to mutant membrane proteins and methods for selecting those with increased stability. In particular, it relates to the selection and preparation of mutant membrane proteins which have increased stability under a particular condition compared to their respective parent proteins. Such proteins are more likely to be crystallisable, and hence amenable to structure determination, than the parent proteins. They are also useful for drug discovery and development studies.

Over the past 20 years the rate of determination of membrane protein structures has gradually increased, but most success has been in crystallising membrane proteins from bacteria rather than from eukaryotes [1]. Bacterial membrane proteins have been easier to overexpress using standard techniques in *Escherichia coli* than eukaryotic membrane proteins [2,3] and the bacterial proteins are sometimes far more stable in detergent, detergent-stability being an essential prerequisite to purification and crystallisation. Genome sequencing projects have also allowed the cloning and expression of many homologues of a specific transporter or ion channel, which also greatly improves the chances of success during crystallisation. However, out of the 120 different membrane protein structures that have been solved to date, there are only seven structures of mammalian integral membrane proteins (http://blanco.biomol.uci.edu/); five of these membrane proteins were purified from natural sources and are stable in detergent solutions. Apart from the difficulties in overexpressing eukaryotic membrane proteins, they often have poor stability in detergent solutions, which severely restricts the range of crystallisation conditions that can be explored without their immediate denaturation or precipitation. Ideally, membrane proteins should be stable for many days in any given detergent solution, but the detergents that are best suited to growing diffraction-quality crystals tend to be the most destabilising detergents ie those with short aliphatic chains and small or charged head groups. It is also the structures of human membrane proteins that we would like to solve, because these are required to help the development of therapeutic agents by the pharmaceutical industry; often there are substantial differences in the pharmacology of receptors, channels and transporters from different mammals, whilst yeast and bacterial genomes may not include any homologous proteins. There is thus an overwhelming need to develop a generic strategy that will allow the production of detergent-stable eukaryotic integral membrane proteins for crystallisation and structure determination and potentially for other purposes such as drug screening, bioassay and biosensor applications.

Membrane proteins have evolved to be sufficiently stable in the membrane to ensure cell viability, but they have not evolved to be stable in detergent solution, suggesting that membrane proteins could be artificially evolved and detergent-stable mutants isolated [4]. This was subsequently demonstrated for two bacterial proteins, diacylglycerol kinase (DGK) [5,6] and bacteriorhodopsin [7]. Random mutagenesis of DGK identified specific point mutations that increased thermostability and, when combined, the effect was additive so that the optimally stable mutant had a half-life of 35 minutes at 80° C. compared with a half-life of 6 minutes at 55° C. for the native protein [6]. It was shown that the trimer of the detergent-resistant DGK mutant had become stable in SDS and it is thus likely that stabilisation of the oligomeric state played a significant role in thermostabilisation. Although the aim of the mutagenesis was to produce a membrane protein suitable for crystallisation, the structure of DGK has yet to be determined and there have been no reports of successful crystallization. A further study on bacteriorhodopsin by cysteine-scanning mutagenesis along helix B demonstrated that it was not possible to predict which amino acid residues would lead to thermostability upon mutation nor, when studied in the context of the structure, was it clear why thermostabilisation had occurred [7].

One example of membrane proteins are GPCRs. GPCRs control many physiological processes and are the targets of many effective drugs. Thus, they are of considerable pharmacological importance. A list of GPCRs is given in Foord et al (2005) *Pharmacol Rev.* 57, 279-288, which is incorporated herein by reference. GPCRs are generally unstable when isolated, and despite considerable efforts, it has not been possible to crystallise any except bovine rhodopsin, which naturally is exceptionally stable.

GPCRs are druggable targets, and reference is made particularly to Overington et al (2006) *Nature Rev. Drug Discovery* 5, 993-996 which indicates that over a quarter of present drugs have a GPCR as a target.

GPCRs are thought to exist in multiple distinct conformations which are associated with different pharmacological classes of ligand such as agonists and antagonists, and to cycle between these conformations in order to function (Kenakin T. (1997) *Ann N Y Acad Sci* 812, 116-125).

The listing or discussion of an apparently prior-published document in this specification should not necessarily be taken as an acknowledgement that the document is part of the state of the art or is common general knowledge.

The low stability (e.g. thermostability) of fully solubilised membrane proteins makes obtaining mutant membrane proteins with increased stability difficult. The range of conditions that can be explored without their immediate denaturation or precipitation when removed from their native membrane environment is severely restricted. One way of overcoming this is to provide the mutant proteins in their native membrane environment, assuming that any increase in stability also translates to an increase in stability out of the membrane. However, this is generally not experimentally tractable. Instead, we have developed a methodology for obtaining mutant membrane proteins with increased stability, whereby a mutant protein is provided in the form of a membrane composition destabilised by the addition of a destabilising agent, for example a detergent. In this way, proteins which are intrinsically unstable in a solubilised state can be easily manipulated and their stability increased.

Accordingly, a first aspect of the invention provides a method for selecting a membrane protein with increased stability, the method comprising:

a) providing one or more mutants of a parent membrane protein in a membrane-containing composition, wherein the one or more mutants are exposed to an amount of a membrane destabilising agent which is effective to destabilise the parent membrane protein in-situ, b) determining whether the or each mutant membrane protein has increased stability with respect to its structure and/or a biological activity, compared to the stability of the parent membrane protein with respect to its structure and/or the same biological activity, and c) selecting the one or more mutants which have increased stability compared to the stability of the parent membrane protein.

It will be appreciated that while the method of the invention has been exemplified with GPCRs, the method is equally applicable to any membrane protein, especially a membrane protein that has a low stability when removed from its native membrane environment.

By "membrane protein" we mean a protein that is attached to or associated with a membrane of a cell or organelle. Preferably, the membrane protein is an integral membrane protein that is permanently integrated into the membrane and can only be removed using detergents, non-polar solvents or denaturing agents that physically disrupt the lipid bilayer.

Examples of suitable membrane proteins include receptors such as GPCRs, the T-cell receptor complex and growth factor receptors; transmembrane ion channels such as ligand-gated and voltage gated channels; transmembrane transporters such as neurotransmitter transporters; enzymes; carrier proteins; and ion pumps.

The amino acid sequences (and the nucleotide sequences of the cDNAs which encode them) of many membrane proteins are readily available, for example by reference to Gen-Bank. For example, Foord et al supra gives the human gene symbols and human, mouse and rat gene IDs from Entrez Gene (ncbi.nlm.nih/gov/entrez) for GPCRS. It should be noted, also, that because the sequence of the human genome is substantially complete, the amino acid sequences of human membrane proteins can be deduced therefrom.

Although the membrane protein may be derived from any source, it is particularly preferred if it is from a eukaryotic source. It is particularly preferred if it is derived from a vertebrate source such as a mammal or a bird. It is particularly preferred if the membrane protein is derived from rat, mouse, rabbit or dog or non-human primate or man, or from chicken or turkey. For the avoidance of doubt, we include within the meaning of "derived from" that a cDNA or gene was originally obtained using genetic material from the source, but that the protein may be expressed in any host cell subsequently. Thus, it will be plain that a eukaryotic membrane protein (such as an avian or mammalian membrane protein) may be expressed in a prokaryotic host cell, such as *E. coli*, but be considered to be avian- or mammalian-derived, as the case may be.

In one embodiment, the membrane protein is a GPCR.

Suitable GPCRs for use in the practice of the invention include, but are not limited to β-adrenergic receptor, adenosine receptor, in particular adenosine $A_{2a}$ receptor, neurotensin receptor (NTR) and muscarinic receptor. Other suitable GPCRs are well known in the art and include those listed in Hopkins & Groom supra. In addition, the International Union of Pharmacology produce a list of GPCRs (Foord et al (2005) *Pharmacol. Rev.* 57, 279-288, incorporated herein by reference and this list is periodically updated at http://www.i-uphar-db.org/GPCR/ReceptorFamiliesForward). It will be noted that GPCRs are divided into different classes, principally based on their amino acid sequence similarities. They are also divided into families by reference to the natural ligands to which they bind. All GPCRs are included in the scope of the invention.

In some instances, the GPCR may be composed of more than one different subunit. For example, the calcitonin gene-related peptide receptor requires the binding of a single transmembrane helix protein (RAMP1) to acquire its physiological ligand binding characteristics. Effector, accessory, auxiliary or GPCR-interacting proteins which combine with the GPCR to form or modulate a functional complex are well known in the art and include, for example, receptor kinases, G-proteins and arrestins (Bockaert et al (2004) *Curr Opinion Drug Discov and Dev* 7, 649-657).

The mutants of the parent membrane protein may be produced in any suitable way and provided in any suitable form. Thus, for example, a series of specific mutants of the parent protein may be made in which each amino acid residue in all or a part of the parent protein is independently changed to another amino acid residue. For example, it may be convenient to make mutations in those parts of the protein which are predicted to be membrane spanning. For example, the three-dimensional structures of some membrane proteins including rhodopsin and beta-adrenergic receptor are known (Li et al (2004) *J Mol Biol* 343, 1409-1438; Palczewski et al (2000) *Science* 289, 739-745; Rasmussen et al (2007) *Nature* 15; 383-387; Cherezov et al (2007) *Science*, 318:1258-65; Rosenbaum et al (2007) *Science* 318:1266-1273), and it is possible to model certain GPCRs using these structures. Thus, conveniently, parts of the membrane protein to mutate may be based on modelling. Similarly, computer programs are available which model transmembrane regions of membrane proteins based on hydrophobicity (Kyle & Dolittle (1982) *J. Mol. Biol.* 157, 105-132), and use can be made of such models when selecting parts of the protein to mutate. Conventional site-directed mutagenesis may be employed, or polymerase chain reaction-based procedures well known in the art may be used. It is possible, but less desirable, to use ribosome display methods in the selection of the mutant protein.

Typically, each selected amino acid is replaced by Ala (ie Ala-scanning mutagenesis), although it may be replaced by any other amino acid. If the selected amino acid is Ala, it may conveniently be replaced by Leu. Alternatively, the amino acid may be replaced by Gly (ie Gly-scanning mutagenesis), which may allow a closer packing of neighbouring helices that may lock the protein in a particular conformation. If the selected amino acid is Gly, it may conveniently be replaced by Ala.

Although the amino acid used to replace the given amino acid at a particular position is typically a naturally occurring amino acid, typically an "encodeable" amino acid, it may be a non-natural amino acid (in which case the protein is typically made by chemical synthesis or by use of non-natural amino-acyl tRNAs). An "encodeable" amino acid is one which is incorporated into a polypeptide by translation of mRNA. It is also possible to create non-natural amino acids or introduce non-peptide linkages at a given position by covalent chemical modification, for example by post-translational treatment of the protein or semisynthesis. These post-translational modifications may be natural, such as phosphorylation, glycosylation or palmitoylation, or synthetic or biosynthetic.

Alternatively, the mutants may be produced by a random mutagenesis procedure, which may be of the whole protein or of a selected portion thereof. Random mutagenesis procedures are well known in the art.

Conveniently, the mutant membrane protein has one replaced amino acid compared to the parent protein (ie it is mutated at one amino acid position). In this way, the contribution to stability of a single amino acid replacement may be assessed. However, the mutant membrane protein assayed for stability may have more than one replaced amino acid compared to the parent protein, such as 2 or 3 or 4 or 5 or 6 replacements.

As is discussed in more detail below, combinations of mutations may be made based on the results of the selection method. It has been found that in some specific cases combining mutations in a single mutant protein leads to a further increase in stability. Thus, it will be appreciated that the method of the invention can be used in an iterative way by, for example, carrying it out to identify single mutations which increase stability, combining those mutations in a single mutant membrane protein which is the membrane protein then provided in part (a) of the method. Thus, multiply-mutated mutant proteins can be selected using the method.

The parent membrane protein need not be the naturally occurring protein. Conveniently, it may be an engineered version which is capable of expression in a suitable host organism, such as *Escherichia coli*. The parent GPCR may be a truncated form of the naturally occurring protein (truncated at either or both ends), or it may be a fusion, either to the naturally occurring protein or to a fragment thereof. Alternatively or additionally, the parent membrane protein, compared to a naturally-occurring membrane protein, may be modified in order to improve, for example, solubility, proteolytic stability (eg by truncation, deletion of loops, mutation of glycosylation sites or mutation of reactive amino acid side chains such as cysteine). In any event, the parent protein is a protein which retains a functional activity of the naturally occurring protein. For example, where the naturally occurring protein binds a ligand, the parent protein is able to bind to the ligand which is known to bind the naturally occurring membrane protein. Conveniently, the membrane protein is one which, on addition of an appropriate ligand, can affect any one or more of the downstream activities resulting from binding that ligand. For example, where the membrane protein is a GPCR, the parent GPCR is one which, on addition of an appropriate ligand, can affect any one or more of the downstream activities which are commonly known to be affected by G-protein activation.

However, it will be appreciated that the stability of the mutant is to be compared to a parent in order to be able to assess an increase in stability.

By "membrane-containing" composition, we include a cellular composition, that is, a composition comprising whole cells, including a cell organelle or membrane-containing extract or fraction thereof. Also included is a lipid monolayer, a lipid bilayer, a bead-linked lipid particle or a proteoliposome. It will be appreciated that the "membrane-containing" composition may comprise natural and/or synthetic lipids.

By "membrane destabilising agent" we include any agent which is capable of shifting the equilibrium of a population of membrane proteins from the folded native state to the unfolded state. In this way, the proportion of proteins existing in the unfolded state is increased and the proportion existing in the folded native state is decreased.

By "population" we include a plurality of the same specific type of protein, as opposed to a mixture of different proteins. For example, the population may comprise at least 2, 5, 10, 50, 100, 200, 500, 1000, 5000, 10000, 100000, $10^6$, $10^7$, $10^8$, $10^9$, $10^{10}$, $10^{11}$, $10^{12}$, $10^{13}$ or $10^{14}$ protein molecules. Preferably, the population may comprise between $10^9$ and $10^{12}$ protein molecules.

The destabilising agent may be a detergent, including for example, detergents that are of interest for subsequent crystallisation studies, for instance short chain-length detergents with a high CMC, such as C8-glucoside, C8-thioglucoside, C9-glucoside, C8-maltoside, C8-thiomaltoside, C9-maltoside, C9-thiomaltoside, Cymal 5, C8E5, or lauryl dimethylamine oxide. Short chain-length detergents are more likely to allow the formation of a 3-dimensional crystal lattice, and are easier to remove from receptor preparations by dialysis, or other means than are long chain-length detergents with low CMCs. Such detergents also have an extended working concentration range in destabilization experiments, because detergents, generally, do not solubilize membranes when present at concentrations below their CMCs.

It will be appreciated that any other amphiphilic molecule may also be used as a destabilising agent. For example, the destabilising agent may be any of amphipols, amphiphilic peptides such as mellitin, proteins such as apolipoproteins and their derivatives, organic solvents such as trifluoroethanol, dimethylformide, dimethylsulphoxide and chloroform/methanol mixtures, urea, a cylcodextrin, poly-ene antibiotics, guanidine hydrogenchloride, local anaesthetics and drugs such as procaine and chlorpromazine, polyols such as butane diol and heptane triol, alcohols such as propanol, isopropanol and benzyl alcohol and enzymes that perturb membrane structures such as phospholipase A.

When in situ, i.e. disposed normally within a membrane, a population of membrane proteins will exist in a "stabilised condition". In this condition, the proteins adopt their folded native structure and exhibit a biological activity, for example a binding activity, a signalling pathway modulation activity, a transmembrane transporting activity or an enzyme activity that can be measured. The equilibrium between folded native and unfolded states is shifted towards the folded native state (FIG. 8).

Figure 8:
Figure 8:
Figure 8:

Upon increasing exposure to a destabilising agent as described above, for example a detergent, the equilibrium shifts further towards the unfolded state and an increasingly higher proportion of the membrane proteins exist in the unfolded state (FIG. 8). This change in structure from a folded to an unfolded state leads to a detectable change in the structure of the membrane protein population. Moreover, this change in structure may lead to a detectable decrease in a biological activity of the membrane protein population. We propose that this shift in equilibrium reflects the lowering of the free energy barrier separating the folded native state from the unfolded state, as a result of exposure to the membrane destabilising agent, which acts to destabilise the lipid:membrane protein association.

The point at which there is no further significant structural perturbation (e.g. all proteins are in the unfolded state) and/or a particular biological activity does not decrease significantly upon increased exposure to the destabilising agent, is referred to herein as a "fully destabilised condition". In this condition, the equilibrium between native and unfolded states is shifted towards the unfolded state (FIG. 8). Typically, the protein will be inactive in the fully destabilised condition.

Between the "stabilised condition" and the "fully destabilised condition" we define herein an "in-situ destabilised condition". In this condition, while not all proteins are in the unfolded state, the structure of the membrane proteins, while still residing in-situ in the original membrane environment, is detectably perturbed compared to the structure of the membrane proteins in the "stabilised condition" (i.e. the native-folded structure). Thus, in the in-situ destabilised condition, the native structure of the membrane proteins may be perturbed but not fully unfolded and/or the proportion of fully unfolded protein may be increased. Furthermore, while the population of membrane proteins will exhibit some of a particular biological activity in the "in-situ destabilised condition", this may be at a reduced level compared to the same activity of the population in the "stabilised condition" (e.g. if the change in structure has led to a change in the particular activity).

The inventors have reasoned that this in-situ destabilised condition presents an opportunity for selecting one or more mutant membrane proteins which have increased stability under a particular condition compared to their respective parent proteins. In particular, the use of such a destabilised condition offers an experimentally tractable means of selecting mutants with increased stability that could not otherwise be obtained because of their instability in a fully solubilised form.

Typically, the destabilising agent is titrated into the membrane-containing composition, and the change in structure and/or the level of a biological activity, of the membrane protein population, detected to determine the concentration of destabilising agent necessary to destabilise the parent protein in situ.

Thus in one embodiment, an amount of a destabilising agent "effective to destabilise the parent membrane protein in-situ" means an amount which brings about a significant perturbation in the structure of the membrane protein population, over a given period of time, compared to the structure in the absence of the destabilising agent, without all proteins of the population existing in the unfolded state. For example, it will be appreciated that following a given period of time, for example 10 min, 20 min, 30 min, 40 min, 50 min, 1 hour, 2 hours, 3 hours, 4 hours, 5 hours, 6 hours, 7 hours, 8 hours, 9 hours, 10 hours, 11 hours, 12 hours, 13 hours, 14 hours or 15 hours from exposure to the destabilising agent, the protein population may be assayed for structural perturbation. Typically, the time will be between 1 hour and 10 hours. The optimum time is determined by measuring the structure of a population of the membrane protein in the membrane composition as a function of time in the presence and absence of a chosen concentration of destabilising agent. The optimum time is that which gives a significant perturbation in the structure of the membrane protein population compared to the structure in the absence of the destabilising agent.

By a significant perturbation in the structure of a membrane protein population, we mean a perturbation which, when assessed relative to the statistical variation of the measurements used to detect the perturbation, would arise by chance in less than 1 in 10 measurements, more preferably 1 in 20 measurements and even more preferably 1 in 50 or 1 in 100 measurements.

Various methods to probe protein structure are known in the art and any suitable method may be used. For example, structural perturbations may be assayed by probing conformation directly e.g. with covalently attached fluorescent labels or esr spin labels, or by measuring the accessibility of native or deliberately introduced amino acid side chains within the protein population (Hubbell, W. L. et al., Adv. Protein. Chem. 63, 243-290 (2003); Baneres, J. L. et. al., J. Biol. Chem. 280, 20253-20260 (2005); Kobilka, B. K. and Deupi, X. Trends. Pharmacol. Sci. 28, 397-406 (2007)). For example, changes in fluorescence spectra, can be a sensitive indicator of protein unfolding, either by use of intrinsic tryptophan fluorescence or the use of extrinsic fluorescent probes such as 1-anilino-8-naphthalenesulfonate (ANS), for example as implemented in the Thermofluor™ method (Mezzasalma et al, J Biomol Screening, 2007, April; 12(3):418-428). Proteolytic stability, deuterium/hydrogen exchange measured by mass spectrometry or nuclear magnetic resonance spectroscopy, blue native gels, capillary zone electrophoresis, circular dichroism (CD) or linear dichroism (LD) spectra and light scattering may also be used to measure structural perturbation by loss of signals associated with secondary or tertiary structure.

While a detectable change in the structure of the membrane protein population does not necessarily lead to a change in the level of a biological activity of that population, where possible, it is preferred to measure biological activity in order to determine the amount of a destabilising agent necessary to destabilise a membrane protein in-situ.

Thus, in a preferred embodiment, an amount of a destabilising agent "effective to destabilise the parent membrane protein in-situ" means an amount Which brings about a significant reduction in, for example less than 100%, but not loss of, a biological activity of the membrane protein population, over a given period of time, compared to the level of the same activity in the absence of the destabilising agent. For example, it will be appreciated that following a given period of time, for example 10 min, 20 min, 30 min, 40 min, 50 min, 1 hour, 2 hours, 3 hours, 4 hours, 5 hours, 6 hours, 7 hours, 8 hours, 9 hours, 10 hours, 11 hours, 12 hours, 13 hours, 14 hours or 15 hours from exposure to the destabilising agent, the protein population may be assayed for reduction in activity. Typically, the time will be between 1 hour and 10 hours. The optimum time is determined by measuring a biological activity of a population of the membrane protein in the membrane composition as a function of time in the presence and absence of a chosen concentration of destabilising agent. The optimum time is that which gives a suitable reduction in the biological activity compared to the activity in the absence of the destabilising agent.

Preferably, the reduction in the biological activity over a given period of time is to 90-10% or 70-30%, more preferably, 60-40% and most preferably 50% of the level of the same activity when measured in the absence of the destabilising agent.

Depending upon the biological activity, it will be appreciated that the activity of the membrane protein may be measured using any suitable method known in the art.

By 'binding activity', we include binding to any binding partner that is known to bind to the membrane protein. For example, the binding partner may be a ligand, for example one which causes the membrane protein to reside in a particular conformation, or it may be an antibody, for example a conformational-specific antibody. Binding activity can be assessed using routine binding assays known in the art. Conveniently, the binding partner is detectably labelled, eg radiolabelled or fluorescently labelled. Alternatively, binding can be assessed by measuring the amount of unbound binding partner using a secondary detection system, for example an antibody or other high affinity binding partner covalently linked to a detectable moiety, for example an enzyme which may be used in a colorimetric assay (such as alkaline phosphatase or horseradish peroxidase). Biophysical techniques such as patch clamping, fluorescence correlation spectroscopy, fluorescence resonance energy transfer and analytical ultracentrifugation may also be used (as described in New, R. C., *Liposomes: a practical approach.* 1st ed.; Oxford University Press: Oxford, 1990, and Graham, J. M.; Higgins, J. A., *Membrane Analysis.* Springer-Verlag: New York, 1997.)

An example of assessing binding activity in order to determine the amount of destabilising agent necessary is provided in Example 1, which demonstrates the method of the invention in relation to the muscarinic M1 acetylcholine receptor (M1 mAChR). Specifically, it was found that for the muscarinic receptor, a concentration of 0.82% of the destabilising agent beta octyl glucoside was necessary to provide an in-situ destabilised state. This concentration was determined by analysing wild-type M1 mAChRs expressed in the inner cell membranes of intact *E. Coli* strain BL21 cells. The cells were pre-labelled with the radiolabelled antagonist 3H—N-methyl scopolamine and resuspended to a pre-determined cell density (Absorbance at 600 nm=2.0) in a chosen buffer (in this case 50 mM sodium phosphate, 1 mM EDTA, pH 7.5). A typical concentration of radiolabelled 3H—N-methyl scopolamine specifically bound to wild-type M1 mAChRs was $2 \times 10^{-12}$ moles per ml of cell suspension. The wild-type M1 mAChRs were titrated by the addition of increasing concentrations of beta octyl glucoside dissolved in the same buffer for different times (e.g. 1 h, 2 h, 3 h, 5 h, 15 h) and at different temperatures (e.g. 4° C., 15° C.). The loss of specifically-bound radioligand was then measured after recovering the cells by centrifugation (15000×g, 15 min.). In the example, the centrifugation step was performed on duplicate 1 ml aliquots of the cells. The experiment was repeated 3 times. 0.82% beta octyl glucoside gave a 50% loss of binding activity in 3 hours at 4° C. when compared to control samples of the cell suspension prepared with buffer only. While 0.82% beta octyl glucoside gave a 50% loss of binding activity and thus would give rise to an "in-situ destabilised" state, the inventors appreciate that both lower (e.g. 0.6% and 0.7%) and higher (e.g. 0.9% and 1%) concentrations may be used. It will be appreciated that the cell density, detergent concentration and other parameters of the assay may be varied to adjust the loss of activity as appropriate.

Where the biological activity is a signalling pathway modulating activity, the activity can be assessed by any suitable assay for the particular signalling pathway. For example, the activity may be measured by using a reporter gene to measure the activity of the particular signalling pathway. By a reporter gene we include genes which encode a reporter protein whose activity may easily be assayed, for example β-galactosidase, chloramphenicol acetyl transferase (CAT) gene, luciferase or Green Fluorescent Protein (see, for example, Tan et at, 1996 *EMBO J* 15(17): 4629-42). Several techniques are available in the art to detect and measure expression of a reporter gene which would be suitable for use in the present invention. Many of these are available in kits both for determining expression in vitro and in vivo. Alternatively, signalling may be assayed by the analysis of downstream targets. For example, a particular protein whose expression is known to be under the control of a specific signalling pathway may be quantified. Protein levels in biological samples can be determined using any suitable method known in the art. For example, protein concentration can be studied by a range of antibody based methods including immunoassays, such as ELISAs, western blotting and radio-immunoassays Where the biological activity is a transmembrane transport activity, the activity can be assessed by uptake of fluorescent or radiolabelled tracers as is well known in the art or by using magnetic resonance imaging techniques.

Where the biological activity is an enzymatic activity, the activity can be assessed by any suitable enzyme assay known in the art. Enzyme assays typically measure either the consumption of substrate or production of product over time. It is appreciated that a large number of methods exist for determining the concentrations of substrates and products such that many enzymes can be assayed in several different ways as is well known in the art.

The increased stability of a mutant membrane protein is conveniently measured by a higher biological activity of the mutant membrane protein compared to the parent membrane protein when in the in-situ destabilised state. When the parent protein manifests, for example, 50% of a biological activity in the in-situ destabilised state compared to the activity in the stabilised condition, typically, the mutant membrane protein with increased stability relative to the parent protein, will have at least 5%, 10%, 15%, 20%, 25%, 30%, 35%, 40%, 45% or 50% more biological activity than the parent protein when in the in-situ destabilised state, and more preferably at least 60%, 70%, 80%, 90% or 100% more activity, and yet more preferably at least 150% or 200% more activity.

Typically, a mutant membrane protein is selected that has increased stability with respect to any one biological activity of the membrane protein such as binding activity, a signalling pathway modulation activity, a transmembrane transporting activity or an enzyme activity.

Although it is convenient to measure the stability of the parent and mutant GPCR by assaying a biological activity, other methods are known in the art. In particular, it will be appreciated that the structures of the parent and mutant GPCRs may be probed directly in the in-situ destabilised state, for example as described above. For example, a mutant membrane protein that has a structure that is more similar to the folded-native state than the parent protein is to the folded-native state, may be selected.

It will be appreciated that the comparison of stability of the mutant is made by reference to the parent molecule under the same conditions.

It is believed that having increased stability with respect to structure and/or a particular biological activity in the in-situ destabilised state may also be a guide to the stability to other denaturants or denaturing conditions including heat, a detergent, a chaotropic agent and an extreme of pH.

Thus in a further embodiment, it is determined whether the selected mutant protein has an increased stability to any one or more of heat, a detergent, a chaotropic agent and an extreme of pH.

In relation to an increased stability to heat (ie thermostability), this can readily be determined by measuring ligand binding or by using spectroscopic methods such as fluorescence, CD or light scattering at a particular temperature. Typically, when the membrane protein binds to a ligand, the ability of the membrane protein to bind that ligand at a particular temperature may be used to determine thermostability of the mutant. It may be convenient to determine a "quasi $T_m$" ie the temperature at which 50% of the receptor is inactivated under stated conditions after incubation for a given period of time (eg 30 minutes). Mutant membrane proteins of higher thermostability have an increased quasi Tm compared to their parents.

In relation to an increased stability to a detergent or to a chaotrope, typically the membrane protein is incubated for a defined time in the presence of a test detergent or a test chaotropic agent and the stability is determined using, for example, ligand binding or a spectroscopic method as discussed above.

In relation to an extreme of pH, a typical test pH would be chosen (eg in the range 4.5 to 5.5 (low pH) or in the range 8.5 to 9.5 (high pH)).

Because relatively harsh detergents are used during crystallisation procedures, it is preferred that the mutant membrane protein is stable in the presence of such detergents. The order of "harshness" of certain detergents is DDM, $C_{11} \rightarrow C_{10} \rightarrow C_9 \rightarrow C_8$ maltoside or glucoside, lauryldimethylamine oxide (LDAO) and SDS. It is particularly preferred if the mutant membrane protein is more stable to any of $C_9$ maltoside or glucoside, $C_8$ maltoside or glucoside, LDAO and SDS, and so it is preferred that these detergents are used in the later stages of stability testing.

Because of its ease of determination, it is preferred that thermostability is determined, and those mutants which have an increased thermostability compared to the parent protein with respect to the selected condition are chosen. It will be appreciated that heat is acting as the denaturant, and this can readily be removed by cooling the sample, for example by placing on ice.

It will be appreciated that mutants displaying increased stability in the in-situ destabilised state can be selected which are stabilised sufficiently to permit full solubilisation in a particular solubilising agent. In this way, it is possible to select mutants which could not otherwise be obtained because of their instability in the particular solubilising agent, which agent may be particularly preferred for subsequent mutant GPCR crystallisation or other methods.

It is also appreciated that having obtained a mutant which is sufficiently stable to permit full solubilisation, its stability can be further increased by introducing additional mutations when in a solubilised state.

Examples of the above in-situ destabilisation approach are described below in Examples 1-3 in relation to the muscarinic M1 acetylcholine receptor (M1 mAChR).

The examples show that certain mutations at positions 65, 151, 145, 383, 384 and 399 improve the thermostability of M1 mAChRs labelled in the inner membranes of intact *E. coli* cells with the antagonist NMS (N-methyl scopolamine) in the presence of the short chain-length detergent beta-octyl glucoside (BOG), and that when fully solubilised such mutant receptors continue to be more stable than wild type receptors in other detergents. There is also demonstration of additivity of mutations. It is also shown that co-addition of allosteric antagonist (strychnine) to orthosteric antagonist (NMS) improves stability in detergent, which may be useful in a selection procedure.

A second aspect of the invention provides a method for preparing a mutant membrane protein, the method comprising (a) carrying out the method of the first aspect of the invention, (b) identifying the position or positions of the mutated amino acid residue or residues in the mutant membrane protein or proteins which have been selected for increased stability, and (c) synthesising a mutant membrane protein which contains a mutation at one or more of the positions identified.

As can be seen in the Examples, surprisingly, changes to a single amino acid within a membrane protein may increase the stability of the protein compared to the parent protein with respect to a particular condition in which the protein resides in a particular conformation. Thus, in one embodiment of the method of the second aspect of the invention, a single amino acid residue of the parent protein is changed in the mutant protein. Typically, the amino acid residue is changed to the amino acid residue found in the mutant tested in the method of the first aspect of the invention. However, it may be replaced by any other amino acid residue, such as any naturally-occurring amino acid residue (in particular, a "codeable" amino acid residue) or a non-natural amino acid. Generally, for convenience, the amino acid residue is replaced with one of the 19 other codeable amino acids. Preferably, it is the replaced amino acid residue which is present in the mutant selected in the first aspect of the invention.

Also as can be seen in the Examples, a further increase in stability may be obtained by replacing more than one of the amino acids of the parent protein. Typically, each of the amino acids replaced is one which has been identified using the method of the first aspect of the invention. Typically, each amino acid identified is replaced by the amino acid present in the mutant protein although, as noted above, it may be replaced with any other amino acid.

Typically, the mutant membrane protein contains, compared to the parent protein, from 1 to 10 replaced amino acids, preferably from 1 to 8, typically from 2 to 6 such as 2, 3, 4, 5 or 6 replaced amino acids.

It will be appreciated that the multiple mutants may be subject to the selection method of the first aspect of the invention. In other words, multiple mutants may be provided in step (a) of the method of the first aspect of the invention. It will be appreciated that by the first and/or second aspect of the invention multiple mutagenised membrane proteins may be made, whose conformation has been selected to create a very stable multiple point mutant protein.

The mutant membrane proteins may be prepared by any suitable method. Conveniently, the mutant protein is encoded by a suitable nucleic acid molecule and expressed in a suitable host cell. Suitable nucleic acid molecules encoding the mutant membrane protein may be made using standard cloning techniques, site-directed mutagenesis and PCR as is well known in the art. Suitable expression systems include constitutive or inducible expression systems in bacteria or yeasts, virus expression systems such as baculovirus, semliki forest virus and lentiviruses, or transient transfection in insect or mammalian cells. Suitable host cells include *E. coli, Lactococcus lactis, Saccharomyces cerevisiae, Schizosaccharomyces pombe, Pichia pastoris, Spodoptera frugiperda* and *Trichoplusiani* cells. Suitable animal host cells include HEK 293, COS, S2, CHO, NSO, DT40 and so on. It is known that some membrane proteins require specific lipids (eg cholesterol) to function. In that case, it is desirable to select a host cell which contains the lipid. Additionally or alternatively the lipid may be added during isolation and purification of the mutant protein. It will be appreciated that these expression systems and host cells may also be used in the provision of the mutant membrane protein in part (a) of the method of the first aspect of the invention.

Molecular biological methods for cloning and engineering genes and cDNAs, for mutating DNA, and for expressing polypeptides from polynucleotides in host cells are well known in the art, as exemplified in "Molecular cloning, a laboratory manual", third edition, Sambrook, J. & Russell, D. W. (eds), Cold Spring Harbor Laboratory Press, Cold Spring Harbor, N.Y., incorporated herein by reference.

It will be appreciated that further mutants can be produced by identifying the structural motifs in which the one or more mutations in a mutant membrane protein with increased stability reside. Such structural motifs, by virtue of them containing stabilising mutants, are important in determining protein stability. Thus, targeting mutations to these motifs will also facilitate the generation of further stabilised membrane proteins.

In a further embodiment of the first or second aspect of the invention, when the membrane protein is a GPCR, it is determined whether the selected or prepared mutant GPCR is able to couple to a G protein. It is also preferred if it is determined whether the selected or prepared mutant GPCR is able to bind a plurality of ligands of the same class as the selecting ligand with a comparable spread and/or rank order of affinity as the parent GPCR.

A third aspect of the invention provides a mutant membrane protein prepared by the method of the second aspect of the invention.

The invention includes mutant membrane proteins, for example mutant GPCRs, with increased stability compared to their parent proteins.

Mutant Muscarinic Receptor

Muscarinic receptors are known in the art. They share sequence homology and bind muscarine as well as acetylcholine which is their physiological ligand.

The invention includes a mutant muscarinic receptor which, when compared to the corresponding wild-type muscarinic receptor, has a different amino acid at a position which corresponds to any one or more of the following positions according to the numbering of the human muscarinic receptor M1 as set out in FIG. 7: Leu 65, Ile 73, Ile 74, Tyr 82, Trp 101, Met 145, Leu 151, Ile 383, Met 384, Glu 397, Leu 399, Val 409 and Ile 413.

It is particularly preferred if the mutant membrane protein is one which has at least 20% amino acid sequence identity when compared to the given human muscarinic receptor sequence, as determined using MacVector and CLUSTALW. Preferably, the mutant membrane protein has at least 30% or at least 40% or at least 50% amino acid sequence identity.

The mutant muscarinic receptor may be a mutant of any muscarinic receptor provided that it is mutated at one or more of the amino acid positions as stated by reference to the given muscarinic receptor amino acid sequence.

Thus, the invention includes a mutant human muscarinic receptor in which, compared to its parent, one or more of these amino acid residues have been replaced by another amino acid residue. The invention also includes mutant muscarinic receptors from other sources in which one or more corresponding amino acids in the parent receptor are replaced by another amino acid residue. For the avoidance of doubt the parent may be a muscarinic receptor which has a naturally-occurring sequence, or it may be a truncated form or it may be a fusion, either to the naturally-occurring protein or to a fragment thereof, or it may contain mutations compared to the naturally-occurring sequence, providing that it retains ligand-binding ability.

By "corresponding amino acid residue" we include the meaning of the amino acid residue in another muscarinic receptor which aligns to the given amino acid residue in human muscarinic receptor when the human muscarinic receptor and the other muscarinic receptor are compared using MacVector and CLUSTALW.

It is preferred that the particular amino acid is replaced with an Ala. However, when the particular amino acid residue is an Ala, it is preferred that it is replaced with a Leu.

It is preferred that the mutant membrane proteins of the invention, including the mutant muscarinic receptor, have an increased thermostability compared to its parent. Depending upon whether the membrane protein binds to a ligand, the mutant membrane preferably has increased thermostability when in the presence or absence of a ligand thereto.

It is preferred that the mutant membrane protein is at least 2° C. more stable than its parent preferably at least 5° C. more stable, more preferably at least 8° C. more stable and even more preferably at least 10° C. or 15° C. or 20° C. more stable than its parent. Typically, thermostability of the parent and mutant receptors are measured under the same conditions.

It is preferred that the mutant membrane protein, when solubilised and purified in a suitable detergent has a similar thermostability to bovine rhodopsin purified in dodecyl maltoside. Where the membrane protein binds to a ligand, it is particularly preferred that the mutant membrane protein retains at least 50% of its ligand binding activity after heating at 40° C. for 30 minutes. It is further preferred that the mutant membrane protein retains at least 50% of its ligand binding activity after heating at 55° C. for 30 minutes.

The mutant membrane proteins disclosed herein are useful for crystallisation studies and are useful in drug discovery programmes. They may be used in biophysical measurements of receptor/ligand kinetic and thermodynamic parameters eg by surface plasmon resonance or fluorescence based techniques. They may be used in ligand binding screens, and may be coupled to solid surfaces for use in high throughput screens or as biosensor chips. Biosensor chips containing the mutant membrane proteins may be used to detect molecules, especially biomolecules.

The invention also includes a polynucleotide which encodes a mutant membrane protein of the invention. In particular, polynucleotides are included which encode the mutant muscarinic receptor of the invention. The polynucleotide may be DNA or it may be RNA. Typically, it is comprised in a vector, such as a vector which can be used to express the said mutant membrane protein. Suitable vectors are ones which propagate in and/or allow the expression in bacterial or mammalian or insect cells.

The invention also includes host cells, such as bacterial or eukaryotic cells, which contain a polynucleotide which encodes the mutant membrane protein. Suitable cells include $E.$ $coli$ cells, yeast cells, mammalian cells and insect cells.

The invention will now be described in more detail with respect to the following Figures and Examples wherein:

FIG. 1 Model of $M_1$ muscarinic acetylcholine receptor showing the location of amino acids, depicted in dark grey, whose substitution by alanine detectably increased the expression levels of the mutant receptors when expressed in a mammalian (COS-7) cell line. The locations of other potentially important amino acids are shown in light grey.

Figure 2A:
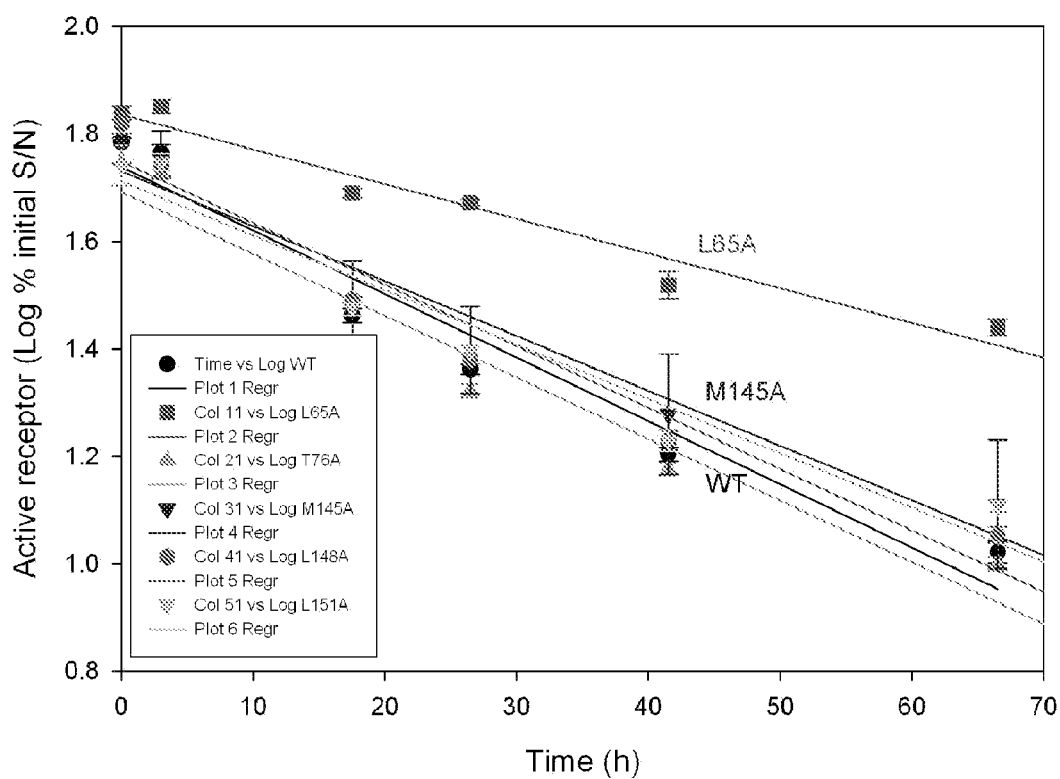
Figure 2B:
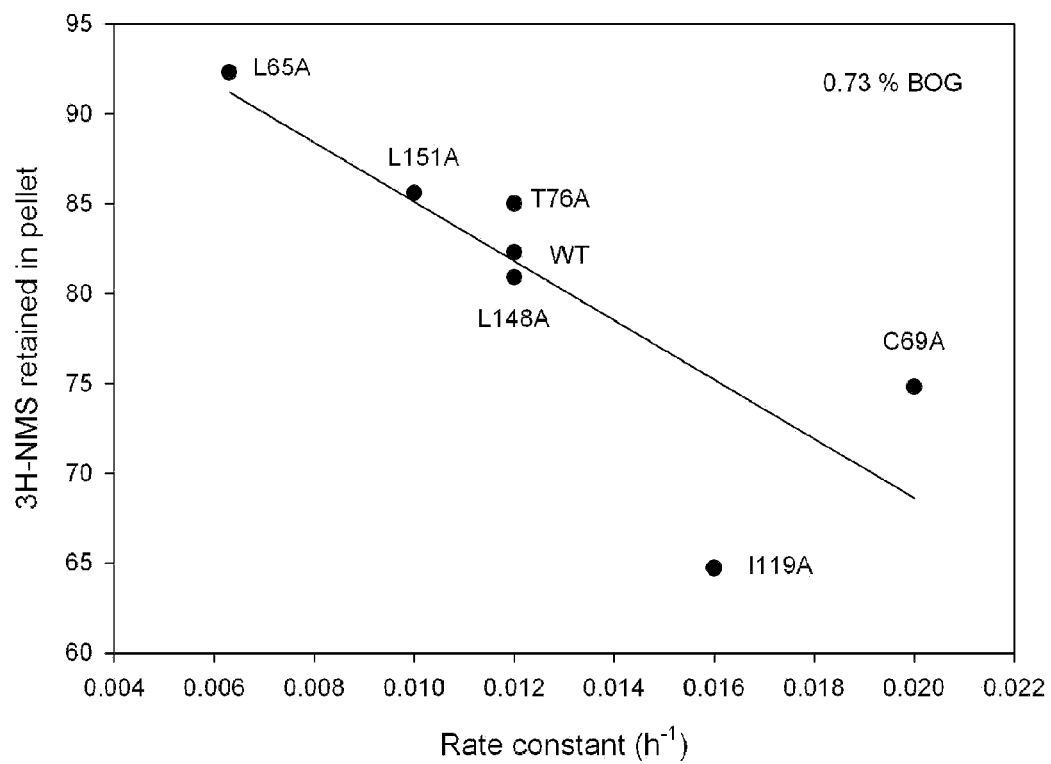

FIG. 2A-B Screening assay for mutants with enhanced stability in β-octyl glucoside. $^3$H—NMS-labelled mutant $M_1$ mAChRs are expressed in $E.$ $coli$ cultures and after centrifugation and resuspension to a standard cell density, they are incubated with a standard concentration of β-octyl glucoside for 3 h at 4° C. with regular gentle mixing before centrifugation and assay. FIG. 2A depicts evaluation of the stabilities of the mutant $M_1$ mAChRs receptors depicted in FIG. 1 expressed in $E.$ $Coli$ spheroplast membrane preparations, labelled with the antagonist $^3$H—N-methyl scopolamine, and subjected to full solubilisation in 1% β-octyl glucoside. The graph shows binding activity as a function of time at a temperature of 4° C. FIG. 2B depicts stabilities of $^3$H—NMS labelled mutant $M_1$ mAChRs estimated by the membrane in-situ destabilisation assay, using 0.73% β-octyl glucoside to treat intact $E.$ $Coli$ cells, compared with the rate constants of inactivation of the same mutants measured after full solubilisation in 1% β-octyl glucoside, calculated from data such as that shown in FIG. 2A.

Figure 3A:
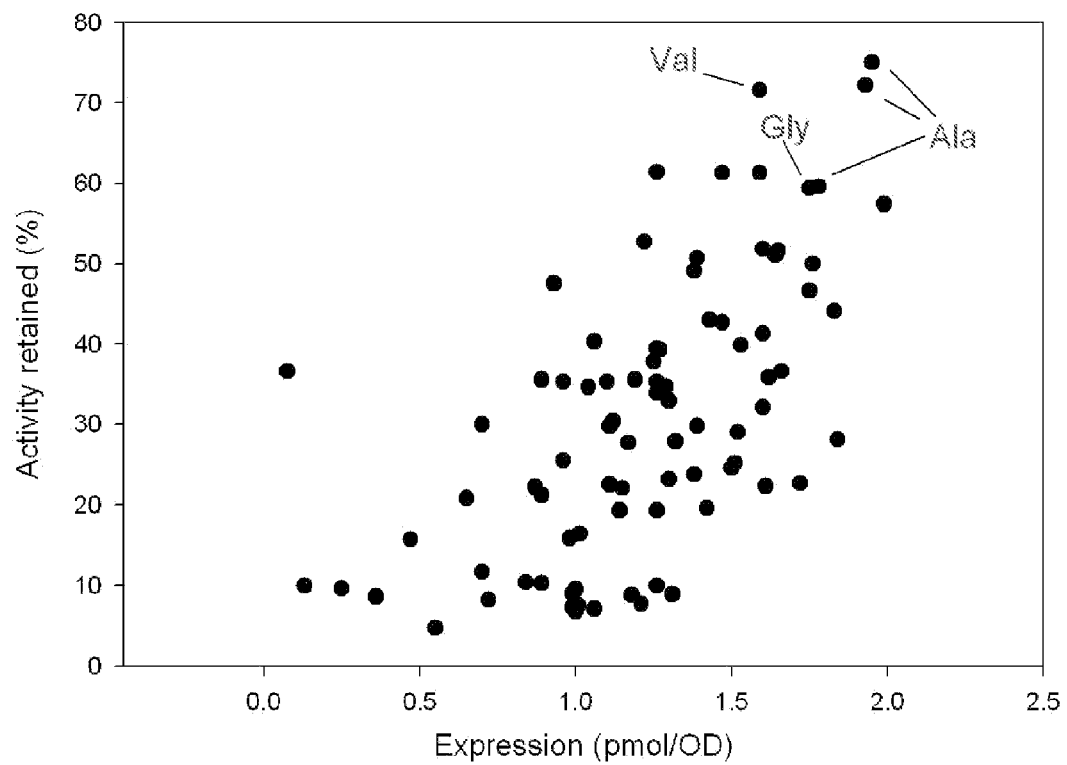
Figure 3C:
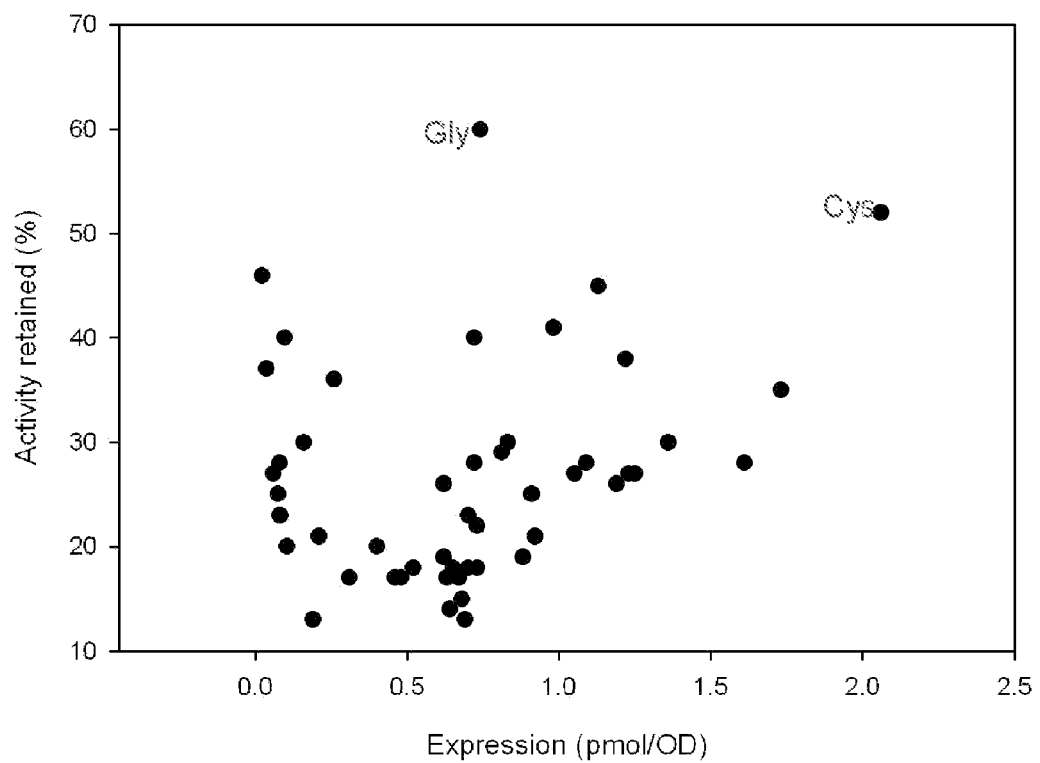

FIG. 3A-C Illustration of the application of the membrane in-situ destabilisation screening assay to isolate stable mutants of the $M_1$ mAChR after randomisation of the codons for (A) Leu65; (B) Ile383 and (C) Met384. In total, L65 (TM2), T379, I383, M384, L386, V387 (TM6) and L399 (TM7) were randomised and the mutant libraries were screened for enhanced stability in β-octyl glucoside. The membrane in-situ destabilisation assay was performed with 0.82% β-octyl glucoside at 4° C. for 3 h. Stability, indicated by $^3$H—NMS binding activity retained, is plotted against expression levels for the clones recovered. The identities of the most stable clones isolated was determined by DNA sequencing. The clones recovered by screening were L65A, L65V, I383G, M383G, M384C. In addition, the method was applied to position L399, and thereby the clone L399M isolated. Side chains selected were often less bulky than their parent and it was found that there is not a 1:1 correlation between expression level and β-octyl glucoside stability.

Figure 4A:
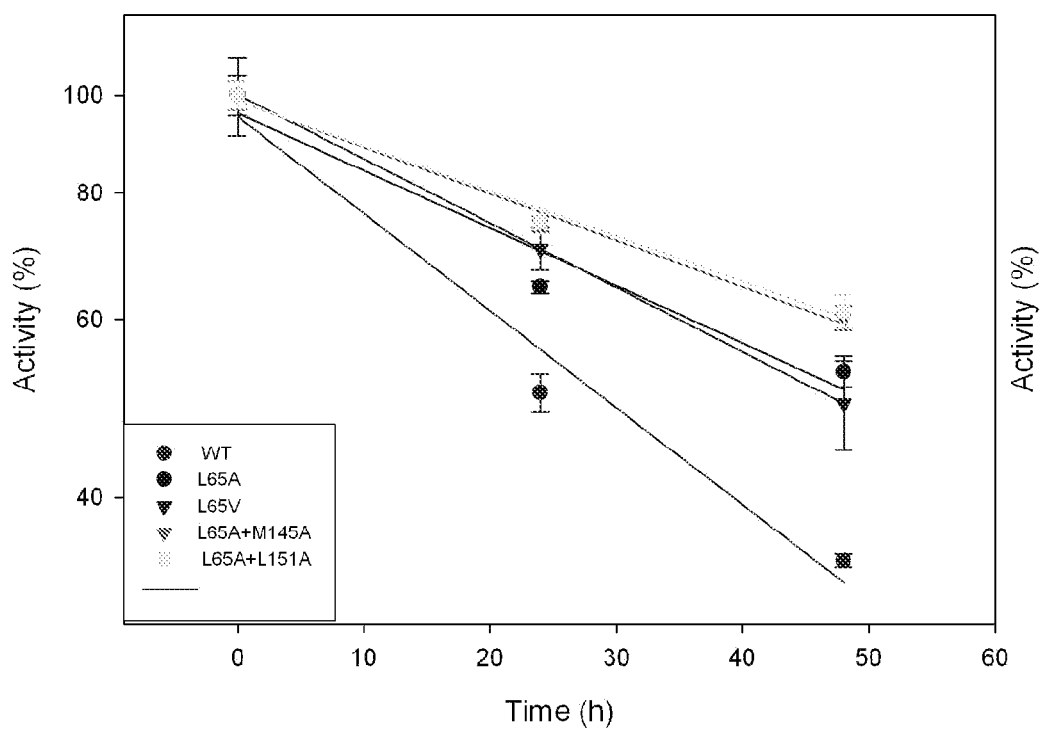
Figure 4B:
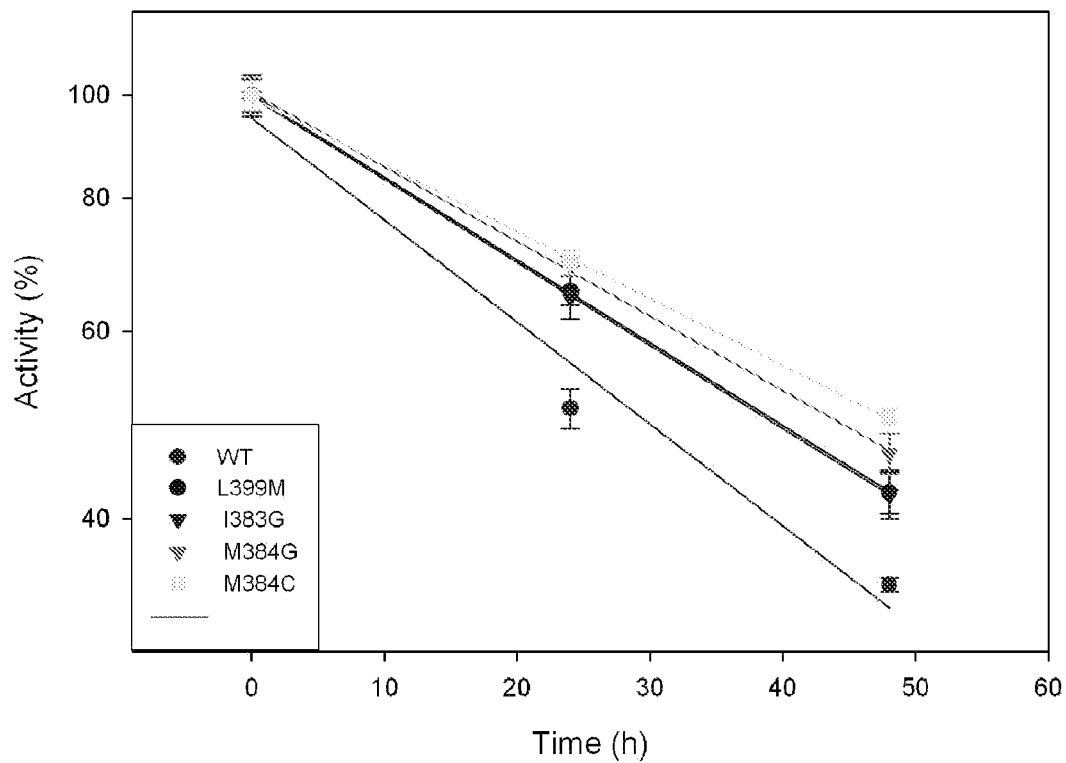

FIG. 4A-B Stabilities of mutant clones isolated by membrane in-situ destabilisation screening following full solubilisation of the $^3$H—NMS-labelled receptors expressed in *E. Coli* spheroplast membranes using 1% β-octyl glucoside. Mutants selected by screening show enhanced stability when solubilised in β-octyl glucoside. FIG. 4A shows that the L65A and L65V mutants show enhanced stability with respect to wild-type. This is further enhanced by making double mutants L65A/M145A and L65A/L151A. FIG. 4B shows that the I383G, M384G and L399M all show enhanced stability with respect to wild-type.

Figure 5:
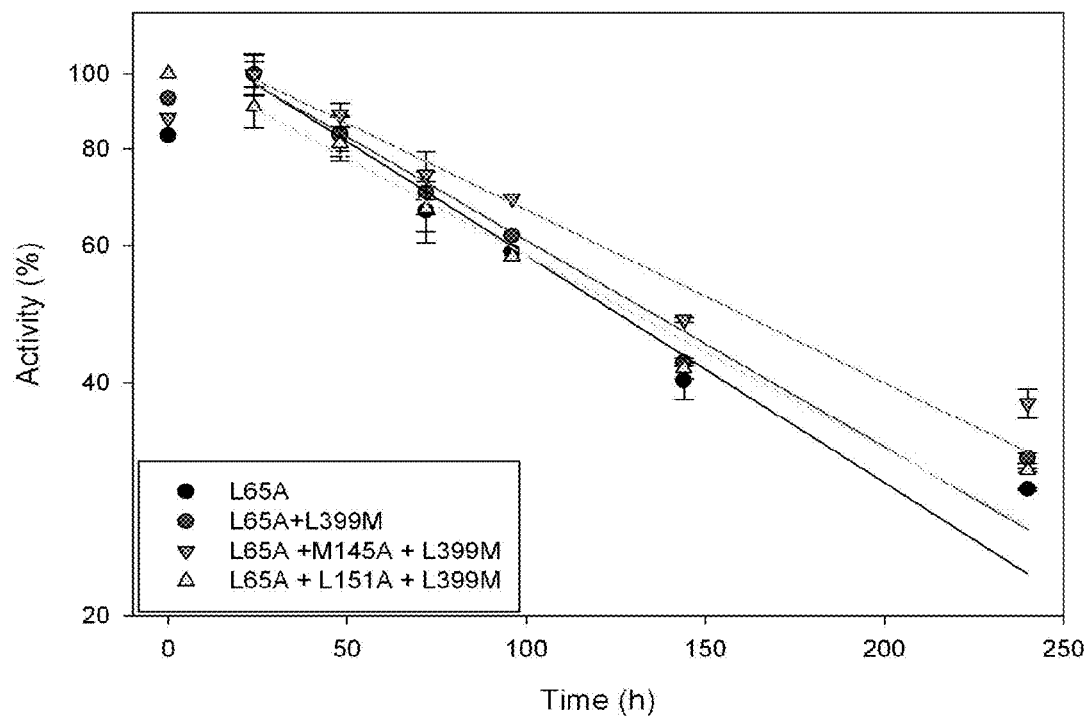

FIG. 5 Stabilities of single, double and triple mutant clones of the $M_1$ mAChR after full solubilisation of the 3H—NMS-labelled receptors expressed in *E. Coli* spheroplast membranes using 1% β-octyl glucoside. Addition of the L399M mutant, isolated by the membrane destabilisation screen, provided a further increment of stability.

Figure 6:
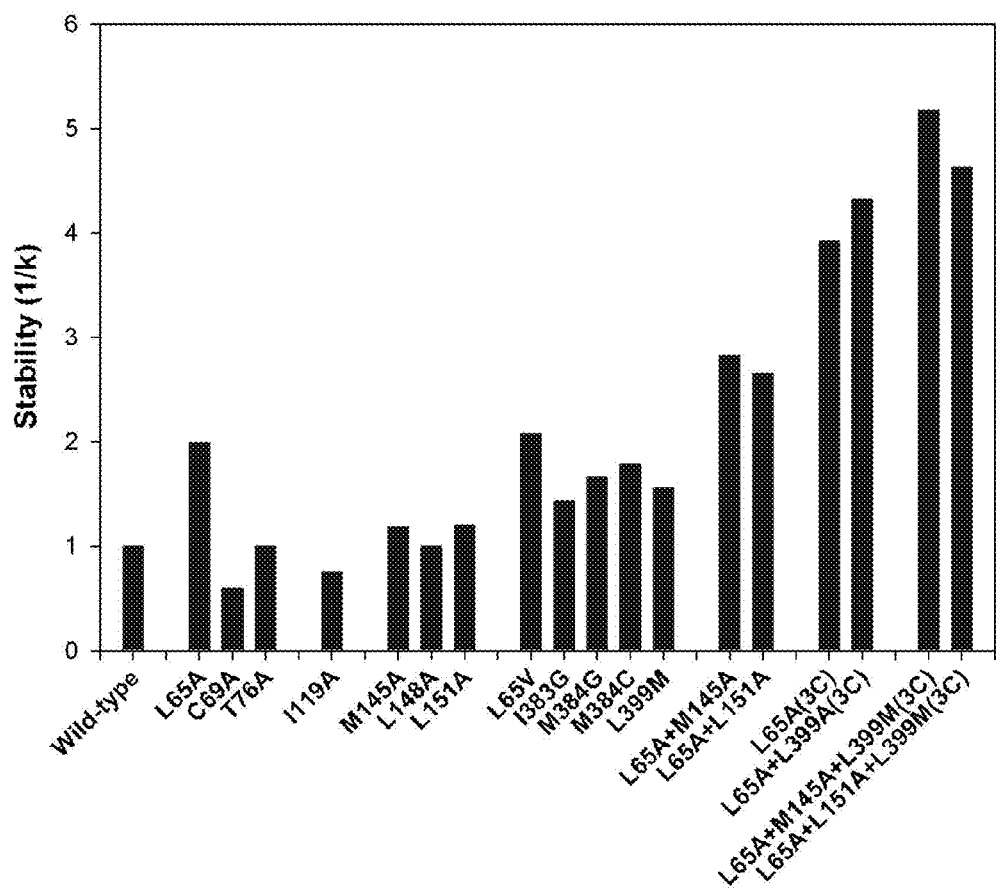

FIG. 6 Summary of stabilities of mutant clones of the M1 mAChR following full solubilisation of 3H—NMS-labelled receptors expressed in *E. Coli* spheroplast membranes using 1% β-octyl glucoside. The plot shows the reciprocal of the rate constant of inactivation. The designation 3C indicates that the receptor sequence had a 3C protease site inserted N-terminal to the initiator methionine.

Figure 7A:
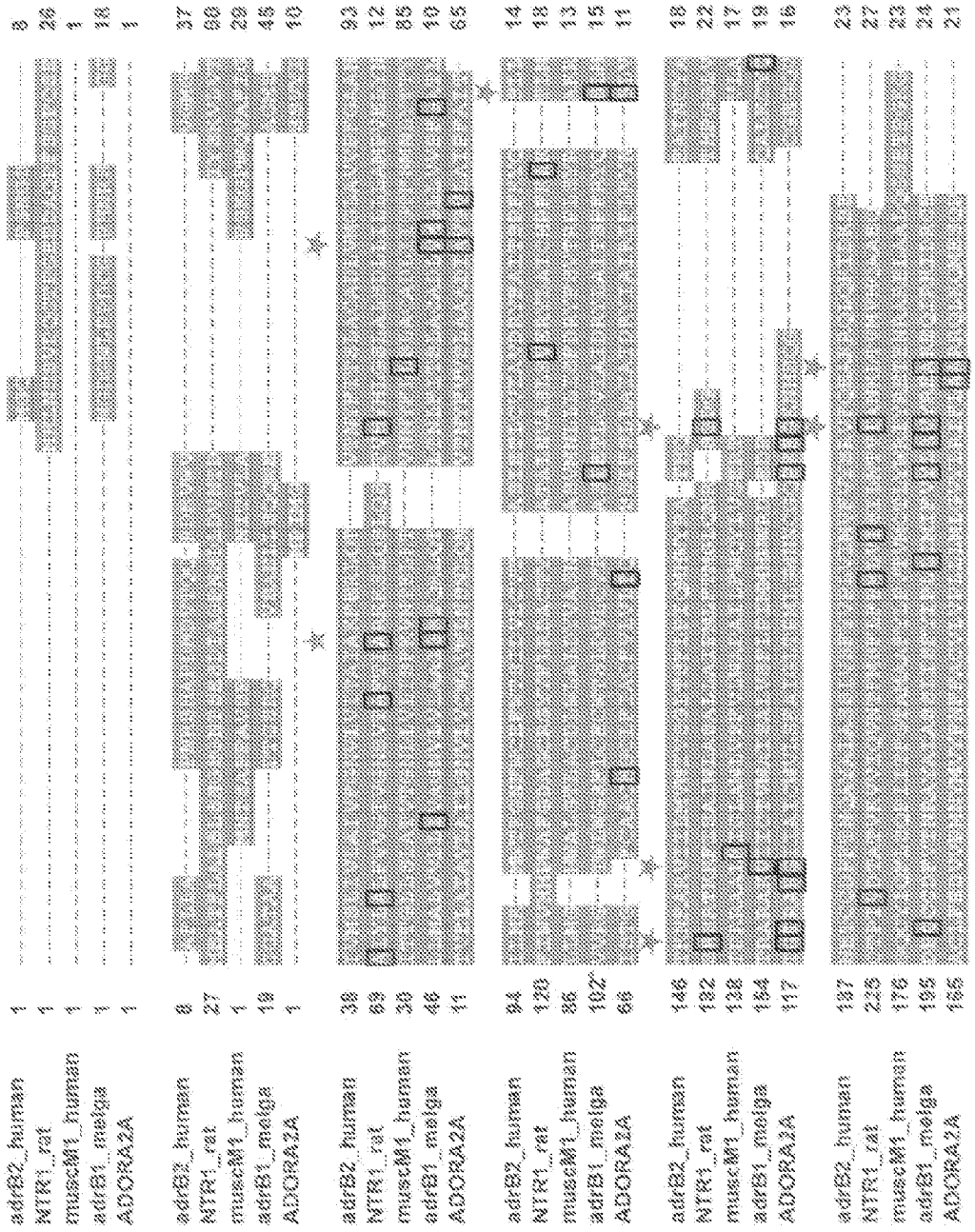
Figure 7B:
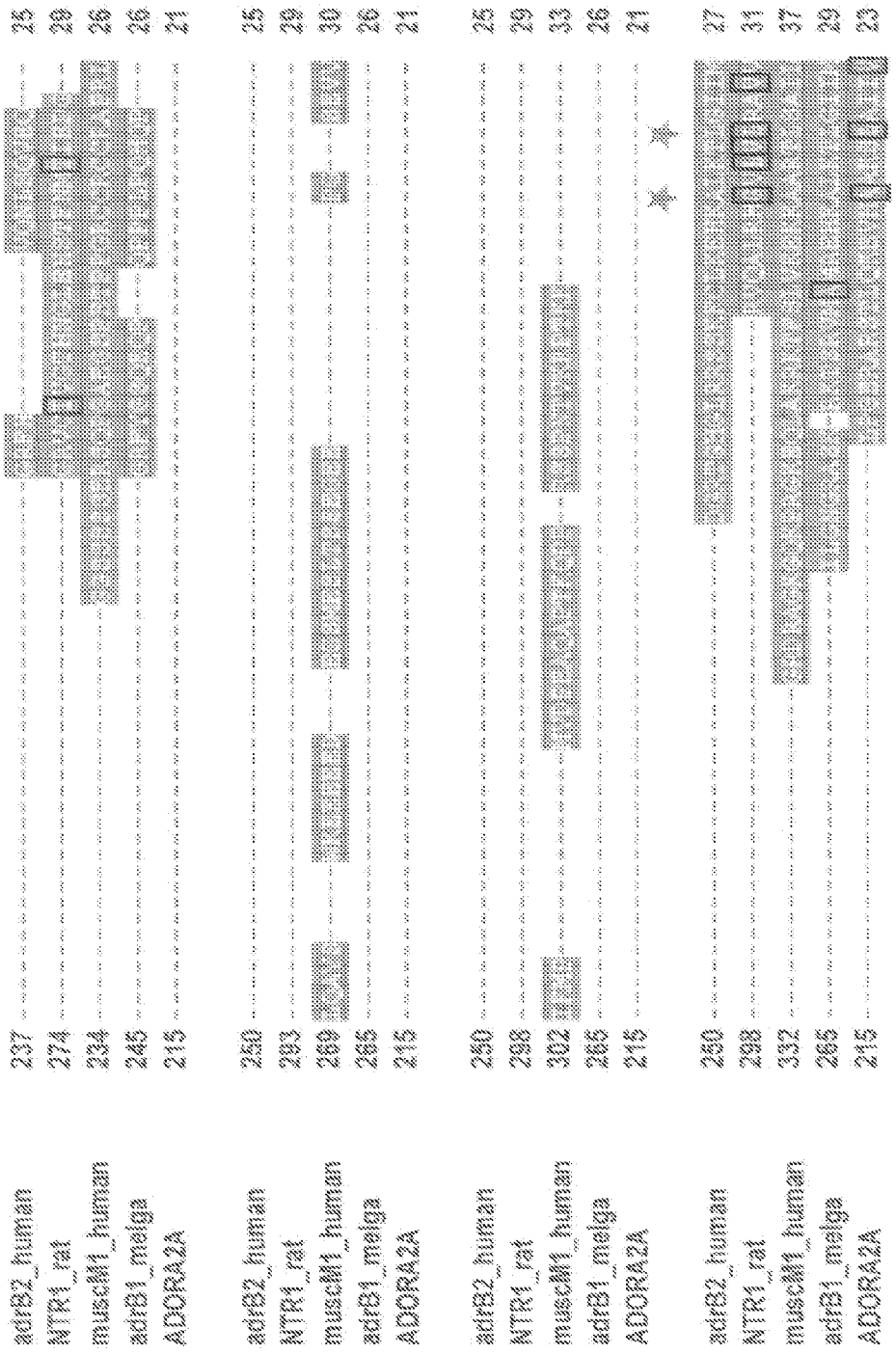
Figure 7C:
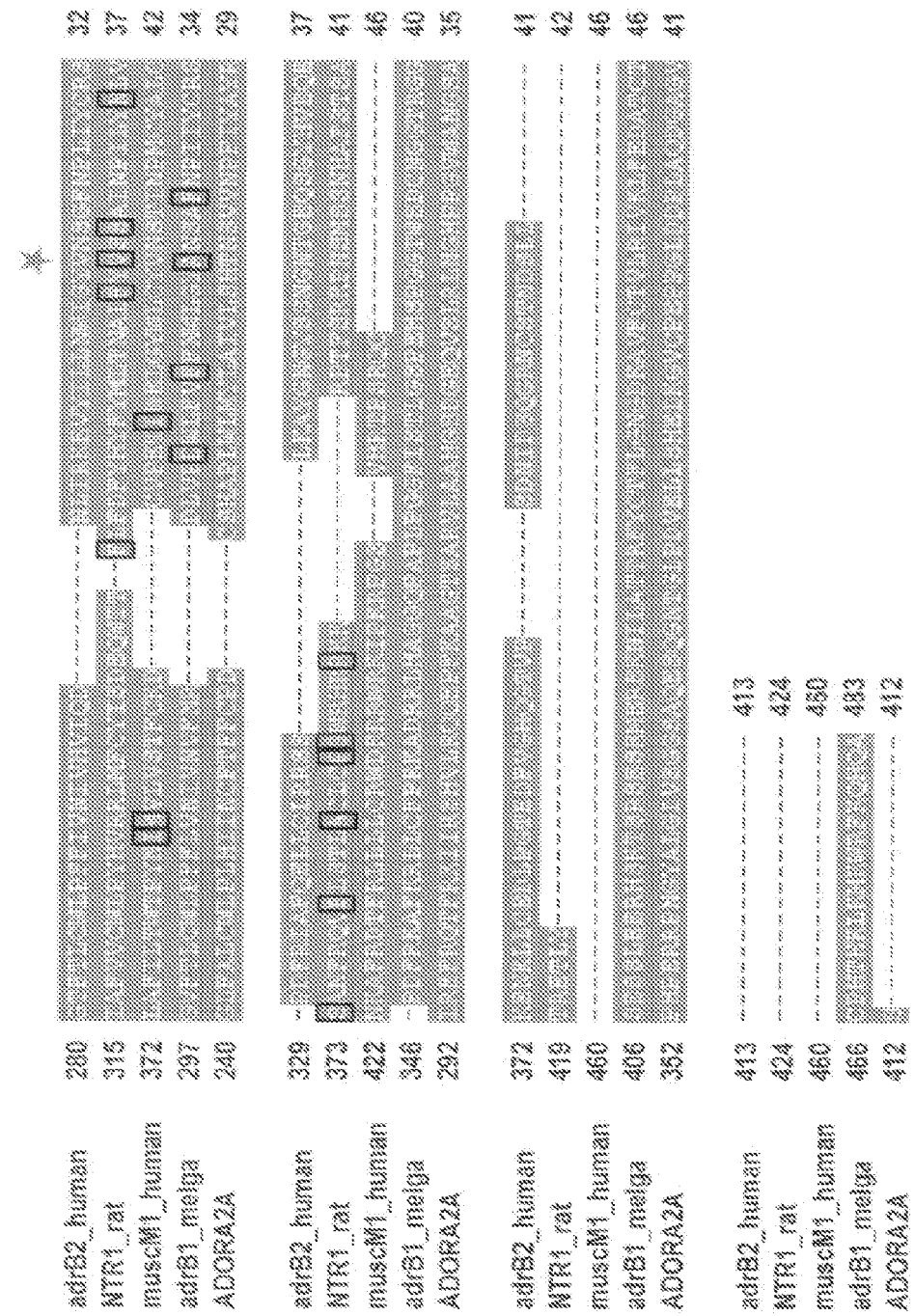

FIG. 7A-C Multiple sequence alignment of human beta-2AR, rat NTR1, turkey beta-1 AR, human Adenosine A2aR and human muscarinic M1 receptors. In each sequence, thermostabilising mutations are marked with a box. Mutations occurring in two or more sequences are denoted with a star.

FIG. 8 Diagram showing change in equilibrium between the folded-native state and the unfolded state of a membrane protein upon increasing exposure to a membrane destabilising agent. Increasing exposure to destabilising agent is indicated by dashed arrow. (A) No destabilising agent, equilibrium shifted towards folded-native state. (B) Exposure to increasing concentrations of destabilising agent results in the proportion of membrane proteins in the unfolded state increasing, and the proportion of membrane proteins in folded-native state decreasing. (C) At high concentrations of destabilising agent, the equilibrium is shifted towards the unfolded stated.

Figure 9:
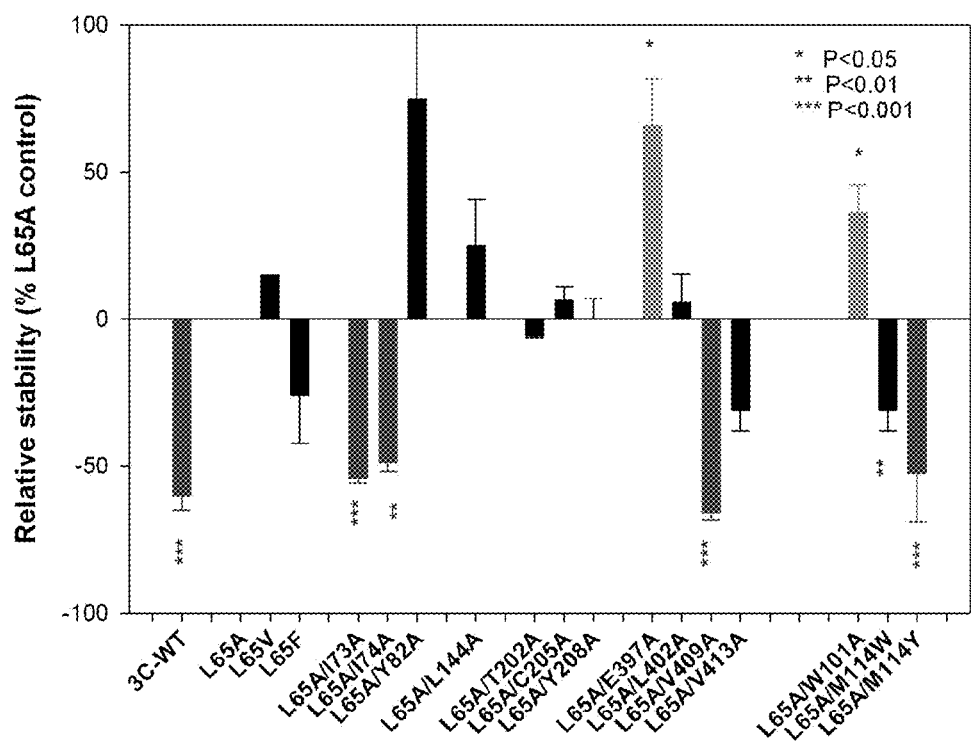

FIG. 9 $M_1$ mAChR β-adrenergic receptor M23-homologous mutants in *E. coli*: In-situ destabilisation assays relative to L65A.

Figure 10:
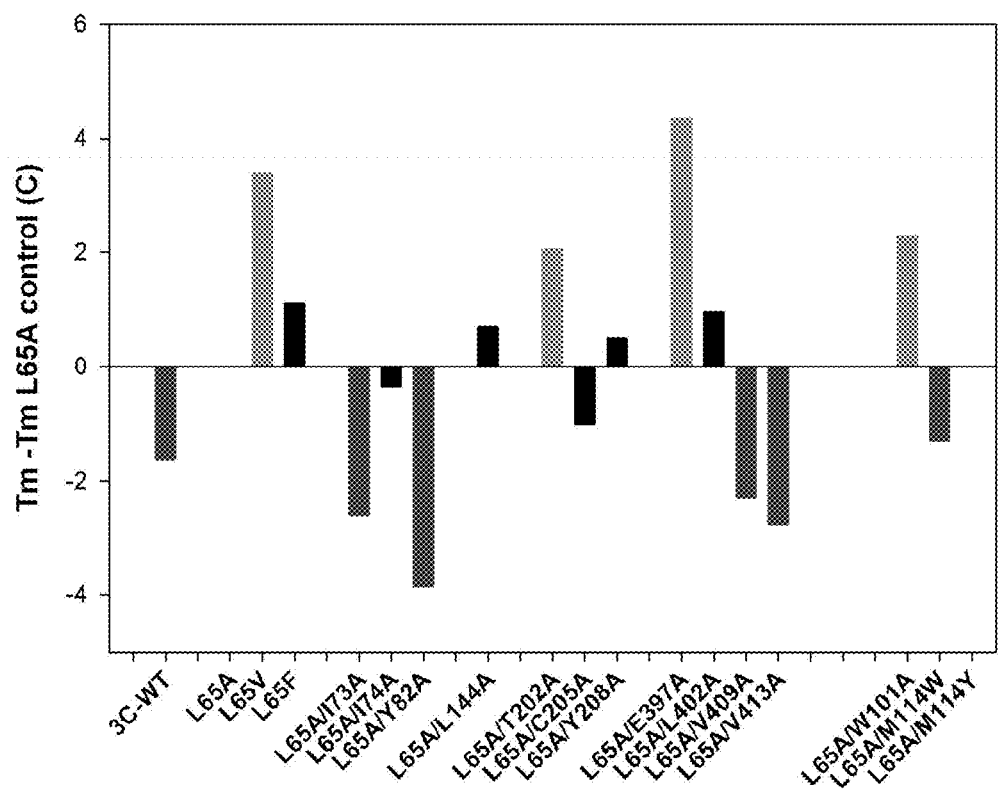

FIG. 10 Thermal stabilities of $M_1$ mAChR "M23" mutants relative to L65A measured in 0.1% DDM.

EXAMPLE 1

"In-Situ Destabilisation" Method of Assessing Membrane Protein Stability (a) A state of in-situ destabilisation of a particular membrane protein in a particular cell membrane as a result of the addition of a particular concentration of a particular detergent, can be defined by the loss of the characteristic specific ligand binding activity of the membrane protein for a particular ligand of interest in the presence of a defined concentration of a particular detergent molecule or other solubilising agent.

A preferred version of the assay is destabilisation of a membrane protein-ligand complex in a detergent-enriched membrane. The membrane protein, either in a membrane preparation, or in intact cells in-vivo or ex-vivo, is pre-incubated with a labelled version of the ligand, the label, for instance, being a radioactive label, or a fluorescent label, and the binding step preferably being allowed to proceed to equilibrium, defined as the achievement of a time-invariant level of binding. To define membrane protein-independent, or non-specific, binding the binding step is performed with the addition of a second non-labelled ligand, called the competing ligand, having an appropriate membrane protein-specific pharmacology, at a concentration sufficient fully to occupy the binding sites of the membrane protein and thereby exclude the binding of the labelled ligand. The difference between the binding of the labelled ligand in the absence and presence of the competing ligand is defined as the specific binding of the labelled ligand. Measurement of binding requires a suitable method for separating and measuring bound ligand. Characteristically, this involves centrifugation of intact cells or membranes for a time and at a centrifugal force adequate to pellet them (for instance, 15000×g for 15 min in the case of *E. coli* cells, or 100,000×g for plasma membrane preparations), or filtration of a membrane suspension e.g. through a suitable filter paper such as glass fibre paper e.g. GF-B or GF-C followed by counting of radioactivity. Alternatively, it might involve the measurement of an optical signal such as enhancement of fluorescence emission in the case of fluorescent ligands.

To perform the in-situ destabilisation assay, a pre-determined concentration of the detergent or other destabilising agent of choice is mixed with a membrane or cell suspension containing the pre-labelled membrane protein in an appropriate buffer composition at a particular temperature and for a particular time, determined as described below. Such a buffer might include a particular concentration of the labelled or unlabelled ligand, or other membrane protein-active chemical agents. It might also contain other general additives such as protease inhibitors and chaotropic agents or chelating agents. A control assay is performed from which the destabilising agent is omitted, an equal volume of the buffer omitting the said destabilising agent being added instead. After the elapse of the defined time, the residual membrane protein-specific binding activity is determined. The fraction of the specific binding activity of the membrane protein retained in the presence of the destabilising agent compared to that retained in the control incubation, expressed as a percentage, and designated "% activity retained", abbreviated "% A", is then defined as the stability or retention of the membrane protein-ligand complex in the presence of the given concentration of detergent over the assay period. 100-% A then designates the in-situ destabilisation of the membrane protein-ligand complex. If % A, measured with sufficient replication, is statistically significantly less than 100%, such that the reduction would be observed by chance in only 1 in 10 or in only 1 in 20 experiments or more preferably in only 1 in 100 experiments, it may be inferred that the destabilising agent has destabilised the membrane protein-ligand complex. Control samples processed at time zero before the addition of destabilising agent allow the stability of the membrane protein in the membrane to be assessed over the time-period of the stability assay.

In a less-preferred variant of the assay, the detergent or other destabilising agent, and buffer control, is added to the cell or membrane suspension without pre-labelling the membrane protein with the ligand of interest. After incubation for a particular time and at a particular temperature, as defined above, the labelled ligand is added for a time sufficient to label the residual membrane protein, before separation of the membrane protein-ligand complex, as above.

(b) The minimum, maximum and preferred concentrations of the destabilising agent of interest are determined by incubating the particular membrane or cell suspension containing the membrane protein, pre-labelled with ligand or otherwise with a series of detergent concentrations at a particular temperature and for a particular time up to, including, and slightly exceeding the threshold for membrane protein solubilisation.

If this concentration is designated S, then a suitable series of concentrations might be 1.1×S, S, 0.9×S, 0.8×S, 0.7×S, 0.6×S, 0.5×S, 0.4×S, 0.3×S, 0.2×S, 0.1×S, 0. The resulting curve of % A against detergent concentration is fitted to a suitable empirical function, for instance a logistic function. A suitable destabilising concentration might be one that produces a % A value of 50 for the wild-type membrane protein. This concentration, designated $A_{50}$, is interpolated from the fitted curve. Use of an $A_{50}$ concentration of detergent allows conditions that both increase and decrease stability to be detected. However, the use of other destabilising concentrations such as 0.5×$A_{50}$, or 2×$A_{50}$ or 0.2×$A_{50}$ or 5×$A_{50}$ might be preferable depending on the precise aims of the experiment.

The initial determination of S involves the performance of a solubilisation experiment, in which the membrane or cell suspension containing the membrane protein is incubated with a series of detergent concentrations such as 0, 0.2 0.4, 0.6, 0.8, 1.0, 1.5, 2.0, 2.5% weight/volume for a particular time, centrifuging the resulting suspension for at least 60 min at 100,000×g or more, and then assaying the supernatant fraction for the soluble membrane protein-ligand complex, using, for instance, a gel-filtration assay to separate bound from free labelled ligand, or by gel-electrophoresis and Western blotting with an appropriate antibody. The time and temperature used for solubilisation would preferably be the same as that used in the stability assay, but a different time and temperature might be used. The concentration of detergent designated S would then typically be taken as the concentration yielding 10% solubilisation of the membrane protein or membrane protein-ligand complex, although a higher or lower concentration might also be used in certain circumstances. It is recommended to determine a protein solubilisation curve in parallel to the membrane protein solubilisation curve.

(c) The value of $A_{50}$ will depend on the membrane protein studied, on the nature of the membrane protein-ligand complex, on the nature of the cell (for instance, whole bacterial cells, insect cells, or mammalian cells) or membrane suspension (for instance, bacterial spheroplast membranes, mammalian plasma membranes) on the composition of the buffer system (for instance, the pH, ionic strength and divalent cation content, or content of chelating agents), on the temperature used (for instance, 4° C., 10° C., 20° C., 30° C.), on the presence of additional perturbing or stabilising agents (for instance organic solvents such as dimethyl sulfoxide or isopropanol) or enzymes (such as lysozyme) and on the chemical nature and properties of the detergent used (for instance the critical micellar concentration, CMC). The assays should be conducted under conditions under which the membrane protein-ligand complex in the membrane is stable for the period of the assay. As explained above, this can be ascertained by processing control samples at time zero for comparison with samples processed at the end of the assay period.

The appropriate time and temperature for the in-situ destabilisation assays must be determined empirically for the particular membrane protein-ligand complex, buffer system and detergent combination. Thus, assays should be conducted at temperatures such as 0° C., 5° C., 10° C., 15° C., 20° C., 25° C., 30° C. or higher, and for times such as 1 h, 2 h, 3 h, at pH values such as 4, 5, 6, 7, 8, 9. The $A_{50}$ value for each condition is estimated as explained above.

(d) Where the destabilising agent is a detergent, the detergents to be used should preferably be those that are of interest for subsequent crystallization studies or other studies, for instance short chain-length detergents with a high CMC, such as C8-glucoside, C8-thioglucoside, C9-glucoside, C8-maltoside, C8-thiomaltoside, C9-maltoside, C9-thiomaltoside, Cymal 5, C8E5, or lauryl dimethylamine oxide. Short chain-length detergent are more likely to allow the formation of a 3-dimensional crystal lattice, and are easier to remove from membrane protein preparations by dialysis, or other means than are long chain-length detergents with low CMCs. Such detergents also have an extended working concentration range in destabilization experiments, because detergents, generally, do not solubilize membranes when present at concentrations below their CMCs. For M1 muscarinic acetylcholine membrane proteins, we have preferred to use β-octylglucoside (β-C8-glucoside).

(e) The above method may also be adapted to the use of other amphiphilic molecules and other solubilising agents. These may include amphipols, amphiphilic peptides such as mellitin, proteins such as apolipoproteins and their derivatives, local anaesthetics and drugs such as procaine and chlorpromazine, polyols such as butane diol and heptane triol, alcohols such as propanol and isopropanol and enzymes that perturb membrane structure such as phospholipase A.

EXAMPLE 2

Development of In-Situ Destabilisation Approach in Whole-Cell Screening Assay for Stability of Muscarinic Receptor Mutants Background:

Certain Ala-mutants in the transmembrane (TM) region of the $M_1$ mAChR were expressed in mammalian cells (COS-7) at higher levels than the wild-type. Several of these also showed higher expression in the *E. coli* (malE-$M_1$mAChR N-terminal fusion) over-expression system (3, 16, 19). After in-situ destabilisation in β-octyl glucoside (BOG), or dodecyl maltoside (DDM) one mutant (L65A, TM2) showed 2-fold enhanced stability, relative to wild-type, measured by retention of a bound antagonist, 3H—NMS. Other solubilized mutants showed smaller enhancements (M145A, L151A), or reductions (C69A, I119A) of stability. These differences can be used to develop a simple whole-cell screening assay for enhanced stability of the mAChR-NMS complex Assay Development:

The basic concept was to achieve "in-situ destabilisation" (i.e. the creation of destabilising agent-enriched membranes) by exposing whole *E. coli* cells (strain BL21) expressing $M_1$ mAChRs labelled with $^3$H—NMS to a concentration of BOG too low to solubilise the cells, thus allowing them to be pelleted by centrifugation, but high enough for the destabilising agent to partition into the inner bacterial membrane, thus destabilising the receptor-NMS complex in-situ, causing time-dependent loss of the bound radioligand. A set of conditions was found that showed a correlation between retention of $^3$H—NMS in the whole cell assay and stability in solution for the basis set of mutants. This is exemplified in FIG. 2 panel B, which shows the correlation, for a series of mutants, between % A represented by % 3H—NMS retained in the bacterial cell pellet after 3 hours at 4° C. in the presence of 0.82% β-octyl glucoside (BOG) and the rate constant of inactivation of the corresponding mutants after full solubilisation in 1% BOG, measured by gel-filtration assays.

This assay was applied, on the laboratory scale, to screen for further stabilising mutants made by targeted random mutagenesis of selected sequence positions. In particular, randomisation of the codon for position 65 followed by selection recovered the following mutations: L65A, L65G and L65V.

Application to Screening of $M_1$ mAChRs:

BL21 gold competent *E. coli* cells (Stratagene) are transformed with a plasmid library e.g. containing random mutants of malE-$M_1$-mAChRs and plated on L-agar (100 μg/ml ampicillin, 0.2% glucose) overnight. Individual clones are picked into 10 ml of 2×TY (100 μg/ml ampicillin, 0.2% glucose), and grown at 25° C. (ELKAY tubes, 290 rpm). After ca. 7 h, the cultures are induced by the addition of 0.1 ml 50 mg/ml IPTG; simultaneously, $^3$H—NMS (1 Ci/mmol; $10^{-8}$ M, sterile) is added to label the cells in culture. After growth O/N (ca 16 h), 0.1 ml aliquots of cultures are mixed with 0.1 ml 30% glycerol/2×TY and frozen for stocks. Further 0.1 ml aliquots are mixed with 0.9 ml 50 mM NaPi, 1 mM EDTA, pH 8.0 (Pi/EDTA) for $OD_{500}$ measurements. Meanwhile, the remaining culture is centrifuged (15 min, 3,000 rpm) to pellet the cells. The supernatant is carefully decanted, and the pellets drained. The pellets are re-suspended by vortexing (in 2 stages if the final volume is greater than 10.0 ml) in ice-cold Pi/EDTA to give a final $OD_{600}$ of 2.0. Cultures with an OD of greater than 7.0 have been found (so far) not to express $M_1$ mAChRs (expression of the receptor restricts the growth of the cells), and are discarded. 0.5 ml aliquots are removed for liquid scintillation counting to provide an initial estimate of expression level ($pmol/OD_{600}$ initial). 4×1 ml eppendorf tubes are set up for each culture, 2 with 0.1 ml Pi/EDTA, and 2 with 0.1 ml 9.0% BOG in Pi/EDTA (to yield a final assay concentration of 0.82%). The assay is performed at 4° C. 1 ml aliquots of the re-suspended cultures are added to the corresponding sets of 4 tubes. The assays are mixed by inversion at the outset, and at 30 min intervals thereafter. After 3 h, the cells are pelleted (14,000 rpm, 15 min, 4° C.), and the supernatant carefully poured away. The tubes are left to drain for 15 min, the last few drops of supernatant being carefully removed from the lip of the tube with a vacuum line. The pellets are solubilised with 0.1 ml Soluene O/N, and counted using the tubes as counting inserts after the addition of 1 ml of non-aqueous scintillant. The measurements yield (i) a second measurement of expression level ($pmol/OD_{600}$ final); this may be lower than the initial expression estimate if significant dissociation of $^3$H—NMS occurred during the course of the assay and (ii) a measure of % $^3$H—NMS binding retained in the presence of 0.82% BOG, which we take to be a measure of receptor stability in the presence of the detergent. This may then be related to a wild-type control (% loss/% loss, WT).

This assay, carried out manually, has been applied to screen up to 100 clones in a single experiment. Three examples of primary screens using the in-situ membrane destabilisation assay employing 0.82% BOG applied to M1 mAChRs randomised at positions L65 (TM2), I383 and M384 (TM6) are shown in FIG. 3. The data for L65 shows proof of principle, that it is possible to recover a stabilising mutation (namely L65A) through the use of the in-situ membrane destabilisation screening method. Two additional candidate mutations were recovered, established by sequencing to be L65V and L65G. The data for positions I383 and M384 showed that it was also possible to recover candidate stabilising mutations from other sequence positions. An example of the data obtained from an experiment using the in-situ membrane destabilisation assay, to re-screen some of the clones that were initially isolated from a random screen of T379, I383 and M384 (TM 6), in comparison to mutations of L65 (TM2) and double mutants (L65A+M145A/L151A) is shown in Table 1 below. Sequencing established that I383/21 is I383G, M384/27 is M384C and M384/40 is M384G. We also isolated another candidate, namely L399M, by application of the in-situ membrane destabilisation screening assay to M1 mAChRs randomised at position L399. FIG. 3 shows stability assays after full solubilisation in 1% BOG, performed at 4° C. This illustrates that the mutant clones isolated using the in-situ membrane destabilisation screening assay did indeed manifest increased stability compared to wild-type after full solubilisation. The full solubilisation stability data shown in FIGS. 4a, 5 and summarised in FIG. 6 also show that it is possible, in principle, to obtain further increments of stability of M1 mAChRs solubilised in BOG by combining certain individual point mutants.

TABLE 1

| Mutant (clone #) | OD600 | pmol/ml culture | pmol/OD600 initial | pmol/OD600 final | % 3H-NMS retained BOG | mean % retained | % loss/wt |
|---|---|---|---|---|---|---|---|
| L65A 1 | 3.87 | 9.25 | 2.39 | 2.17 | 79 | 79 | 0.4 |
| L65A 2 | 3.87 | 7.4 | 1.91 | 1.85 | 79 | | |
| L148A 1 | 3.53 | 6.54 | 1.85 | 1.48 | 74 | 71.5 | 0.54 |
| L148A 2 | 3.99 | 8.11 | 2.03 | 1.8 | 69 | | |
| L65V 1 | 4.66 | 11.84 | 2.54 | 2.31 | 81 | 88 | 0.23 |
| L65V 2 | 4.54 | 9.41 | 2.07 | 1.75 | 95 | | |
| L65A 1 | 4.47 | 11.04 | 2.47 | 2.05 | 83 | 84.5 | 0.29 |
| L65 A 2 | 4.13 | 9.54 | 2.31 | 2.04 | 86 | | |
| L65 G 1 | 4.11 | 8.88 | 2.16 | 2.05 | 49 | 44 | 1.06 |
| L65 G 2 | 3.37 | 6.98 | 2.07 | 1.94 | 39 | | |
| L65A + M145A 1 | 4.28 | 9.14 | 2.13 | 1.76 | 91 | 82 | 0.34 |
| L65A + M145A 2 | 4.42 | 10.4 | 2.35 | 2.25 | 73 | | |
| L65A + L151A 1 | 4.06 | 10.22 | 2.52 | 2.5 | 70 | 73 | 0.51 |
| L65A + L151A 2 | 4.47 | 10.31 | 2.31 | 2.11 | 76 | | |
| T379/15 1 | 4.7 | 7.91 | 1.68 | 1.57 | 47 | 49.5 | 0.95 |
| T379/15 2 | 5.04 | 6.66 | 1.32 | 1.11 | 52 | | |
| I383/5 1 | 4.1 | 7.5 | 1.83 | 1.87 | 50 | 53.5 | 0.88 |
| I383/5 2 | 4.69 | 8.03 | 1.71 | 1.77 | 57 | | |
| I383/8 1 | 4.39 | 5.69 | 1.3 | 1.28 | 41 | 40.5 | 1.12 |
| I383/8 2 | 4.7 | 9.21 | 1.96 | 1.69 | 40 | | |
| I383/19 1 | 9.03 | | | | | | |
| I383/19 2 | 8.49 | | | | | | |
| I383/21 1 | 3.96 | 1.83 | 0.46 | 0.74 | 70 | 66 | 0.64 |
| I383/21 2 | 3.22 | 3.94 | 1.22 | 1.09 | 62 | | |
| I383/42 1 | 6.33 | 11.08 | 1.75 | 1.44 | 53 | 53 | 0.89 |
| I383 42/2 | 4.56 | 13.63 | 2.99 | 1.05 | 53 | | |
| M384/27 1 | 4.43 | 11.59 | 2.62 | 2.67 | 63 | 68 | 0.6 |
| M384/27 2 | 5.31 | 14.12 | 2.66 | 2.29 | 73 | | |
| M384/40 1 | 4.51 | 6.6 | 1.46 | 1.38 | 71 | 76.5 | 0.44 |
| M384/40 2 | 3.73 | 5.9 | 1.58 | 1.09 | 82 | | |
| WT | 3.95 | 8.18 | 2.07 | 2.11 | 49 | 46 | 1.02 |
| | 0.53 | | 1.34 | 0.87 | 45 | | |
| | | | | | | 44 | |

EXAMPLE 3

Evaluation of Stabilising Mutations of the $M_1$ mAChR

Introduction

A selection of mutants of the $M_1$ mAChR was evaluated by the in-situ destabilisation assay and by full thermal stability measurements in order to assess the power of the in-situ method to identify stabilising mutations.

Selection of Mutants:

The first group of mutants was based on homology to thermostabilising mutations in the turkey β1 adrenergic receptor (24). The positions chosen included 4 of the 6 members of the "M23" set of thermostabilising mutations, namely M90, Y227, F327, F338 but omitted R68 and A282, for which no good homologies are found in the $M_1$ mAChR. Other residues were the turkey β1 adrenergic receptor residues V89, G98, V160, L221, I224 and D322. The corresponding $M_1$ mAChR residues are shown in Table 3, with their Ballesteros-Weinstein designation. These residues were mutated to Ala. The background used was L65A, which is significantly more stable than the wild-type $M_1$ mAChR.

A second group of mutants comprised additional mutations of L65, including L65V which, like L65A, was picked out by random mutagenesis screening, and L65F, which corresponds to the residue found at this position in the $M_4$ mAChR. We also investigated W101A, a mutation that causes a dramatic enhancement of the affinity of functionally $M_1$-selective ligands related to AC-42 (25), and examined mutations in transmembrane (TM) helix 3 homologous to those of E122 which have been reported to stabilise the β2 adrenergic receptor (23).

The mutants were evaluated both by the in-situ destabilisation assay, using β-octyl glucoside (BOG) and by thermal stability measurements on partially-purified receptors in dodecyl-β-maltoside (DDM).

Methods

Expression:

Mutant $M_1$ mAChRs receptors were expressed in *E. Coli* strain BL21 using a standard construct that produces an N-terminal malE-fusion with a 3C protease cleavage site N-terminal to the receptor gene. The receptor has a 129 amino acid deletion in intracellular loop 3 to remove protease-sensitive sites, and has the sequence $(His)_9QGG$ at the C-terminus to enable purification by IMAC and to protect against carboxypeptidase activity. These changes are summarised in Table 2. The receptor retains normal binding affinities for (−)-[3H]N-methyl scopolamine ([3H]NMS) and (−) [3H]-3-quinuclidinyl benzilate ([3H]]QNB).

In-Situ Stability Measurements:

For in-situ stability measurements, individual clones expressing $M_1$ mAChRs were grown and labeled with the antagonist (−)-[3H]—N-methylscopolamine [3H]NMS. The expressing cells were harvested and resuspended in 50 mM sodium phosphate, 1 mM EDTA pH 8.0 to give an $OD_{600}$ value of 2.0. In-situ stability measurements were conducted by measuring the loss of bound [3H]NMS from $M_1$ mAChRs induced by a concentration of β-octyl glucoside of 0.82% over a period of 3 h at 4° C. with regular mixing, as described in Example 2. Results were expressed relative to an internal control consisting of the L65A mutation, to give a value of % loss(mutant)/% loss(control). The stability value is the inverse of this, namely % loss(control)/% loss(mutant). Values were tabulated as mean±SEM of 3 independent measurements (Table 3).

Thermal Stability Measurements:

For measurements of thermal melting temperature (Tm), [3H]NMS-labelled receptors were partially purified by immobilized metal ion affinity chromatography from cultures grown from single clones expressed in *E. Coli* BL21 cells, essentially as described in Hulme and Curtis, 1998 (21). Tm measurements were carried out after gel-filtration of partially purified receptors into 50 mM sodium phosphate, 5 mM β-mercaptoethanol and 0.1% dodecyl-β-maltoside (DDM), using an incubation time of 30 min. Values were tabulated as mean±range/SEM of 2 or more independent measurements (Table 3).

Results

The results are summarized in Table 3, and illustrated in FIGS. 9 and 10.

In-Situ Stability Measurements:

The in-situ assays predicted significantly reduced stability, relative to L65A, for Ala-mutants of I73, I74, V409 from the β1 AR-homologous group, and M114, corresponding to E122 in the β2AR. Two mutants were predicted to be more stable, namely E397A and W101A. E397A is one of the β1 AR homologous residues, but is not a member of the M23 group. Y82A was predicted to have enhanced stability in 2 out of 3 experiments.

Thermal Stability Measurements:

Full Tm measurements on partially purified mutants confirmed reduced stability for I73A, showed no change for I74A, and showed reduced stability for V409A and M114W. Reduced stability was also found for Y82A and V413A. The assays confirmed increased stability for E397A and W101A, and suggested a marginal increase for T202A. Additionally, the Tm measurements have consistently suggested that L65V may be even more stable than L65A in DDM.

TABLE 2

Sequence modifications in the 3C-wild-type $M_1$ mAChR construct

| Modification | Sequence |
| --- | --- |
| malE-3C-M1 N-term | A L K D A Q T G S L E V L F Q ↑ G P M N T |
| ICL3 deletion (129 aa) | R A R E L A A -- T F S L V K E K K |
| C-terminus | C R W D K R R W R K I P K R P G S V H H H H H H H H Q G G |

TABLE 3

M₁ mAChR mutants evaluated for enhanced thermostability

| M₁ mAChR mutant | Turkey β1 AR equivalent | BW number | Stability (βOG in-situ) % L65A control | Tm (0.1% DDM) ° C. |
|---|---|---|---|---|
| 3C-WT | | | 40 ± 5*** | 27.3 ± 0.3 |
| L65A | T81 | 2.44 | 100 | 29.3 ± 0.4 |
| L65V[b] | T81 | 2.44 | 115 | 32.6 ± 0.4 |
| L65F[b] | | | 74 ± 16 | 30.2 ± 0.5 |
| L65A/I73A[a] | V89 | 2.52 | 46 ± 2*** | 27.0 ± 0.5 |
| L65A/I74A[a] | M90 | 2.53 | 51 ± 3** | 28.8 ± 0.5 |
| L65A/Y82A[a] | G98 | 2.61 | 175 ± 61 | 25.3 ± 0.5 |
| L65A/W101A[c] | W117 | 3.28 | 136 ± 9* | 31.0 ± 0.4 |
| L65A/M114W[d] | E130 | 3.41 | 69 ± 7** | 27.8 ± 0.8 |
| L65A/M114Y[d] | | | 48 ± 17*** | ND |
| L65A/L144A[a] | V160 | 4.44 | 125 ± 16 | 29.8 ± 1.0 |
| L65A/T202A[a] | L221 | 5.52 | 94 ± 1 | 31.1 ± 0.2 |
| L65A/C205A[a] | I224 | 5.55 | 106 ± 5 | 28.1 ± 0.1 |
| L65A/Y208A[a] | Y227 | 5.58 | 100 ± 7 | 29.6 ± 0.5 |
| L65A/E397A[a] | D322 | 7.32 | 166 ± 16 | 33.6 ± 0.2 |
| L65A/L402A[a] | F327 | 7.37 | 105 ± 10 | 30.1 ± 0.5 |
| L65A/V409A[a] | A334 | 7.44 | 34 ± 3*** | 26.8± |
| L65A/V413A[a] | F338 | 7.48 | 69 ± 7 | 26.4 ± 0.5 |

[a]Homologues in rat M₁ of mutants that stabilize turkey β1 adrenergic receptor
[b]Alternative mutations of L65 including L65V selected from random mutagenesis screen and L65F (homologous to M₄ mAChR)
[c]W101A enhances affinity of M₁ mAChR for selective agonists 77-LH-28-1 and AC-42
[d]Homologue of E122W/Y thermostabilising mutants in β₂ adrenergic receptor
*P < 0.05 relative to L65A
**P < 0.01 relative to L65A
***P < 0.001 relative to L65A

CONCLUSION

In-situ stability measurements and full thermal stability measurements on this set of mutants have given reasonably consistent results. The in-situ method successfully predicted the stabilizing effect of the E397A and W101A mutations, but did not capture the more marginal effect of the T202A mutation. It was also successful in predicting several of the destabilizing mutations. It has not given false positives. It is noted that the environment of the receptor in the two assays is different.

Taken overall, so far only 2 of the 11 β1AR-homologous mutants have turned out to have a stabilizing effect on the M₁ mAChR. The mutation with the largest effect, E397A, is in a position which is known to be important in the binding of allosteric agents such as MT-7 to the M₁ (22) and LY2033298 to the M4 mAChR (20). The stabilising effect of the W101A mutation is also encouraging.

It is notable that several of the M23-homologous positions in the TM domain gave destabilization after Ala-substitution, namely Ile 73(2.52), Ile 74(2.53), Val 409(7.44) and Val 413 (7.48) (Table 3). This suggests that these sequence positions are indeed important for the stability of the M1 mAChR. In two of these cases, we have shown that substitution of another aliphatic amino acid has provided an extra increment of stability assessed using full thermal stability assays in 0.1% dodecyl maltoside. These increments were 0.9° C. for I73L and 2.5° C. for V413L.

Finally, we are able to confirm that the M114W and M114Y mutations are destabilizing in the M₁ mAChR, so that mutations of this position in TM3 are not transferable from the β2AR.

REFERENCES

1. S. H. White (2004) *Protein Sci* 13, 1948-1949.
2. C. G. Tate (2001) *FEBS Left* 504, 94-98.
3. R. Grisshammer, C. G. Tate (1995) *Q Rev Biophys* 28, 315-422.
4. J. U. Bowie (2001) *Curr Opin Struct Biol* 11, 397-402.
5. F. W. Lau, S. Nauli, Y. Zhou, J. U. Bowie (1999) *J Mol Biol* 290, 559-564.
6. Y. Zhou, J. U. Bowie (2000) *J Biol Chem* 275, 6975-6979.
7. S. Faham, D. Yang, E. Bare, S. Yohannan, J. P. Whitelegge, J. U. Bowie (2004) *J Mol Biol* 335, 297-305.
8. Y. Yarden, H. Rodriguez, S. K. Wong, D. R. Brandt, D. C. May, J. Burnier, R. N. Harkins, E. Y. Chen, J. Ramachandran, A. Ullrich, et al (1986) *Proc. Natl. Acad. Sci. USA* 83, 6795-6799.
9. T. Warne, J. Chirnside, G. F. Schertler (2003) *Biochim Biophys Acta* 1610, 133-140.
10. E. M. Parker, E. M. Ross (1991) *J Biol Chem* 266, 9987-9996.
11. E. M. Parker, K. Kameyama, T. Higashijima, E. M. Ross (1991) *J Biol Chem* 266, 519-527.
12. W. J. Degrip (1982) *Methods in Enzymology* 81, 256-265.
13. K. Palczewski, T. Kumasaka, T. Hori, C. A. Behnke, H. Motoshima, B. A. Fox, I. Le Trong, D. C. Teller, T. Okada, R. E. Stenkamp, et al (2000) *Science* 289, 739-745.
14. J. Li, P. C. Edwards, M. Burghammer, C. Villa, G. F. Schertler (2004) *J Mol Biol* 343, 1409-1438.
15. R. Jaenicke, G. Bohm (1998) *Current Opinion in Structural Biology* 8, 738-748.
16. J. Tucker, R. Grisshammer (1996) *Biochem J* 317 (Pt 3), 891-899.
17. W. Schaffner, C. Weissmann (1973) *Anal. Biochem.* 56, 502-514.

18. C. G. Tate (1998) *Methods Enzymol* 296, 443-455.
19. H. M. Weiss, R. Grisshammer (2002) *Eur J Biochem* 269, 82-92.
20. Chan W Y, McKinzie D L, Bose S, Mitchell S N, Witkin J M, Thompson R C, Christopoulos A, Lazareno S, Birdsall N J, Bymaster F P and Felder C C (2008) *Proc Natl Acad Sci USA* 105: pp 10978-10983.
21. Hulme E C and Curtis C A M (1998) Biochemical Society Transactions 26: pp S361.
22. Kukkonen A, Perakyla M, Akerman K E and Nasman J (2004) *J Biol Chem* 279: pp 50923-50929.
23. Roth C B, Hanson M A and Stevens R C (2008) *J Mol Biol* 376: pp 1305-1319.
24. Serrano-Vega M J, Magnani F, Shibata Y and Tate C G (2008) *Proc Natl Acad Sci USA* 105: pp 877-882.
25. Spalding T A, Ma J N, Ott T R, Friberg M, Bajpai A, Bradley S R, Davis R E, Brann M R and Burstein E S (2006) *Mol Pharmacol* 70: pp 1974-1983.

The invention claimed is:

1. A method for selecting a G-protein coupled receptor (GPCR) with increased stability, the method comprising:
   a) providing one or more mutants of a parent GPCR in a membrane-containing composition,
   b) exposing the one or more mutants of a parent GPCR in the membrane-containing composition to an amount of a membrane destabilising agent which is effective to destabilise the parent GPCR in-situ without solubilising the GPCR,
   c) determining whether the or each mutant GPCR has increased stability with respect to its structure or a biological activity compared to the stability of the parent GPCR with respect to its structure or the same biological activity, and
   d) selecting the one or more mutants which have increased stability compared to the stability of the parent GPCR.

2. A method according to claim 1, wherein the membrane containing composition is any of a composition comprising whole cells, an organelle, a membrane-containing extract or fraction from a cell or organelle, a lipid monolayer, a lipid bilayer, a bead-linked lipid particle or a proteoliposome.

3. A method according to claim 1, wherein the destabilising agent is any of a detergent, an amphiphilic molecule or an amphipol.

4. A method according to claim 1, wherein the amount of a membrane destabilising agent which is effective to destabilise the parent GPCR in-situ is one which reduces a biological activity of the parent GPCR in situ compared to the activity of the parent GPCR in situ in the absence of the destabilising agent.

5. A method according to claim 4, wherein the amount is one which reduces the biological activity of the parent GPCR in situ to approximately 50% of the biological activity of the parent GPCR in situ in the absence of destabilising agent.

6. A method according to claim 1, wherein the biological activity is any of a ligand-binding activity, a signalling pathway modulation activity, a transmembrane transporting activity or an enzyme activity.

7. A method according to claim 1, wherein the amount of a membrane destabilising agent which is effective to destabilise the parent GPCR in-situ is one which significantly perturbs the structure of a parent GPCR in situ compared to the structure of a parent GPCR in situ in the absence of the destabilising agent.

8. A method according to claim 1, wherein the method further comprises determining if the selected one or more mutants have increased stability to any one or more of heat, a detergent, a chaotrope or an extreme of pH and selecting those mutants that do.

9. A method according to claim 8 wherein a mutant GPCR which has increased thermostability is selected.

10. A method for preparing a mutant GPCR with increased stability, the method comprising:
 (a) carrying out the method of claim 1,
 (b) identifying the position or positions of the mutated amino acid residue or residues in the mutant GPCR which has been selected for increased stability, and
 (c) synthesising a mutant GPCR which contains a replacement amino acid at one or more of the positions identified.

11. A method according to claim 10 wherein the mutant GPCR contains a plurality of mutations compared to the parent GPCR.

12. A method according to claim 1 wherein the GPCR is expressed in a prokaryotic host cell.

13. A method according to claim 12, wherein the prokaryotic host cell is *E. coli*.

14. A method according to claim 6, wherein the ligand-binding activity is assessed using a detectably labeled binding partner.

15. A method according to claim 1, wherein the GPCR is incubated for a defined time in the presence of a test detergent and the stability is determined using ligand binding.

16. A method according to claim 6, wherein the GPCR is incubated for a defined time in the presence of a test detergent and the stability is determined using ligand binding.

17. A method according to claim 1, wherein the destabilising agent is any of a trifluoroethanol, a chloroform/methanol mixture, a polyol, butane diol, heptane triol, an alcohol, propanol, isopropanol or benzyl alcohol.

18. A method according to claim 1, wherein the destabilising agent is any of mellitin, an apolipoprotein, an enzyme that perturbs membrane structure or phospholipase A.

19. A method according to claim 1, wherein the destabilising agent is any of an organic solvent, dimethylformide or dimethylsulphoxide.

20. A method according to claim 1, wherein the destabilising agent is urea or guanidine hydrogen chloride.

21. A method according to claim 1, wherein the destabilising agent is any of cyclodextrin, a polyene antibiotic, a local anaesthetic, procaine, a drug or Chlorpromazine.

* * * * *

SEQUENCE LISTING

```
<160> NUMBER OF SEQ ID NOS: 10

<210> SEQ ID NO 1
<211> LENGTH: 12
<212> TYPE: PRT
<213> ORGANISM: Artificial Sequence
<220> FEATURE:
<223> OTHER INFORMATION: C-terminal purification tag

<400> SEQUENCE: 1

His His His His His His His His His Gln Gly Gly
1               5                   10

<210> SEQ ID NO 2
<211> LENGTH: 20
<212> TYPE: PRT
<213> ORGANISM: Artificial Sequence
<220> FEATURE:
<223> OTHER INFORMATION: N-terminal malE tag

<400> SEQUENCE: 2

Ala Leu Lys Asp Ala Gln Thr Gly Ser Leu Glu Val Leu Phe Gln Gly
1               5                   10                  15

Pro Met Asn Thr
            20

<210> SEQ ID NO 3
<211> LENGTH: 7
<212> TYPE: PRT
<213> ORGANISM: Rattus norvegicus

<400> SEQUENCE: 3

Arg Ala Arg Glu Leu Ala Ala
1               5

<210> SEQ ID NO 4
<211> LENGTH: 9
<212> TYPE: PRT
<213> ORGANISM: Rattus norvegicus

<400> SEQUENCE: 4

Thr Phe Ser Leu Val Lys Glu Lys Lys
1               5

<210> SEQ ID NO 5
<211> LENGTH: 30
<212> TYPE: PRT
<213> ORGANISM: Artificial Sequence
<220> FEATURE:
<223> OTHER INFORMATION: C-terminal purification tag

<400> SEQUENCE: 5

Cys Arg Trp Asp Lys Arg Arg Trp Arg Lys Ile Pro Lys Arg Pro Gly
1               5                   10                  15

Ser Val His His His His His His His His Gln Gly Gly
            20                  25                  30
```

-continued

```
<210> SEQ ID NO 6
<211> LENGTH: 413
<212> TYPE: PRT
<213> ORGANISM: Homo sapiens

<400> SEQUENCE: 6

Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
    50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
                85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Phe Lys Tyr Gln Ser Leu
    130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
    210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
        275                 280                 285

Phe Phe Ile Val Asn Ile Val His Val Ile Gln Asp Asn Leu Ile Arg
    290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
                325                 330                 335

Gln Glu Leu Leu Cys Leu Arg Arg Ser Ser Leu Lys Ala Tyr Gly Asn
            340                 345                 350

Gly Tyr Ser Ser Asn Gly Asn Thr Gly Glu Gln Ser Gly Tyr His Val
        355                 360                 365

Glu Gln Glu Lys Glu Asn Lys Leu Leu Cys Glu Asp Leu Pro Gly Thr
    370                 375                 380
```

```
Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
            405                 410
```

<210> SEQ ID NO 7
<211> LENGTH: 424
<212> TYPE: PRT
<213> ORGANISM: Rattus norvegicus

<400> SEQUENCE: 7

```
Met His Leu Asn Ser Val Pro Gln Gly Thr Pro Gly Glu Pro Asp
1               5                   10                  15

Ala Gln Pro Phe Ser Gly Pro Gln Ser Glu Met Glu Ala Thr Phe Leu
                20                  25                  30

Ala Leu Ser Leu Ser Asn Gly Ser Gly Asn Thr Ser Glu Ser Asp Thr
                35                  40                  45

Ala Gly Pro Asn Ser Asp Leu Asp Val Asn Thr Asp Ile Tyr Ser Lys
            50                  55                  60

Val Leu Val Thr Ala Ile Tyr Leu Ala Leu Phe Val Val Gly Thr Val
65                  70                  75                  80

Gly Asn Ser Val Thr Ala Phe Thr Leu Ala Arg Lys Lys Ser Leu Gln
                85                  90                  95

Ser Leu Gln Ser Thr Val His Tyr His Leu Gly Ser Leu Ala Leu Ser
                100                 105                 110

Asp Leu Leu Ile Leu Leu Leu Ala Met Pro Val Glu Leu Tyr Asn Phe
            115                 120                 125

Ile Trp Val His His Pro Trp Ala Phe Gly Asp Ala Gly Cys Arg Gly
130                 135                 140

Tyr Tyr Phe Leu Arg Asp Ala Cys Thr Tyr Ala Thr Ala Leu Asn Val
145                 150                 155                 160

Ala Ser Leu Ser Val Glu Arg Tyr Leu Ala Ile Cys His Pro Phe Lys
                165                 170                 175

Ala Lys Thr Leu Met Ser Arg Ser Arg Thr Lys Lys Phe Ile Ser Ala
            180                 185                 190

Ile Trp Leu Ala Ser Ala Leu Leu Ala Ile Pro Met Leu Phe Thr Met
195                 200                 205

Gly Leu Gln Asn Arg Ser Gly Asp Gly Thr His Pro Gly Gly Leu Val
            210                 215                 220

Cys Thr Pro Ile Val Asp Thr Ala Thr Val Lys Val Val Ile Gln Val
225                 230                 235                 240

Asn Thr Phe Met Ser Phe Leu Phe Pro Met Leu Val Ile Ser Ile Leu
            245                 250                 255

Asn Thr Val Ile Ala Asn Lys Leu Thr Val Met Val His Gln Ala Ala
            260                 265                 270

Glu Gln Gly Arg Val Cys Thr Val Gly Thr His Asn Gly Leu Glu His
            275                 280                 285

Ser Thr Phe Asn Met Thr Ile Glu Pro Gly Arg Val Gln Ala Leu Arg
            290                 295                 300

His Gly Val Leu Val Leu Arg Ala Val Val Ile Ala Phe Val Val Cys
305                 310                 315                 320

Trp Leu Pro Tyr His Val Arg Arg Leu Met Phe Cys Tyr Ile Ser Asp
                325                 330                 335

Glu Gln Trp Thr Thr Phe Leu Phe Asp Phe Tyr His Tyr Phe Tyr Met
            340                 345                 350
```

```
Leu Thr Asn Ala Leu Phe Tyr Val Ser Ser Ala Ile Asn Pro Ile Leu
            355                 360                 365

Tyr Asn Leu Val Ser Ala Asn Phe Arg Gln Val Phe Leu Ser Thr Leu
    370                 375                 380

Ala Cys Leu Cys Pro Gly Trp Arg His Arg Arg Lys Lys Arg Pro Thr
385                 390                 395                 400

Phe Ser Arg Lys Pro Asn Ser Met Ser Ser Asn His Ala Phe Ser Thr
                405                 410                 415

Ser Ala Thr Arg Glu Thr Leu Tyr
            420

<210> SEQ ID NO 8
<211> LENGTH: 460
<212> TYPE: PRT
<213> ORGANISM: Homo sapiens

<400> SEQUENCE: 8

Met Asn Thr Ser Ala Pro Pro Ala Val Ser Pro Asn Ile Thr Val Leu
1               5                   10                  15

Ala Pro Gly Lys Gly Pro Trp Gln Val Ala Phe Ile Gly Ile Thr Thr
            20                  25                  30

Gly Leu Leu Ser Leu Ala Thr Val Thr Gly Asn Leu Leu Val Leu Ile
        35                  40                  45

Ser Phe Lys Val Asn Thr Glu Leu Lys Thr Val Asn Asn Tyr Phe Leu
    50                  55                  60

Leu Ser Leu Ala Cys Ala Asp Leu Ile Ile Gly Thr Phe Ser Met Asn
65                  70                  75                  80

Leu Tyr Thr Thr Tyr Leu Leu Met Gly His Trp Ala Leu Gly Thr Leu
                85                  90                  95

Ala Cys Asp Leu Trp Leu Ala Leu Asp Tyr Val Ala Ser Asn Ala Ser
            100                 105                 110

Val Met Asn Leu Leu Leu Ile Ser Phe Asp Arg Tyr Phe Ser Val Thr
        115                 120                 125

Arg Pro Leu Ser Tyr Arg Ala Lys Arg Thr Pro Arg Arg Ala Ala Leu
    130                 135                 140

Met Ile Gly Leu Ala Trp Leu Val Ser Phe Val Leu Trp Ala Pro Ala
145                 150                 155                 160

Ile Leu Phe Trp Gln Tyr Leu Val Gly Glu Arg Thr Val Leu Ala Gly
                165                 170                 175

Gln Cys Tyr Ile Gln Phe Leu Ser Gln Pro Ile Ile Thr Phe Gly Thr
            180                 185                 190

Ala Met Ala Ala Phe Tyr Leu Pro Val Thr Val Met Cys Thr Leu Tyr
        195                 200                 205

Trp Arg Ile Tyr Arg Glu Thr Glu Asn Arg Ala Arg Glu Leu Ala Ala
    210                 215                 220

Leu Gln Gly Ser Glu Thr Pro Gly Lys Gly Gly Gly Ser Ser Ser Ser
225                 230                 235                 240

Ser Glu Arg Ser Gln Pro Gly Ala Glu Gly Ser Pro Glu Thr Pro Pro
                245                 250                 255

Gly Arg Cys Cys Arg Cys Cys Arg Ala Pro Arg Leu Leu Gln Ala Tyr
            260                 265                 270

Ser Trp Lys Glu Glu Glu Glu Asp Glu Gly Ser Met Glu Ser Leu
        275                 280                 285

Thr Ser Ser Glu Gly Glu Glu Pro Gly Ser Glu Val Val Ile Lys Met
    290                 295                 300
```

```
Pro Met Val Asp Pro Glu Ala Gln Ala Pro Thr Lys Gln Pro Pro Arg
305                 310                 315                 320

Ser Ser Pro Asn Thr Val Lys Arg Pro Thr Lys Lys Gly Arg Asp Arg
                325                 330                 335

Ala Gly Lys Gly Gln Lys Pro Arg Gly Lys Glu Gln Leu Ala Lys Arg
            340                 345                 350

Lys Thr Phe Ser Leu Val Lys Glu Lys Lys Ala Ala Arg Thr Leu Ser
        355                 360                 365

Ala Ile Leu Leu Ala Phe Ile Leu Thr Trp Thr Pro Tyr Asn Ile Met
    370                 375                 380

Val Leu Val Ser Thr Phe Cys Lys Asp Cys Val Pro Glu Thr Leu Trp
385                 390                 395                 400

Glu Leu Gly Tyr Trp Leu Cys Tyr Val Asn Ser Thr Ile Asn Pro Met
                405                 410                 415

Cys Tyr Ala Leu Cys Asn Lys Ala Phe Arg Asp Thr Phe Arg Leu Leu
            420                 425                 430

Leu Leu Cys Arg Trp Asp Lys Arg Arg Trp Arg Lys Ile Pro Lys Arg
        435                 440                 445

Pro Gly Ser Val His Arg Thr Pro Ser Arg Gln Cys
    450                 455                 460

<210> SEQ ID NO 9
<211> LENGTH: 483
<212> TYPE: PRT
<213> ORGANISM: Meleagris gallopavo

<400> SEQUENCE: 9

Met Gly Asp Gly Trp Leu Pro Pro Asp Cys Gly Pro His Asn Arg Ser
1               5                   10                  15

Gly Gly Gly Gly Ala Thr Ala Ala Pro Thr Gly Ser Arg Gln Val Ser
            20                  25                  30

Ala Glu Leu Leu Ser Gln Gln Trp Glu Ala Gly Met Ser Leu Leu Met
        35                  40                  45

Ala Leu Val Val Leu Leu Ile Val Ala Gly Asn Val Leu Val Ile Ala
    50                  55                  60

Ala Ile Gly Arg Thr Gln Arg Leu Gln Thr Leu Thr Asn Leu Phe Ile
65                  70                  75                  80

Thr Ser Leu Ala Cys Ala Asp Leu Val Met Gly Leu Leu Val Val Pro
                85                  90                  95

Phe Gly Ala Thr Leu Val Val Arg Gly Thr Trp Leu Trp Gly Ser Phe
            100                 105                 110

Leu Cys Glu Cys Trp Thr Ser Leu Asp Val Leu Cys Val Thr Ala Ser
        115                 120                 125

Ile Glu Thr Leu Cys Val Ile Ala Ile Asp Arg Tyr Leu Ala Ile Thr
    130                 135                 140

Ser Pro Phe Arg Tyr Gln Ser Leu Met Thr Arg Ala Arg Ala Lys Val
145                 150                 155                 160

Ile Ile Cys Thr Val Trp Ala Ile Ser Ala Leu Val Ser Phe Leu Pro
                165                 170                 175

Ile Met Met His Trp Trp Arg Asp Glu Asp Pro Gln Ala Leu Lys Cys
            180                 185                 190

Tyr Gln Asp Pro Gly Cys Cys Asp Phe Val Thr Asn Arg Ala Tyr Ala
        195                 200                 205

Ile Ala Ser Ser Ile Ile Ser Phe Tyr Ile Pro Leu Leu Ile Met Ile
    210                 215                 220
```

```
Phe Val Tyr Leu Arg Val Tyr Arg Glu Ala Lys Glu Gln Ile Arg Lys
225                 230                 235                 240

Ile Asp Arg Cys Glu Gly Arg Phe Tyr Gly Ser Gln Glu Gln Pro Gln
            245                 250                 255

Pro Pro Pro Leu Pro Gln His Gln Pro Ile Leu Gly Asn Gly Arg Ala
            260                 265                 270

Ser Lys Arg Lys Thr Ser Arg Val Met Ala Met Arg Glu His Lys Ala
        275                 280                 285

Leu Lys Thr Leu Gly Ile Ile Met Gly Val Phe Thr Leu Cys Trp Leu
        290                 295                 300

Pro Phe Phe Leu Val Asn Ile Val Asn Val Phe Asn Arg Asp Leu Val
305                 310                 315                 320

Pro Asp Trp Leu Phe Val Phe Phe Asn Trp Leu Gly Tyr Ala Asn Ser
            325                 330                 335

Ala Phe Asn Pro Ile Ile Tyr Cys Arg Ser Pro Asp Phe Arg Lys Ala
            340                 345                 350

Phe Lys Arg Leu Leu Cys Phe Pro Arg Lys Ala Asp Arg Arg Leu His
        355                 360                 365

Ala Gly Gly Gln Pro Ala Pro Leu Pro Gly Gly Phe Ile Ser Thr Leu
    370                 375                 380

Gly Ser Pro Glu His Ser Pro Gly Gly Thr Trp Ser Asp Cys Asn Gly
385                 390                 395                 400

Gly Thr Arg Gly Gly Ser Glu Ser Ser Leu Glu Glu Arg His Ser Lys
            405                 410                 415

Thr Ser Arg Ser Glu Ser Lys Met Glu Arg Glu Lys Asn Ile Leu Ala
        420                 425                 430

Thr Thr Arg Phe Tyr Cys Thr Phe Leu Gly Asn Gly Asp Lys Ala Val
        435                 440                 445

Phe Cys Thr Val Leu Arg Ile Val Lys Leu Phe Glu Asp Ala Thr Cys
    450                 455                 460

Thr Cys Pro His Thr His Lys Leu Lys Met Lys Trp Arg Phe Lys Gln
465                 470                 475                 480

His Gln Ala

<210> SEQ ID NO 10
<211> LENGTH: 412
<212> TYPE: PRT
<213> ORGANISM: Homo sapiens

<400> SEQUENCE: 10

Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
            20                  25                  30

Leu Asn Ser Asn Leu Gln Asn Val Thr Asn Tyr Phe Val Val Ser Leu
        35                  40                  45

Ala Ala Ala Asp Ile Ala Val Gly Val Leu Ala Ile Pro Phe Ala Ile
    50                  55                  60

Thr Ile Ser Thr Gly Phe Cys Ala Ala Cys His Gly Cys Leu Phe Ile
65                  70                  75                  80

Ala Cys Phe Val Leu Val Leu Thr Gln Ser Ser Ile Phe Ser Leu Leu
                85                  90                  95

Ala Ile Ala Ile Asp Arg Tyr Ile Ala Ile Arg Ile Pro Leu Arg Tyr
            100                 105                 110
```

```
Asn Gly Leu Val Thr Gly Thr Arg Ala Lys Gly Ile Ile Ala Ile Cys
            115                 120                 125

Trp Val Leu Ser Phe Ala Ile Gly Leu Thr Pro Met Leu Gly Trp Asn
        130                 135                 140

Asn Cys Gly Gln Pro Lys Glu Gly Lys Asn His Ser Gln Gly Cys Gly
145                 150                 155                 160

Glu Gly Gln Val Ala Cys Leu Phe Glu Asp Val Val Pro Met Asn Tyr
                165                 170                 175

Met Val Tyr Phe Asn Phe Phe Ala Cys Val Leu Val Pro Leu Leu Leu
            180                 185                 190

Met Leu Gly Val Tyr Leu Arg Ile Phe Leu Ala Ala Arg Arg Gln Leu
            195                 200                 205

Lys Gln Met Glu Ser Gln Pro Leu Pro Gly Glu Arg Ala Arg Ser Thr
        210                 215                 220

Leu Gln Lys Glu Val His Ala Ala Lys Ser Leu Ala Ile Ile Val Gly
225                 230                 235                 240

Leu Phe Ala Leu Cys Trp Leu Pro Leu His Ile Ile Asn Cys Phe Thr
                245                 250                 255

Phe Phe Cys Pro Asp Cys Ser His Ala Pro Leu Trp Leu Met Tyr Leu
                260                 265                 270

Ala Ile Val Leu Ser His Thr Asn Ser Val Val Asn Pro Phe Ile Tyr
            275                 280                 285

Ala Tyr Arg Ile Arg Glu Phe Arg Gln Thr Phe Arg Lys Ile Ile Arg
        290                 295                 300

Ser His Val Leu Arg Gln Gln Glu Pro Phe Lys Ala Ala Gly Thr Ser
305                 310                 315                 320

Ala Arg Val Leu Ala Ala His Gly Ser Asp Gly Glu Gln Val Ser Leu
                325                 330                 335

Arg Leu Asn Gly His Pro Pro Gly Val Trp Ala Asn Gly Ser Ala Pro
            340                 345                 350

His Pro Glu Arg Arg Pro Asn Gly Tyr Ala Leu Gly Leu Val Ser Gly
        355                 360                 365

Gly Ser Ala Gln Glu Ser Gln Gly Asn Thr Gly Leu Pro Asp Val Glu
370                 375                 380

Leu Leu Ser His Glu Leu Lys Gly Val Cys Pro Glu Pro Pro Gly Leu
385                 390                 395                 400

Asp Asp Pro Leu Ala Gln Asp Gly Ala Gly Val Ser
            405                 410
```